US012600784B2

(12) United States Patent
Yoshihara

(10) Patent No.: US 12,600,784 B2
(45) Date of Patent: *Apr. 14, 2026

(54) ANTI-CLEC12A ANTIBODIES AND USES THEREOF

(71) Applicant: Millennium Pharmaceuticals, Inc., Cambridge, MA (US)

(72) Inventor: Tomoki Yoshihara, Cambridge, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/728,664

(22) Filed: Apr. 25, 2022

(65) Prior Publication Data

US 2023/0111279 A1 Apr. 13, 2023

Related U.S. Application Data

(60) Provisional application No. 63/179,755, filed on Apr. 26, 2021.

(51) Int. Cl.
*C07K 16/28* (2006.01)
*A61K 39/395* (2006.01)
*A61P 35/00* (2006.01)

(52) U.S. Cl.
CPC ...... *C07K 16/2851* (2013.01); *A61K 39/3955* (2013.01); *A61P 35/00* (2018.01); *C07K 2317/21* (2013.01); *C07K 2317/33* (2013.01); *C07K 2317/565* (2013.01); *C07K 2317/622* (2013.01); *C07K 2317/76* (2013.01); *C07K 2317/92* (2013.01)

(58) Field of Classification Search
CPC ............ C07K 16/2851; C07K 2317/21; C07K 2317/33; C07K 2317/565; C07K 2317/622; C07K 2317/76; C07K 2317/92; C07K 16/283; C07K 14/705; C07K 14/7051; C07K 14/70521; C07K 14/755; C07K 2317/34; C07K 2319/03; C07K 2319/33; C07K 16/36; A61K 39/3955; A61K 38/177; A61K 39/4611; A61K 39/4621; A61K 39/4631; A61K 39/464; A61K 48/00; A61K 2239/31; A61K 2239/38; A61K 38/00; A61K 39/001; A61P 35/00; A61P 7/00; C12N 5/0637; C12N 15/867; C12N 2501/51; C12N 2501/515; C12N 2510/00
See application file for complete search history.

(56) References Cited

U.S. PATENT DOCUMENTS

| | | | |
|---|---|---|---|
| 10,358,492 B2 | 7/2019 | Bakker et al. | |
| 2020/0277384 A1 | 9/2020 | Chang et al. | |

| | | | | |
|---|---|---|---|---|
| 2020/0345779 A1 * | 11/2020 | Davila | ............... | A61K 39/4644 |
| 2020/0347139 A1 | 11/2020 | Rascon et al. | | |
| 2020/0384084 A1 | 12/2020 | Bakker et al. | | |
| 2022/0363775 A1 * | 11/2022 | Sadelain | ............ | C07K 16/2896 |

FOREIGN PATENT DOCUMENTS

| | | | | |
|---|---|---|---|---|
| CA | 3088878 A1 | 7/2019 | | |
| CL | 2017/00590 A1 | 10/2017 | | |
| CL | 2022/03077 A1 | 4/2022 | | |
| CL | 2023/003185 A1 | 4/2024 | | |
| CL | 2020/003174 A1 | 5/2024 | | |
| WO | 2016/040868 A1 | 3/2016 | | |
| WO | WO-2020140088 A1 * | 7/2020 | ............. | A61K 45/06 |
| WO | 2021/226193 A1 | 11/2021 | | |
| WO | 2022/232016 A2 | 11/2022 | | |
| WO | 2022/232035 A1 | 11/2022 | | |

OTHER PUBLICATIONS

International Search Report and Written Opinion for PCT/US2022/026175 dated Nov. 11, 2022 (19 pages).
Morsink, Linde M., et al., "Novel monoclonal antibody-based therapies for acute myeloid leukemia", Best Practice & Research Clinical Haematology, vol. 32, No. 2, Jun. 2019, pp. 116-126, DOI: 10.1016/j.beha.2019.05.002 (11 pages).
Noordhuis, Paul, et al., "Targeting of CLEC12A in Acute Myeloid Leukemia by Antibody-Drug-Conjugates and Bispecific CLL-1×CD3 BiTE Antibody", Blood, vol. 116, No. 21, Nov. 19, 2010, pp. 2890, DOI: 10.1182/blood. V116.21.2890.2890 (3 pages).
Dondelinger, et al., "Understanding the Significance and Implications of Antibody Numbering and Antigen-Binding Surface/Residue Definition", Frontiers in Immunology, Oct. 16, 2018; vol. 9, DOI:10.3389/fimmu.2018.02278 XP055572450 DOI: http://dx.doi.org/10.3389/fimmu.2018.02278, pp. 1-15 (15 pages).
Kussie, et al., "A Single Engineered Amino Acid Substitution Changes Antibody Specificity", The Journal of Immunology, Jan. 1, 1994; 152 (1): https://doi.org/10.4049/jimmunol.152.1.146, pp. 146-152 (8 pages).
Liu, et al., "Fine Mapping of the Antigen-Antibody Interaction of Scfv215, A Recombinant Antibody Inhibiting RNA Polymerase II from *Drosophila melanogaster*", Journal of Molecular Recognition; Mar.-Apr. 1999; 12(2):103-11. DOI: 10.1002/(SICI)1099-1352(199903/04)12:2<103:AID-JMR447>3.0.CO;2-B (9 pages).
Panka, et al., "Variable Region Framework Differences Result in Decreased or Increased Affinity of Variant Anti-digoxin Antibodies", Proceedings of the National Academy of Sciences of the United States of America; vol. 85, May 1988, Immunology; 85(9):3080-4. DOI: 10.1073/pnas.85.9.3080, pp. 3080-3084 (4 pages).

(Continued)

*Primary Examiner* — Adam Weidner
*Assistant Examiner* — Laura Ann Essex
(74) *Attorney, Agent, or Firm* — Proskauer Rose LLP

(57) ABSTRACT

Antibodies, fragments thereof and fusion proteins that specifically bind to Clec12A, are described, as well as methods of making and using such antibodies. Such antibodies, fusion proteins and fragments thereof are useful for the treatment and diagnosis of various autoimmune diseases and cancers, including leukemia, lymphoma, or myeloma, including, for example, acute myeloid leukemia.

11 Claims, 7 Drawing Sheets

Specification includes a Sequence Listing.

(56) References Cited

OTHER PUBLICATIONS

Rudikoff, et al., "Single Amino Acid Substitution Altering Antigen-Binding Specificity", Proceedings of the National Academy of Sciences USA, Immunology, vol. 79, Mar. 1982, pp. 1979-1983 (5 pages).

Sela-Culang, et al., "The Structural Basis of Antibody-Antigen Recognition", Frontiers in Immunology, Oct. 8, 2013, vol. 4, doi:10.3389/fimmu.2013.00302, XP055557261 DOI: http://dx.doi.org/10.3389/fimmu.2013.00302; pp. 1-13 (13 pages).

Wong, et al., "Structural Requirements for a Specificity Switch and for Maintenance of Affinity Using Mutational Analysis of a Phage-Displayed Anti-Arsonate Antibody of Fab Heavy Chain First Complementarity-Determining Region", The Journal of Immunology, Jun. 15, 1998, 160 (12): https://doi.org/10.4049/jimmunol.160.12.5990; pp. 5990-5997 (9 pages).

Xiang, et al., "Modification in Framework Region I Results in a Decreased Affinity of Chimeric Anti-TAG72 Antibody", Molecular Immunology 28(1-2) Jan.-Feb. 1991; DOI: 10.1016/0161-5890(91)90097-4; https://doi.org/10.1016/0161-5890(91)90097-4, pp. 141-148 (7 pages).

Bostrom, et al., "Improving Antibody Binding Affinity and Specificity for Therapeutic Development", Methods Molecular Biology, 2009; 525:353-76, xiii. DOI: 10.1007/978-1-59745-554-1_19, pp. 353-376 (24 pages).

Frenzel, et al., "Chapter 6: Antibody Affinity", Handbook of Therapeutic Antibodies, First published: Aug. 12, 2014, https://DOI.org/10.1002/9783527682423.ch6, pp. 115-139 (25 pages).

Gonzales, et al: "Minimizing the Immunogenicity of Antibodies for Clinical Application"; Tumour Biology, Jan.-Feb. 2005; 26(1):31-43. DOI: 10.1159/000084184, pp. 31-43 (13 pages).

Kunik, et al., "Structural Consensus Among Antibodies Defines the Antigen Binding Site", PLoS Computational Biology, Feb. 2012, vol. 8 Issue 2 DOI: 10.1371/journal.pcbi.1002388, www.ploscompbiol.org, pp. 1-12 (12 pages).

Wark, et al., "Latest Technologies for the Enhancement of Antibody Affinity", Advanced Drug Delivery Reviews, Elsevier, Jan. 25, 2006, vol. 58, No. 5-6, DOI:10.1016/J.ADDR.2006.01.025, ISSN 0169-409X, (Aug. 7, 2006), pp. 657-670 (14 pages).

Wu, et al., "Humanization of a Murine Monoclonal Antibody by Simultaneous Optimization of Framework and CDR Residues", Journal of Molecular Biology, 1999, 294, www.idcalibrary.com pp. 151-162 (12 pages).

* cited by examiner

ANTI-CLEC12A ANTIBODIES AND USES THEREOF

CROSS REFERENCED APPLICATIONS

This application claims priority to, and the benefit of, U.S. provisional application No. 63/179,755, filed on Apr. 26, 2021, the contents of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Nov. 10, 2022, is named MIL-017US1_SL_v3.txt and is 44 KB in size.

PARTIES TO A JOINT RESEARCH AGREEMENT

The instant application was made by or on behalf of a party to a joint research agreement. The parties to the joint research agreement are Millennium Pharmaceuticals Inc. and Memorial Sloan-Kettering Cancer Center.

BACKGROUND

Anti-Clec12A antibodies bind Clec12A antigen, also known as MICL or C-type lectin domain family 12 member A. Clec12A antigen is an inhibitory C-type lectin-like receptor. Human MICL is expressed as a monomer primarily on myeloid cells, including granulocytes, monocytes, macrophages and dendritic cells. Murine MICL is expressed as dimer on granulocytes, monocytes but also on B lymphocytes and can be also found on NK cells surface in bone marrow.

The Clec12A gene encodes a member of the C-type lectin/C-type lectin-like domain (CTI/CTLD) superfamily, which shares a common protein fold and has diverse functions, such as cell adhesion, cell-cell signaling, glycoprotein turnover, and roles in inflammation and immune response. The protein encoded by this gene inhibits granulocyte and monocyte function.

SUMMARY OF INVENTION

The present invention provides human anti-Clec12A antibodies and fragments thereof, for the treatment of autoimmune diseases and cancers, including leukemia, lymphoma, or myeloma, including, for example, relapsed and refractory acute myeloid leukemia. The antibodies and fragments thereof of the present invention can be used alone, in fusion proteins or conjugated to at least one diagnostic and/or therapeutic agent or in combination with other treatment modalities. Binding of human Clec12A with the anti-Clec12A antibodies or fragments thereof described herein may demonstrate Antibody-dependent cellular cytotoxicity (ADCC) activity, including for example induction of apoptosis and inhibition of cancer cell proliferation.

In some aspects, an anti-Clec12A antibody or an antigen-binding fragment thereof is provided comprising:

(a) an immunoglobulin heavy chain variable (VH) region comprising an amino acid sequence that is at least 80% identical to

```
                                    (SEQ ID NO: 1)
QVQLQESGPGLVKPSETLSLTCTVSGGSISTYYWSWIRQPPGKGLEWIGYI

YYSGSTKYNPSLKSRVTISVDTSKNLFSLKLSSVTAADTAVYYCAREDYYG

SGSPFDYWGQGTLVTVSS,
and
``` an immunoglobulin light chain variable (VL) region comprising an amino acid sequence that is at least about 80% identical to

```
                                    (SEQ ID NO: 2)
IQMTQSPSSLSASVGDRVTITCRASQGIRYDLGWYQQKPGKAPKLLIYAAS

SLQSGVPSRFSGSGSGTDFTLTISSLQPEDFATYYCLQDYNFPRTFGQGTK

VEIK;
```

(b) an immunoglobulin heavy chain variable (VH) region comprising an amino acid sequence that is at least about 80% identical to

```
                                    (SEQ ID NO: 3)
QVQLVESGGGVVQPGRSLRLSCAASGFTFSSYGMHWVRQAPGKGLEWVAVI

SYDGSDKYYVDSVKGRFTISRDNSKNTLYLHMNSLRAEDTAVYYCARDKGY

YFDYWGQGTLVTVSS,
and
``` an immunoglobulin light chain variable (VL) region comprising an amino acid sequence that is at least about 80% identical to

```
                                    (SEQ ID NO: 4)
EIVMTQSPATLSLSPGERATLSCRASQSVGNRYLSWYQQKPGQAPRLLIY

GASTRATGIPARFSGSGSGTDFTLTISSLQPEDFAVYYCQQDYNLPLTFG

GGTKVEIK;
```

(c) an immunoglobulin heavy chain variable (VH) region comprising an amino acid sequence that is at least about 80% identical to

```
                                    (SEQ ID NO: 5)
QVQLVESGGGVVQPGRSLRLSCAASGFTFSSYGMHWVRQAPGKGLEWVAV

ISYDGSDKYSADSVKGRFNISRDNSKNTLYLQMNSLRAEDTAVYYCARDG

SRYFDYWGQGTLVTVSS,
and
``` an immunoglobulin light chain variable (VL) region comprising an amino acid sequence that is at least about 80% identical to

```
                                    (SEQ ID NO: 6)
EIFMTQSPATLSLSPGERATLSCRASQSVHSKYLSWYQQKPGQAPSLLIY

GASTRATGIPARFSGSGSGTDFTLTISSLQPEDFAVYYCQQDYNLPITFG

QGTRLEIK;
or
```

(d) an immunoglobulin heavy chain variable (VH) region comprising an amino acid sequence that is at least about 80% identical to (SEQ ID NO: 7)
QLQLQESGPGLVKPSETLSLTCTVSGGSISSSTYYWGWIRQPPRKGLEWI

GSTHYRGSTYYNPSLKSRVTISVDTSKNQFSLKVSSVTAADTAVYYCARE

LTGEVFDYWGQGTLVTVSS,
and an immunoglobulin light chain variable (VL) region comprising an amino acid sequence that is at least about 80% identical to (SEQ ID NO: 8)
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPFTFGP

GTKVDIK;

(e) an immunoglobulin heavy chain variable (VH) region comprising an amino acid sequence that is at least about 80% identical to (SEQ ID NO: 9)
QVQLQESGPGLVKPSETLSLTCTVSGGSISTYYWSWIRQPPGKGLEWLGY

IYFSGSTNYNPSLKSRLTISVAASKSQFSLKLSSVTAADTAVYYCAREDY

YGSGSPFDYWGQGTLVTVSS,
and an immunoglobulin light variable (VL) region comprising an amino acid sequence that is at least about 80% identical to (SEQ ID NO: 10)
AIQMTQSPSSLSASVGDRVTITCRASQGIRNDLGWFQQKPGKAPKLLIYA

ASSLQSGVPSRFSGSGSGTYFTLTISSLQPEDSATYYCLQDYNYPRTFGQ

GTKVEIK;

(f) an immunoglobulin heavy chain variable (VH) region comprising an amino acid sequence that is at least about 80% identical to (SEQ ID NO: 11)
QVQLQESGPGLVKPSETLSLTCTVSGGSISTDYWSWIRQPPGKGLEWIGY

IYFSGSTKYNPSLKSRVTISVDTSKNQFSLKLSSVTAADTAVYYCAREDY

YGSGSPFDYWGQGTLVTVSS,
and an immunoglobulin light variable (VL) region comprising an amino acid sequence that is at least about 80% identical to (SEQ ID NO: 12)
AIQMTQSPSSLSASVGDRVTITCRASQDIRNDLGWFQQKPGKAPKLLIYA

ASSLQSGVPSRFSGSGSGTDFTLTISSLQPEDFATYYCLQDYNFPRTFGQ

GTKVEIK;

(g) an immunoglobulin heavy chain variable (VH) region comprising an amino acid sequence that is at least about 80% identical to (SEQ ID NO: 13)
QVQLVESGGGVVQPGRSLRLSCAASGFTFSSYGMHWVRQAPGEGLEWVTV

ISYDGSDKYYADSVKGRFTISRDNSKSTLFLQMNSLRAEDTAVYYCARDG

QFYFDYWGQGTLVTVSS,
and an immunoglobulin light variable (VL) region comprising an amino acid sequence that is at least about 80% identical to (SEQ ID NO: 14)
EIVMTQSPATLSLSPGESATLSCRASQSVTSRYLSWYQQKPGQAPRLLMY

GASTRPTGIPARFSGSGSGTDFTLTISSLQPEDFAVYYCQQDYNLPLTFG

GGTKVEIK;

(h) an immunoglobulin heavy chain variable (VH) region comprising an amino acid sequence that is at least about 80% identical to (SEQ ID NO: 15)
QVQLVESGGGVVQPGRSLRLSCAASGFTFSNYGMHWVRQAPGKGLEWVAV

ISYDGSDKSYKDSVKGRFTIARDNSKNTLYLQMNSLRAEDTAVYYCARDS

GRYFFDYWGQGTLVTVSS,
and an immunoglobulin light variable (VL) region comprising an amino acid sequence that is at least about 80% identical to (SEQ ID NO: 16)
EIIMTQSPATLSLSPGERATLSCRASQSVSSRSLSWYQHKPGQAPRLLIY

GPSTRATGIPARFSGSGSGTDFTLTISSLQPEDFAVYYCHQDYNLPLTFG

GGTKVEIK;
or (i) an immunoglobulin heavy chain variable (VH) region comprising an amino acid sequence that is at least about 80% identical to (SEQ ID NO: 17)
QVKLVESGGGVVQPGRSLRLSCAASGFTFSKYGMHWVRQAPGKGLEWVAF

IWYDGSIKNYADSVKGRFTTSRDNSKNTLYLQMNSLRAEDTAVYYCARGS

LWFGEFYFDYWGQGTLVTVSS,
and an immunoglobulin light variable (VL) region comprising an amino acid sequence that is at least about 80% identical to (SEQ ID NO: 18)
AIQLTQSPSSLSASVGDRVTITCRTSQGISSALAWYQQKPGKTPKLLIYD

ASSLESGVPSRFSGSGSGTDFTLTISSLQPEDFATYYCQQFNNYPRTFGQ

GTKVEIK.

5

In some embodiments, the anti-Clec12A antibody or antibody-binding fragment thereof comprises:

(a) an immunoglobulin heavy chain variable (VH) region comprising an amino acid sequence of (SEQ ID NO: 1)
QVQLQESGPGLVKPSETLSLTCTVSGGSISTYYWSWIRQPPGKGLEWIGY

IYYSGSTKYNPSLKSRVTISVDTSKNLFSLKLSSVTAADTAVYYCAREDY

YGSGSPFDYWGQGTLVTVSS,
and an immunoglobulin light chain variable (VL) region comprising an amino acid sequence of (SEQ ID NO: 2)
IQMTQSPSSLSASVGDRVTITCRASQGIRYDLGWYQQKPGKAPKLLIYAA

SSLQSGVPSRFSGSGSGTDFTLTISSLQPEDFATYYCLQDYNFPRTFGQG

TKVEIK;

(b) an immunoglobulin heavy chain variable (VH) region comprising an amino acid sequence of (SEQ ID NO: 3)
QVQLVESGGGVVQPGRSLRLSCAASGFTFSSYGMHWVRQAPGKGLEWVAV

ISYDGSDKYYVDSVKGRFTISRDNSKNTLYLHMNSLRAEDTAVYYCARDK

GYYFDYWGQGTLVTVSS,
and an immunoglobulin light chain variable (VL) region comprising an amino acid sequence of (SEQ ID NO: 4)
EIVMTQSPATLSLSPGERATLSCRASQSVGNRYLSWYQQKPGQAPRLLIY

GASTRATGIPARFSGSGSGTDFTLTISSLQPEDFAVYYCQQDYNLPLTFG

GGTKVEIK;

(c) an immunoglobulin heavy chain variable (VH) region comprising an amino acid sequence (SEQ ID NO: 5)
QVQLVESGGGVVQPGRSLRLSCAASGFTFSSYGMHWVRQAPGKGLEWVAV

ISYDGSDKYSADSVKGRFNISRDNSKNTLYLQMNSLRAEDTAVYYCARDG

SRYFDYWGQGTLVTVSS,
and an immunoglobulin light chain variable (VL) region comprising an amino acid sequence of (SEQ ID NO 6)
EIFMTQSPATLSLSPGERATLSCRASQSVHSKYLSWYQQKPGQAPSLLIY

GASTRATGIPARFSGSGSGTDFTLTISSLQPEDFAVYYCQQDYNLPITFG

QGTRLEIK;
or

6

(d) an immunoglobulin heavy chain variable (VH) region comprising an amino acid sequence of (SEQ ID NO: 7)
QLQLQESGPGLVKPSETLSLTCTVSGGSISSSTYYWGWIRQPPRKGLEWI

GSTHYRGSTYYNPSLKSRVTISVDTSKNQFSLKVSSVTAADTAVYYCARE

LTGEVFDYWGQGTLVTVSS,
and an immunoglobulin light chain variable (VL) region comprising an amino acid sequence of (SEQ ID NO: 8)
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPFTFGP

GTKVDIK;

(e) an immunoglobulin heavy chain variable (VH) region comprising an amino acid sequence of (SEQ ID NO: 9)
QVQLQESGPGLVKPSETLSLTCTVSGGSISTYYWSWIRQPPGKGLEWLGY

IYFSGSTNYNPSLKSRLTISVAASKSQFSLKLSSVTAADTAVYYCAREDY

YGSGSPFDYWGQGTLVTVSS,
and an immunoglobulin light variable (VL) region comprising an amino acid sequence of (SEQ ID NO: 10)
AIQMTQSPSSLSASVGDRVTITCRASQGIRNDLGWFQQKPGKAPKLLIYA

ASSLQSGVPSRFSGSGSGTYFTLTISSLQPEDSATYYCLQDYNYPRTFGQ

GTKVEIK;

(f) an immunoglobulin heavy chain variable (VH) region comprising an amino acid sequence of (SEQ ID NO: 11)
QVQLQESGPGLVKPSETLSLTCTVSGGSISTDYWSWIRQPPGKGLEWIGY

IYFSGSTKYNPSLKSRVTISVDTSKNQFSLKLSSVTAADTAVYYCAREDY

YGSGSPFDYWGQGTLVTVSS,
and an immunoglobulin light variable (VL) region comprising an amino acid sequence of (SEQ ID NO: 12)
AIQMTQSPSSLSASVGDRVTITCRASQDIRNDLGWFQQKPGKAPKLLIYA

ASSLQSGVPSRFSGSGSGTDFTLTISSLQPEDFATYYCLQDYNFPRTFGQ

GTKVEIK;

7

(g) an immunoglobulin heavy chain variable (VH) region comprising an amino acid sequence of

```
(SEQ ID NO: 13)
QVQLVESGGGVVQPGRSLRLSCAASGFTFSSYGMHWVRQAPGEGLEWVTV

ISYDGSDKYYADSVKGRFTISRDNSKSTLFLQMNSLRAEDTAVYYCARDG

QFYFDYWGQGTLVTVSS,
and
``` an immunoglobulin light variable (VL) region comprising an amino acid sequence of

```
(SEQ ID NO: 14)
EIVMTQSPATLSLSPGESATLSCRASQSVTSRYLSWYQQKPGQAPRLLMY

GASTRPTGIPARFSGSGSGTDFTLTISSLQPEDFAVYYCQQDYNLPLTFG

GGTKVEIK;
```

(h) an immunoglobulin heavy chain variable (VH) region comprising an amino acid sequence of

```
(SEQ ID NO: 15)
QVQLVESGGGVVQPGRSLRLSCAASGFTFSNYGMHWVRQAPGKGLEWVAV

ISYDGSDKSYKDSVKGRFTIARDNSKNTLYLQMNSLRAEDTAVYYCARDS

GRYFFDYWGQGTLVTVSS,
and
``` an immunoglobulin light variable (VL) region comprising an amino acid sequence of

```
(SEQ ID NO: 16)
EIIMTQSPATLSLSPGERATLSCRASQSVSSRSLSWYQHKPGQAPRLLIY

GPSTRATGIPARFSGSGSGTDFTLTISSLQPEDFAVYYCHQDYNLPLTFG

GGTKVEIK;
or
```

(i) an immunoglobulin heavy chain variable (VH) region comprising an amino acid sequence of

```
(SEQ ID NO: 17)
QVKLVESGGGVVQPGRSLRLSCAASGFTFSKYGMHWVRQAPGKGLEWVAF

IWYDGSIKNYADSVKGRFTTSRDNSKNTLYLQMNSLRAEDTAVYYCARGS

LWFGEFYFDYWGQGTLVTVSS,
and
``` an immunoglobulin light variable (VL) region comprising an amino acid sequence of

```
(SEQ ID NO: 18)
AIQLTQSPSSLSASVGDRVTITCRTSQGISSALAWYQQKPGKTPKLLIYD

ASSLESGVPSRFSGSGSGTDFTLTISSLQPEDFATYYCQQFNNYPRTFGQ

GTKVEIK.
```

In some embodiments, the anti-Clec12A antibody or antibody-binding fragment thereof comprises:

(a) a heavy chain complementarity determining region (HCDR) 1 comprising an amino acid sequence of GGSISTYY (SEQ ID NO: 19), an HCDR2 comprising an amino acid sequence of IYYSGST (SEQ ID NO: 20), an HCDR3 comprising an amino acid sequence of AREDYYGSGSPFDY (SEQ ID NO: 21); and

a light chain complementarity determining region (LCDR) 1 comprising an amino acid sequence of QGIRYD (SEQ ID NO: 22), an LCDR2 comprising an amino acid sequence of AAS (SEQ ID NO:23), and an LCDR3 comprising an amino acid sequence of LQDYNFPRT (SEQ ID NO: 24);

(b) an HCDR1 comprising an amino acid sequence of GFTFSSYG (SEQ ID NO: 73), an HCDR2 comprising an amino acid sequence of ISYDGSDK (SEQ ID NO: 25), and HCDR3 comprising an amino acid sequence of ARDKGYYFDY (SEQ ID NO: 26); and an LCDR1 comprising an amino acid sequence of QSVGNRY (SEQ ID NO: 27), an LCDR2 comprising an amino acid sequence of GAS (SEQ ID NO: 28), an LCDR3 comprising an amino acid sequence of QQDYNLPLT (SEQ ID NO:29);

(c) an HCDR1 comprising an amino acid sequence of GFTFSSYG (SEQ ID NO: 73), an HCDR2 comprising an amino acid sequence of ISYDGSDK (SEQ ID NO: 25), an HCDR3 comprising an amino acid sequence of ARDGSRYFDY (SEQ ID NO: 30); and an LCDR1 comprising an amino acid sequence of QSVHSKY (SEQ ID NO: 31), an LCDR2 comprising an amino acid sequence of GAS (SEQ ID NO: 28), an LCDR3 comprising an amino acid sequence of QQDYNLPIT (SEQ ID NO: 32); or (d) an HCDR1 comprising an amino acid sequence of GGSISSSTYY (SEQ ID NO: 33), an HCDR2 comprising an amino acid sequence of THYRGST (SEQ ID NO: 34), an HCDR3 comprising an amino acid sequence of ARELTGEVFDY (SEQ ID NO: 35); and an LCDR1 comprising an amino acid sequence of QSISSY (SEQ ID NO:36), an LCDR2 comprising an amino acid sequence of AAS (SEQ ID NO: 23), an LCDR3 comprising an amino acid sequence of QQSYSTPFT (SEQ ID NO: 37);

(e) an HCDR1 comprising an amino acid sequence of GGSISTYY (SEQ ID NO: 19), an HCDR2 comprising an amino acid sequence of IYFSGST (SEQ ID NO: 38), and HCDR3 comprising an amino acid sequence of AREDYYGSGSPEDY (SEQ ID NO:21); and an LCDR1 comprising an amino acid sequence of QGIRND (SEQ ID NO: 39), an LCDR2 comprising an amino acid sequence of AAS (SEQ ID NO: 23), an LCDR3 comprising an amino acid sequence of LQDYNYPRT (SEQ ID NO:40);

(f) an HCDR1 comprising an amino acid sequence of GGSISTDY (SEQ ID NO:41), an HCDR2 comprising an amino acid sequence of IYFSGST (SEQ ID NO:38), and HCDR3 comprising an amino acid sequence of AREDYYGSGSPFDY (SEQ ID NO:21); and an LCDR1 comprising an amino acid sequence of QDIRND (SEQ ID NO:42), an LCDR2 comprising an amino acid sequence of AAS (SEQ ID NO: 23), an LCDR3 comprising an amino acid sequence of LQDYNFPRT (SEQ ID NO: 24);

(g) an HCDR1 comprising an amino acid sequence of GFTFSSYG (SEQ ID NO: 73), an HCDR2 comprising an amino acid sequence of ISYDGSDK (SEQ ID NO:25), and HCDR3 comprising an amino acid sequence of ARDGQFYFDY (SEQ ID NO: 43); and an LCDR1 comprising an amino acid sequence of QSVTSRY (SEQ ID NO:44), an LCDR2 comprising an amino acid sequence of GAS (SEQ ID NO:28), an LCDR3 comprising an amino acid sequence of QQDYNLPLT (SEQ ID NO:29);

(h) an HCDR1 comprising an amino acid sequence of GFTFSNYG (SEQ ID NO: 45), an HCDR2 comprising an amino acid sequence of ISYDGSDK (SEQ ID NO: 25), and HCDR3 comprising an amino acid sequence of ARDSGRYFFDY (SEQ ID NO:46); and an LCDR1 comprising an amino acid sequence of QSVSSRS (SEQ ID NO:47), an LCDR2 comprising an amino acid sequence of GPS (SEQ ID NO: 48), an LCDR3 comprising an amino acid sequence of HQDYNLPLT (SEQ ID NO:49); or (i) an HCDR1 comprising an amino acid sequence of GFTFSKYG (SEQ ID NO: 50), an HCDR2 comprising an amino acid sequence of IWYDGSIK (SEQ ID NO: 51), and HCDR3 comprising an amino acid sequence of ARGSLWFGEFYFDY (SEQ ID NO: 52); and an LCDR1 comprising an amino acid sequence of QGISSA (SEQ ID NO: 53), an LCDR2 comprising an amino acid sequence of DAS (SEQ ID NO: 54), an LCDR3 comprising an amino acid sequence of QQFN-NYPRT (SEQ ID NO: 55).

In some embodiments, the anti-Clec12A antibody or antigen-binding fragment thereof is selected from the group consisting of an IgA antibody, IgG antibody, IgE antibody, IgM antibody, bi- or multi-specific antibody, Fab fragment, Fab' fragment, F(ab')2 fragment, Fd' fragment, Fd fragment, isolated CDRs or sets thereof; single-chain variable fragment (scFv), polypeptide-Fc fusion, single domain antibody, cameloid antibody; masked antibody, Small Modular Immu-noPharmaceutical ("SMIPs™"), single chain, Tandem dia-body, VHHs, Anticalin, Nanobody, minibodies, BiTE, ankyrin repeat protein, DARPIN, Avimer, DART, TCR-like antibody, Adnectin, Affilin, Trans-body; Affibody, TrimerX, MicroProtein, Fynomer, Centyrin; and KALBITOR.

In some embodiments, the anti-Clec12A antibody or antigen-binding fragment thereof is a monoclonal antibody or a single-chain variable fragment (scFv).

In some embodiments, the anti-Clec12A antibody is an antibody comprising an IgG constant region.

In some embodiments, the anti-Clec12A antigen-binding fragment thereof is a single-chain variable fragment (scFv).

In some embodiments, the scFv comprises a leader sequence, a heavy chain variable sequence, a GS-Linker, and a light chain variable sequence.

In some embodiments, the scFv comprises a sequence consisting of an amino acid sequence that is at least about 80% identity to:

```
(a)
                                 (SEQ ID NO: 56)
QVQLQESGPGLVKPSETLSLTCTVSGGSISTYYWSWIRQPPGKGLEWIGY

IYYSGSTKYNPSLKSRVTISVDTSKNLFSLKLSSVTAADTAVYYCAREDY

YGSGSPFDYWGQGTLVTVSSASTGGGGSGGGGSGGGGSAIQMTQSPSSLS

ASVGDRVTITCRASQGIRYDLGWYQQKPGKAPKLLIYAASSLQSGVPSRF

SGSGSGTDFTLTISSLQPEDFATYYCLQDYNFPRTFGQGTKVEIK;

(b)
                                 (SEQ ID NO: 57)
QVQLVESGGGVVQPGRSLRLSCAASGFTFSSYGMHWVRQAPGKGLEWVAI

VISYDGSDKYYVDSVKGRFTISRDNSKNTLYLHMNSLRAEDTAVYYCARD

KGYYFDYWGQGTLVTVSSASTGGGGSGGGGSGGGGSEIVMTQSPATLSLS
```

-continued

```
PGERATLSCRASQSVGNRYLSWYQQKPGQAPRLLIYGASTRATGIPARFS

GSGSGTDFTLTISSLQPEDFAVYYCQQDYNLPLTFGGGTKVEIK;

(c)
                                 (SEQ ID NO: 58)
QVQLVESGGGVVQPGRSLRLSCAASGFTFSSYGMHWVRQAPGKGLEWVAV

ISYDGSDKYSADSVKGRFNISRDNSKNTLYLQMNSLRAEDTAVYYCARDG

SRYFDYWGQGTLVTVSSASTGGGGSGGGGSGGGGSEIFMTQSPATLSLPG

ERATLSCRASQSVHSKYLSWYQQKPGQAPSLLIYGASTRATGIPARFSGS

GSGTDFTLTISSLQPEDFAVYYCQQDYNLPITFGQGTRLEIK;
or (d)
                                 (SEQ ID NO: 59)
QLQLQESGPGLVKPSETLSLTCTVSGGSISSSTYYWGWIRQPPRKGLEWI

GSTHYRGSTYYNPSLKSRVTISVDTSKNQFSLKVSSVTAADTAVYYCARE

LTGEVFDYWGQGTLVTVSSASTGGGGSGGGGSGGGGSDIQMTQSPSSLSA

SVGDRVTITCRASQSISSYLNWYQQKPGKAPKLLIYAASSLQSGVPSRFS

GSGSGTDFTLTISSLQPEDFATYYCQQSYSTPFTFGPGTKVDIK.
```

In some embodiments, the scFv comprises an amino acid sequence of:

```
(a)
                                 (SEQ ID NO: 56)
QVQLQESGPGLVKPSETLSLTCTVSGGSISTYYWSWIRQPPGKGLEWIGY

IYYSGSTKYNPSLKSRVTISVDTSKNLFSLKLSSVTAADTAVYYCAREDY

YGSGSPFDYWGQGTLVTVSSASTGGGGSGGGGSGGGGSAIQMTQSPSSLS

ASVGDRVTITCRASQGIRYDLGWYQQKPGKAPKLLIYAASSLQSGVPSRF

SGSGSGTDFTLTISSLQPEDFATYYCLQDYNFPRTFGQGTKVEIK;

(b)
                                 (SEQ ID NO: 57)
QVQLVESGGGVVQPGRSLRLSCAASGFTFSSYGMHWVRQAPGKGLEWVAI

VISYDGSDKYYVDSVKGRFTISRDNSKNTLYLHMNSLRAEDTAVYYCARD

KGYYFDYWGQGTLVTVSSASTGGGGSGGGGSGGGGSEIVMTQSPATLSLS

PGERATLSCRASQSVGNRYLSWYQQKPGQAPRLLIYGASTRATGIPARFS

GSGSGTDFTLTISSLQPEDFAVYYCQQDYNLPLTFGGGTKVEIK;

(c)
                                 (SEQ ID NO: 58)
QVQLVESGGGVVQPGRSLRLSCAASGFTFSSYGMHWVRQAPGKGLEWVAV

ISYDGSDKYSADSVKGRFNISRDNSKNTLYLQMNSLRAEDTAVYYCARDG

SRYFDYWGQGTLVTVSSASTGGGGSGGGGSGGGGSEIFMTQSPATLSLPG

ERATLSCRASQSVHSKYLSWYQQKPGQAPSLLIYGASTRATGIPARFSGS

GSGTDFTLTISSLQPEDFAVYYCQQDYNLPITFGQGTRLEIK;
or (d)
                                 (SEQ ID NO: 59)
QLQLQESGPGLVKPSETLSLTCTVSGGSISSSTYYWGWIRQPPRKGLEWI

GSTHYRGSTYYNPSLKSRVTISVDTSKNQFSLKVSSVTAADTAVYYCARE

LTGEVFDYWGQGTLVTVSSASTGGGGSGGGGSGGGGSDIQMTQSPSSLSA
```

-continued

SVGDRVTITCRASQSISSYLNWYQQKPGKAPKLLIYAASSLQSGVPSRFS

GSGSGTDFTLTISSLQPEDFATYYCQQSYSTPFTFGPGTKVDIK.

In some embodiments, the anti-Clec12A antibody or
antigen-binding fragmthere thereof binds to Clec12A with a
disassociation constant ($K_D$) of less than about $10^{-8}$ M, less
than about $10^{-9}$ M, less than about $10^{-10}$ M, less than about
$10^{-11}$ M, less than about $10^{-12}$ M, or less than about $10^{-13}$
M.

In some embodiments, the $K_D$ is 0.1 pM or below.

In some embodiments, the $K_D$ is between 0.05 and 0.5
pM.

In some embodiments, the $K_D$ is between about 0.1 nM
and 5.0 nM.

In some embodiments, the $K_D$ is between about 0.3 nM
and 3.5 nM.

In some embodiments, the EC50 is between about 1 and
about 100 nM.

In some aspects, a method of treating a cancer is provided,
comprising administering the anti-Clec12A antibody or anti-
gen-binding fragment thereof described herein.

In some embodiments, the cancer is selected from leuke-
mia, lymphoma, and myeloma.

In some aspects, a pharmaceutical composition is pro-
vided comprising anti-Clec12A antibody or antigen-binding
fragment thereof and a pharmaceutically acceptable carrier,
wherein the anti-Clec12A antibody or antigen-binding frag-
ment thereof comprises: (a) an immunoglobulin heavy chain
variable (VH) region comprising an amino acid sequence
that is at least about 80% identical to (SEQ ID NO: 1)
QVQLQESGPGLVKPSETLSLTCTVSGGSISTYYWSWIRQPPGKGLEWIGY

IYYSGSTKYNPSLKSRVTISVDTSKNLFSLKLSSVTAADTAVYYCAREDY

YGSGSPFDYWGQGTLVTVSS,
and an immunoglobulin light chain variable (VL) region com-
prising an amino acid sequence that is at least about
80% identical to (SEQ ID NO: 2)
IQMTQSPSSLSASVGDRVTITCRASQGIRYDLGWYQQKPGKAPKLLIYAA

SSLQSGVPSRFSGSGSGTDFTLTISSLQPEDFATYYCLQDYNFPRTFGQG

TKVEIK;

(b) an immunoglobulin heavy chain variable (VH) region
comprising an amino acid sequence that is at least
about 80% identical to (SEQ ID NO: 3)
QVQLVESGGGVVQPGRSLRLSCAASGFTFSSYGMHWVRQAPGKGLEWVAV

ISYDGSDKYYVDSVKGRFTISRDNSKNTLYLHMNSLRAEDTAVYYCARDK

GYYFDYWGQGTLVTVSS,
and an immunoglobulin light chain variable (VL) region com-
prising an amino acid sequence that is at least about
80% identical to (SEQ ID NO: 4)
ETVMTQSPATLSLSPGERATLSCRASQSVGNRYLSWYQQKPGQAPRLLIY

GASTRATGIPARFSGSGSGTDFTLTISSLQPEDFAVYYCQQDYNLPLTFG

GGTKVEIK;

(c) an immunoglobulin heavy chain variable (VH) region
comprising an amino acid sequence that is at least
about 80% identical to (SEQ ID NO: 5)
QVQLVESGGGVVQPGRSLRLSCAASGFTFSSYGMHWVRQAPGKGLEWVAV

ISYDGSDKYSADSVKGRFNISRDNSKNTLYLQMNSLRAEDTAVYYCARDG

SRYFDYWGQGTLVTVSS,
and an immunoglobulin light chain variable (VL) region com-
prising an amino acid sequence that is at least about
80% identical to (SEQ ID NO: 6)
EIFMTQSPATLSLSPGERATLSCRASQSVHSKYLSWYQQKPGQAPSLLIY

GASTRATGIPARFSGSGSGTDFTLTISSLQPEDFAVYYCQQDYNLPITFG

QGTRLEIK;
or (d) an immunoglobulin heavy chain variable (VH) region
comprising an amino acid sequence that is at least
about 80% identical to (SEQ ID NO: 7)
QLQLQESGPGLVKPSETLSLTCTVSGGSISSSTYYWGWIRQPPRKGLEWI

GSTHYRGSTYYNPSLKSRVTISVDTSKNQFSLKVSSVTAADTAVYYCARE

LTGEVFDYWGQGTLVTVSS,
and an immunoglobulin light chain variable (VL) region com-
prising an amino acid sequence that is at least about
80% identical to (SEQ ID NO: 8)
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPFTFGP

GTKVDIK;

(e) an immunoglobulin heavy chain variable (VH) region
comprising an amino acid sequence that is at least
about 80% identical to (SEQ ID NO: 9)
QVQLQESGPGLVKPSETLSLTCTVSGGSISTYYWSWIRQPPGKGLEWLGY

IYFSGSTNYNPSLKSRLTISVAASKSQFSLKLSSVTAADTAVYYCAREDY

YGSGSPFDYWGQGTLVTVSS,
and an immunoglobulin light variable (VL) region comprising
an amino acid sequence that is at least about 80%
identical to an immunoglobulin light variable (VL) region comprising an amino acid sequence that is at least about 80% identical to (SEQ ID NO: 10)
AIQMTQSPSSLSASVGDRVTITCRASQGIRNDLGWFQQKPGKAPKLLIYA

ASSLQSGVPSRFSGSGSGTYFTLTISSLQPEDSATYYCLQDYNYPRTFGQ

GTKVEIK;

(f) an immunoglobulin heavy chain variable (VH) region comprising an amino acid sequence that is at least about 80% identical to (SEQ ID NO: 11)
QVQLQESGPGLVKPSETLSLTCTVSGGSISTDYWSWIRQPPGKGLEWIGY

IYFSGSTKYNPSLKSRVTISVDTSKNQFSLKLSSVTAADTAVYYCAREDY

YGSGSPFDYWGQGTLVTVSS,
and an immunoglobulin light variable (VL) region comprising an amino acid sequence that is at least about 80% identical to (SEQ ID NO: 12)
AIQMTQSPSSLSASVGDRVTITCRASQDIRNDLGWFQQKPGKAPKLLIYA

ASSLQSGVPSRFSGSGSGTDFTLTISSLQPEDFATYYCLQDYNFPRTFGQ

GTKVEIK;

(g) an immunoglobulin heavy chain variable (VH) region comprising an amino acid sequence that is at least about 80% identical to (SEQ ID NO: 13)
QVQLVESGGGVVQPGRSLRLSCAASGFTFSSYGMHWVRQAPGEGLEWVTV

ISYDGSDKYYADSVKGRFTISRDNSKSTLFLQMNSLRAEDTAVYYCARDG

QFYFDYWGQGTLVTVSS,
and an immunoglobulin light variable (VL) region comprising an amino acid sequence that is at least about 80% identical to (SEQ ID NO: 14)
EIVMTQSPATLSLSPGESATLSCRASQSVTSRYLSWYQQKPGQAPRLLMY

GASTRPTGIPARFSGSGSGTDFTLTISSLQPEDFAVYYCQQDYNLPLTFG

GGTKVEIK;

(h) an immunoglobulin heavy chain variable (VH) region comprising an amino acid sequence that is at least about 80% identical to (SEQ ID NO: 15)
QVQLVESGGGVVQPGRSLRLSCAASGFTFSNYGMHWVRQAPGKGLEWVAV

ISYDGSDKSYKDSVKGRFTIARDNSKNTLYLQMNSLRAEDTAVYYCARDS

GRYFFDYWGQGTLVTVSS,
and an immunoglobulin light variable (VL) region comprising an amino acid sequence that is at least about 80% identical to (SEQ ID NO: 16)
EIIMTQSPATLSLSPGERATLSCRASQSVSSRSLSWYQHKPGQAPRLLIY

GPSTRATGIPARFSGSGSGTDFTLTISSLQPEDFAVYYCHQDYNLPLTFG

GGTKVEIK;
or (i) an immunoglobulin heavy chain variable (VH) region comprising an amino acid sequence that is at least about 80% identical to (SEQ ID NO: 17)
QVKLVESGGGVVQPGRSLRLSCAASGFTFSKYGMHWVRQAPGKGLEWVAF

IWYDGSIKNYADSVKGRFTTSRDNSKNTLYLQMNSLRAEDTAVYYCARGS

LWFGEFYFDYWGQGTLVTVSS,
and an immunoglobulin light variable (VL) region comprising an amino acid sequence that is at least about 80% identical to (SEQ ID NO: 18)
AIQLTQSPSSLSASVGDRVTITCRTSQGISSALAWYQQKPGKTPKLLIYD

ASSLESGVPSRFSGSGSGTDFTLTISSLQPEDFATYYCQQFNNYPRTFGQ

GTKVEIK.

In some embodiments, the pharmaceutical composition comprises an anti-Clec12a antibody or antigen-binding fragment thereof that comprises:
(a) an immunoglobulin heavy chain variable (VH) region comprising an amino acid sequence of (SEQ ID NO: 1)
QVQLQESGPGLVKPSETLSLTCTVSGGSISTYYWSWIRQPPGKGLEWIGY

IYYSGSTKYNPSLKSRVTISVDTSKNLFSLKLSSVTAADTAVYYCAREDY

YGSGSPFDYWGQGTLVTVSS,
and an immunoglobulin light chain variable (VL) region comprising an amino acid sequence of (SEQ ID NO: 2)
IQMTQSPSSLSASVGDRVTITCRASQGIRYDLGWYQQKPGKAPKLLIYAA

SSLQSGVPSRFSGSGSGTDFTLTISSLQPEDFATYYCLQDYNFPRTFGQG

TKVEIK;

(b) an immunoglobulin heavy chain variable (VH) region comprising an amino acid sequence of (SEQ ID NO: 3)
QVQLVESGGGVVQPGRSLRLSCAASGFTFSSYGMHWVRQAPGKGLEWVAV

ISYDGSDKYYVDSVKGRFTISRDNSKNTLYLHMNSLRAEDTAVYYCARDK

GYYFDYWGQGTLVTVSS,
and an immunoglobulin light chain variable (VL) region com-
prising an amino acid sequence of (SEQ ID NO: 4)
EIVMTQSPATLSLSPGERATLSCRASQSVGNRYLSWYQQKPGQAPRLLIY

GASTRATGIPARFSGSGSGTDFTLTISSLQPEDFAVYYCQQDYNLPLTFG

GGTKVEIK;

(c) an immunoglobulin heavy chain variable (VH) region
comprising an amino acid sequence of 80% identical (SEQ ID NO: 5)
QVQLVESGGGVVQPGRSLRLSCAASGFTFSSYGMHWVRQAPGKGLEWVAV

ISYDGSDKYSADSVKGRFNISRDNSKNTLYLQMNSLRAEDTAVYYCARDG

SRYFDYWGQGTLVTVSS,
and an immunoglobulin light chain variable (VL) region com-
prising an amino acid sequence of (SEQ ID NO: 6)
EIFMTQSPATLSLSPGERATLSCRASQSVHSKYLSWYQQKPGQAPSLLIY

GASTRATGIPARFSGSGSGTDFTLTISSLQPEDFAVYYCQQDYNLPITFG

QGTRLEIK;
or (d) an immunoglobulin heavy chain variable (VH) region
comprising an amino acid sequence of (SEQ ID NO: 7)
QLQLQESGPGLVKPSETLSLTCTVSGGSISSSTYYWGWIRQPPRKGLEWI

GSTHYRGSTYYNPSLKSRVTISVDTSKNQFSLKVSSVTAADTAVYYCARE

LTGEVFDYWGQGTLVTVSS,
and an immunoglobulin light chain variable (VL) region com-
prising an amino acid sequence of (SEQ ID NO: 8)
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPFTFGP

GTKVDIK;

(e) an immunoglobulin heavy chain variable (VH) region
comprising an amino acid sequence of (SEQ ID NO: 9)
QVQLQESGPGLVKPSETLSLTCTVSGGSISTYYWSWIRQPPGKGLEWLGY

IYFSGSTNYNPSLKSRLTISVAASKSQFSLKLSSVTAADTAVYYCAREDY

YGSGSPFDYWGQGTLVTVSS,
and an immunoglobulin light variable (VL) region comprising
an amino acid sequence of (SEQ ID NO: 10)
AIQMTQSPSSLSASVGDRVTITCRASQGIRNDLGWFQQKPGKAPKLLIYA

ASSLQSGVPSRFSGSGSGTYFTLTISSLQPEDSATYYCLQDYNYPRTFGQ

GTKVEIK;

(f) an immunoglobulin heavy chain variable (VH) region
comprising an amino acid sequence of (SEQ ID NO: 11)
QVQLQESGPGLVKPSETLSLTCTVSGGSISTDYWSWIRQPPGKGLEWIGY

IYFSGSTKYNPSLKSRVTISVDTSKNQFSLKLSSVTAADTAVYYCAREDY

YGSGSPFDYWGQGTLVTVSS,
and an immunoglobulin light variable (VL) region comprising
an amino acid sequence of (SEQ ID NO: 12)
AIQMTQSPSSLSASVGDRVTITCRASQDIRNDLGWFQQKPGKAPKLLIY

AASSLQSGVPSRFSGSGSGTDFTLTISSLQPEDFATYYCLQDYNFPRTF

GQGTKVEIK;

(g) an immunoglobulin heavy chain variable (VH) region
comprising an amino acid sequence of (SEQ ID NO: 13)
QVQLVESGGGVVQPGRSLRLSCAASGFTFSSYGMHWVRQAPGEGLEWVTV

ISYDGSDKYYADSVKGRFTISRDNSKSTLFLQMNSLRAEDTAVYYCARDG

QFYFDYWGQGTLVTVSS,
and an immunoglobulin light variable (VL) region comprising
an amino acid sequence of (SEQ ID NO: 14)
EIVMTQSPATLSLSPGESATLSCRASQSVTSRYLSWYQQKPGQAPRLLMY

GASTRPTGIPARFSGSGSGTDFTLTISSLQPEDFAVYYCQQDYNLPLTFG

GGTKVEIK;

(h) an immunoglobulin heavy chain variable (VH) region
comprising an amino acid sequence of (SEQ ID NO: 15)
QVQLVESGGGVVQPGRSLRLSCAASGFTFSNYGMHWVRQAPGKGLEWVAV

ISYDGSDKSYKDSVKGRFTIARDNSKNTLYLQMNSLRAEDTAVYYCARDS

GRYFFDYWGQGTLVTVSS,
and an immunoglobulin light variable (VL) region comprising an amino acid sequence of

```
                              (SEQ ID NO: 16)
EIIMTQSPATLSLSPGERATLSCRASQSVSSRSLSWYQHKPGQAPRLLIY

GPSTRATGIPARFSGSGSGTDFTLTISSLQPEDFAVYYCHQDYNLPLTFG

GGTKVEIK;
or
```

(i) an immunoglobulin heavy chain variable (VH) region comprising an amino acid sequence of

```
                              (SEQ ID NO: 17)
QVKLVESGGGVVQPGRSLRLSCAASGFTFSKYGMHWVRQAPGKGLEWVAF

IWYDGSIKNYADSVKGRFTTSRDNSKNTLYLQMNSLRAEDTAVYYCARGS

LWFGEFYFDYWGQGTLVTVSS,
and
``` an immunoglobulin light variable (VL) region comprising an amino acid sequence of

```
                              (SEQ ID NO: 18)
AIQLTQSPSSLSASVGDRVTITCRTSQGISSALAWYQQKPGKTPKLLIYD

ASSLESGVPSRFSGSGSGTDFTLTISSLQPEDFATYYCQQFNNYPRTFGQ

GTKVEIK.
```

In some embodiments, the pharmaceutical composition comprises an anti-Clec 12a antibody or antigen-binding fragment thereof comprising:

(a) a heavy chain complementarity determining region (HCDR) 1 comprising an amino acid sequence of GGSISTYY (SEQ ID NO: 19), an HCDR2 comprising an amino acid sequence of IYYSGST (SEQ ID NO: 20), an HCDR3 comprising an amino acid sequence of AREDYYGSGSPFDY (SEQ ID NO: 21); and a light chain complementarity determining region (LCDR) 1 comprising an amino acid sequence of QGIRYD (SEQ ID NO: 22), an LCDR2 comprising an amino acid sequence of AAS (SEQ ID NO:23), and an LCDR3 comprising an amino acid sequence of LQDYNFPRT (SEQ ID NO: 24);

(b) an HCDR1 comprising an amino acid sequence of GFTFSSYG (SEQ ID NO: 73), an HCDR2 comprising an amino acid sequence of ISYDGSDK (SEQ ID NO: 25), and HCDR3 comprising an amino acid sequence of ARDKGYYFDY (SEQ ID NO: 26); and an LCDR1 comprising an amino acid sequence of QSVGNRY (SEQ ID NO: 27), an LCDR2 comprising an amino acid sequence of GAS (SEQ ID NO: 28), an LCDR3 comprising an amino acid sequence of QQDYNLPLT (SEQ ID NO:29);

(c) an HCDR1 comprising an amino acid sequence of GFTFSSYG (SEQ ID NO: 73), an HCDR2 comprising an amino acid sequence of ISYDGSDK (SEQ ID NO: 25), an HCDR3 comprising an amino acid sequence of ARDGSRYFDY (SEQ ID NO: 30); and an LCDR1 comprising an amino acid sequence of QSVHSKY (SEQ ID NO: 31), an LCDR2 comprising an amino acid sequence of GAS (SEQ ID NO: 28), an LCDR3 comprising an amino acid sequence of QQDYNLPIT (SEQ ID NO: 32); or (d) an HCDR1 comprising an amino acid sequence of GGSISSSTYY (SEQ ID NO: 33), an HCDR2 comprising an amino acid sequence of THYRGST (SEQ ID NO: 34), an HCDR3 comprising an amino acid sequence of ARELTGEVFDY (SEQ ID NO: 35); and an LCDR1 comprising an amino acid sequence of QSISSY (SEQ ID NO:36), an LCDR2 comprising an amino acid sequence of AAS (SEQ ID NO: 23), an LCDR3 comprising an amino acid sequence of QQSYSTPFT (SEQ ID NO: 37);

(e) an HCDR1 comprising an amino acid sequence of GGSISTYY (SEQ ID NO: 19), an HCDR2 comprising an amino acid sequence of IYFSGST (SEQ ID NO: 38), and HCDR3 comprising an amino acid sequence of AREDYYGSGSPEDY (SEQ ID NO:21); and an LCDR1 comprising an amino acid sequence of QGIRND (SEQ ID NO: 39), an LCDR2 comprising an amino acid sequence of AAS (SEQ ID NO: 23), an LCDR3 comprising an amino acid sequence of LQDYNYPRT (SEQ ID NO:40);

(f) an HCDR1 comprising an amino acid sequence of GGSISTDY (SEQ ID NO:41), an HCDR2 comprising an amino acid sequence of IYFSGST (SEQ ID NO:38), and HCDR3 comprising an amino acid sequence of AREDYYGSGSPFDY (SEQ ID NO:21); and an LCDR1 comprising an amino acid sequence of QDIRND (SEQ ID NO:42), an LCDR2 comprising an amino acid sequence of AAS (SEQ ID NO: 23), an LCDR3 comprising an amino acid sequence of LQDYNFPRT (SEQ ID NO: 24);

(g) an HCDR1 comprising an amino acid sequence of GFTFSSYG (SEQ ID NO: 73), an HCDR2 comprising an amino acid sequence of ISYDGSDK (SEQ ID NO:25), and HCDR3 comprising an amino acid sequence of ARDGQFYFDY (SEQ ID NO: 43); and an LCDR1 comprising an amino acid sequence of QSVTSRY (SEQ ID NO:44), an LCDR2 comprising an amino acid sequence of GAS (SEQ ID NO:28), an LCDR3 comprising an amino acid sequence of QQDYNLPLT (SEQ ID NO:29);

(h) an HCDR1 comprising an amino acid sequence of GFTFSNYG (SEQ ID NO: 45), an HCDR2 comprising an amino acid sequence of ISYDGSDK (SEQ ID NO: 25), and HCDR3 comprising an amino acid sequence of ARDSGRYFFDY (SEQ ID NO:46); and an LCDR1 comprising an amino acid sequence of QSVSSRS (SEQ ID NO:47), an LCDR2 comprising an amino acid sequence of GPS (SEQ ID NO: 48), an LCDR3 comprising an amino acid sequence of HQDYNLPLT (SEQ ID NO:49); or (i) an HCDR1 comprising an amino acid sequence of GFTFSKYG (SEQ ID NO: 50), an HCDR2 comprising an amino acid sequence of IWYDGSIK (SEQ ID NO: 51), and HCDR3 comprising an amino acid sequence of ARGSLWFGEFYFDY (SEQ ID NO: 52); and an LCDR1 comprising an amino acid sequence of QGISSA (SEQ ID NO: 53), an LCDR2 comprising an amino acid sequence of DAS (SEQ ID NO: 54), an LCDR3 comprising an amino acid sequence of QQFN-NYPRT (SEQ ID NO: 55).

In some embodiments, the pharmaceutical composition comprises an anti-Clec12A antibody or antigen-binding fragment thereof selected from the group consisting of an IgA antibody, IgG antibody, IgE antibody, IgM antibody, bi- or multi-specific antibody, Fab fragment, Fab' fragment, F(ab')2 fragment, Fd' fragment, Fd fragment, isolated CDRs or sets thereof; single-chain variable fragment (scFv), poly-peptide-Fc fusion, single domain antibody, cameloid anti-body; masked antibody, Small Modular ImmunoPharmaceutical ("SMIPs™"), single chain, Tandem diabody, VHHs, Anticalin, Nanobody, minibodies, BiTE, ankyrin repeat protein, DARPIN, Avimer, DART, TCR-like antibody, Adnectin, Affilin, Trans-body; Affibody, TrimerX, MicroProtein, Fynomer, Centyrin; and KALBITOR.

In some embodiments, the pharmaceutical composition comprises an anti-Clec12A antibody or antigen-binding fragment as a monoclonal antibody or a single-chain variable fragment (scFv).

In some embodiments, the anti-Clec12A antibody is an antibody comprising an IgG constant region.

In some embodiments, the anti-Clec12A antigen-binding fragment thereof is a single-chain variable fragment (scFv).

In some embodiments, the scFv comprises a leader sequence, a heavy chain variable sequence, a GS-Linker, and a light chain variable sequence.

In some embodiments, the pharmaceutical composition as described herein comprises an scFv comprising a sequence having an amino acid sequence that is at least about 80% identity to:

(a)
```
                               (SEQ ID NO: 56)
QVQLQESGPGLVKPSETLSLTCTVSGGSISTYYWSWIRQPPGKGLEWIGY

IYYSGSTKYNPSLKSRVTISVDTSKNLFSLKLSSVTAADTAVYYCAREDY

YGSGSPFDYWGQGTLVTVSSASTGGGGSGGGGSGGGGSAIQMTQSPSSLS

ASVGDRVTITCRASQGIRYDLGWYQQKPGKAPKLLIYAASSLQSGVPSRF

SGSGSGTDFTLTISSLQPEDFATYYCLQDYNFPRTFGQGTKVEIK;
```

(b)
```
                               (SEQ ID NO: 57)
QVQLVESGGGVVQPGRSLRLSCAASGFTFSSYGMHWVRQAPGKGLEWVAI

VISYDGSDKYYVDSVKGRFTISRDNSKNTLYLHMNSLRAEDTAVYYCARD

KGYYFDYWGQGTLVTVSSASTGGGGSGGGGSGGGGSEIVMTQSPATLSLS

PGERATLSCRASQSVGNRYLSWYQQKPGQAPRLLIYGASTRATGIPARES

GSGSGTDFTLTISSLQPEDFAVYYCQQDYNLPLTFGGGTKVEIK;
```

(c)
```
                               (SEQ ID NO: 58)
QVQLVESGGGVVQPGRSLRLSCAASGFTFSSYGMHWVRQAPGKGLEWVAV

ISYDGSDKYSADSVKGRFNISRDNSKNTLYLQMNSLRAEDTAVYYCARDG

SRYFDYWGQGTLVTVSSASTGGGGSGGGGSGGGGSEIFMTQSPATLSLPG

ERATLSCRASQSVHSKYLSWYQQKPGQAPSLLIYGASTRATGIPARFSGS

GSGTDFTLTISSLQPEDFAVYYCQQDYNLPITFGQGTRLEIK;
or
```

(d)
```
                               (SEQ ID NO: 59)
QLQLQESGPGLVKPSETLSLTCTVSGGSISSSTYYWGWIRQPPRKGLEWI

GSTHYRGSTYYNPSLKSRVTISVDTSKNQFSLKVSSVTAADTAVYYCARE

LTGEVFDYWGQGTLVTVSSASTGGGGSGGGGSGGGGSDIQMTQSPSSLSA

SVGDRVTITCRASQSISSYLNWYQQKPGKAPKLLIYAASSLQSGVPSRFS

GSGSGTDFTLTISSLQPEDFATYYCQQSYSTPFTFGPGTKVDIK.
```

In some embodiments, the pharmaceutical composition comprises an scFv comprising a sequence of:

(a)
```
                               (SEQ ID NO: 56)
QVQLQESGPGLVKPSETLSLTCTVSGGSISTYYWSWIRQPPGKGLEWIGY

IYYSGSTKYNPSLKSRVTISVDTSKNLFSLKLSSVTAADTAVYYCAREDY

YGSGSPFDYWGQGTLVTVSSASTGGGGSGGGGSGGGGSAIQMTQSPSSLS

ASVGDRVTITCRASQGIRYDLGWYQQKPGKAPKLLIYAASSLQSGVPSRF

SGSGSGTDFTLTISSLQPEDFATYYCLQDYNFPRTFGQGTKVEIK;
```

(b)
```
                               (SEQ ID NO: 57)
QVQLVESGGGVVQPGRSLRLSCAASGFTFSSYGMHWVRQAPGKGLEWVAI

VISYDGSDKYYVDSVKGRFTISRDNSKNTLYLHMNSLRAEDTAVYYCARD

KGYYFDYWGQGTLVTVSSASTGGGGSGGGGSGGGGSEIVMTQSPATLSLS

PGERATLSCRASQSVGNRYLSWYQQKPGQAPRLLIYGASTRATGIPARFS

GSGSGTDFTLTISSLQPEDFAVYYCQQDYNLPLTFGGGTKVEIK;
```

(c)
```
                               (SEQ ID NO: 58)
QVQLVESGGGVVQPGRSLRLSCAASGFTFSSYGMHWVRQAPGKGLEWVAV

ISYDGSDKYSADSVKGRFNISRDNSKNTLYLQMNSLRAEDTAVYYCARDG

SRYFDYWGQGTLVTVSSASTGGGGSGGGGSGGGGSEIFMTQSPATLSLPG

ERATLSCRASQSVHSKYLSWYQQKPGQAPSLLIYGASTRATGIPARFSGS

GSGTDFTLTISSLQPEDFAVYYCQQDYNLPITFGQGTRLEIK;
or
```

(d)
```
                               (SEQ ID NO: 59)
QLQLQESGPGLVKPSETLSLTCTVSGGSISSSTYYWGWIRQPPRKGLEWI

GSTHYRGSTYYNPSLKSRVTISVDTSKNQFSLKVSSVTAADTAVYYCARE

LTGEVFDYWGQGTLVTVSSASTGGGGSGGGGSGGGGSDIQMTQSPSSLSA

SVGDRVTITCRASQSISSYLNWYQQKPGKAPKLLIYAASSLQSGVPSRFS

GSGSGTDFTLTISSLQPEDFATYYCQQSYSTPFTFGPGTKVDIK.
```

In some embodiments, a nucleic acid sequence is provided encoding an amino acid sequence that is at least about 90% identical to any one of SEQ ID NO: 1-59.

In some embodiments, a vector is provided comprising the nucleic acid encoding an amino acid sequence that is at least about 90% identical to any one of SEQ ID NO: 1-59.

In some embodiments, a cell is provided comprising a vector as described herein.

In some aspects, a method of treating cancer is provided comprising administering an anti-Clec12A antibody or antigen-binding fragment thereof to a subject in need thereof, the anti-Clec12A antibody or antigen-binding fragment thereof comprising:

(a) an immunoglobulin heavy chain variable (VH) region comprising an amino acid sequence of

```
                               (SEQ ID NO: 1)
QVQLQESGPGLVKPSETLSLTCTVSGGSISTYYWSWIRQPPGKGLEWIGY

IYYSGSTKYNPSLKSRVTISVDTSKNLFSLKLSSVTAADTAVYYCAREDY

YGSGSPFDYWGQGTLVTVSS,
```

84B2

21 an immunoglobulin light chain variable (VL) region comprising an amino acid sequence of (SEQ ID NO: 2)
IQMTQSPSSLSASVGDRVTITCRASQGIRYDLGWYQQKPGKAPKLLIYAA

SSLQSGVPSRFSGSGSGTDFTLTISSLQPEDFATYYCLQDYNFPRTFGQG

TKVEIK;

(b) an immunoglobulin heavy chain variable (VH) region comprising an amino acid sequence of (SEQ ID NO: 3)
QVQLVESGGGVVQPGRSLRLSCAASGFTFSSYGMHWVRQAPGKGLEWVAV

ISYDGSDKYYVDSVKGRFTISRDNSKNTLYLHMNSLRAEDTAVYYCARDK

GYYFDYWGQGTLVTVSS,
and an immunoglobulin light chain variable (VL) region comprising an amino acid sequence of (SEQ ID NO: 4)
EIVMTQSPATLSLSPGERATLSCRASQSVGNRYLSWYQQKPGQAPRLLIY

GASTRATGIPARFSGSGSGTDFTLTISSLQPEDFAVYYCQQDYNLPLTFG

GGTKVEIK;

(c) an immunoglobulin heavy chain variable (VH) region comprising an amino acid sequence of (SEQ ID NO: 5)
QVQLVESGGGVVQPGRSLRLSCAASGFTFSSYGMHWVRQAPGKGLEWVAV

ISYDGSDKYSADSVKGRFNISRDNSKNTLYLQMNSLRAEDTAVYYCARDG

SRYFDYWGQGTLVTVSS,
and an immunoglobulin light chain variable (VL) region comprising an amino acid sequence of (SEQ ID NO: 6)
EIFMTQSPATLSLSPGERATLSCRASQSVHSKYLSWYQQKPGQAPSLLIY

GASTRATGIPARFSGSGSGTDFTLTISSLQPEDFAVYYCQQDYNLPITFG

QGTRLEIK;
or (d) an immunoglobulin heavy chain variable (VH) region comprising an amino acid sequence of (SEQ ID NO: 7)
QLQLQESGPGLVKPSETLSLTCTVSGGSISSSTYYWGWIRQPPRKGLEWI

GSTHYRGSTYYNPSLKSRVTISVDTSKNQFSLKVSSVTAADTAVYYCARE

LTGEVFDYWGQGTLVTVSS,
and

22 an immunoglobulin light chain variable (VL) region comprising an amino acid sequence of (SEQ ID NO: 8)
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPFTFGP

GTKVDIK;

(e) an immunoglobulin heavy chain variable (VH) region comprising an amino acid sequence of (SEQ ID NO: 9)
QVQLQESGPGLVKPSETLSLTCTVSGGSISTYYWSWIRQPPGKGLEWLGY

IYFSGSTNYNPSLKSRLTISVAASKSQFSLKLSSVTAADTAVYYCAREDY

YGSGSPFDYWGQGTLVTVSS,
and an immunoglobulin light variable (VL) region comprising an amino acid sequence of (SEQ ID NO: 10)
AIQMTQSPSSLSASVGDRVTITCRASQGIRNDLGWFQQKPGKAPKLLIYA

ASSLQSGVPSRFSGSGSGTYFTLTISSLQPEDSATYYCLQDYNYPRTFGQ

GTKVEIK;

(f) an immunoglobulin heavy chain variable (VH) region comprising an amino acid sequence of (SEQ ID NO: 11)
QVQLQESGPGLVKPSETLSLTCTVSGGSISTDYWSWIRQPPGKGLEWIGY

IYFSGSTKYNPSLKSRVTISVDTSKNQFSLKLSSVTAADTAVYYCAREDY

YGSGSPFDYWGQGTLVTVSS,
and an immunoglobulin light variable (VL) region comprising an amino acid sequence of (SEQ ID NO: 12)
AIQMTQSPSSLSASVGDRVTITCRASQDIRNDLGWFQQKPGKAPKLLIYA

ASSLQSGVPSRFSGSGSGTDFTLTISSLQPEDFATYYCLQDYNFPRTFGQ

GTKVEIK;

(g) an immunoglobulin heavy chain variable (VH) region comprising an amino acid sequence of (SEQ ID NO: 13)
QVQLVESGGGVVQPGRSLRLSCAASGFTFSSYGMHWVRQAPGEGLEWVTV

ISYDGSDKYYADSVKGRFTISRDNSKSTLFLQMNSLRAEDTAVYYCARDG

QFYFDYWGQGTLVTVSS,
and an immunoglobulin light variable (VL) region comprising an amino acid sequence of

```
                                      (SEQ ID NO: 14)
EIVMTQSPATLSLSPGESATLSCRASQSVTSRYLSWYQQKPGQAPRLLMY

GASTRPTGIPARFSGSGSGTDFTLTISSLQPEDFAVYYCQQDYNLPLTFG

GGTKVEIK;
```

(h) an immunoglobulin heavy chain variable (VH) region comprising an amino acid sequence of

```
                                      (SEQ ID NO: 15)
QVQLVESGGGVVQPGRSLRLSCAASGFTFSNYGMHWVRQAPGKGLEWVAV

ISYDGSDKSYKDSVKGRFTIARDNSKNTLYLQMNSLRAEDTAVYYCARDS

GRYFFDYWGQGTLVTVSS,
and
``` an immunoglobulin light variable (VL) region comprising an amino acid sequence of

```
                                      (SEQ ID NO: 16)
EIIMTQSPATLSLSPGERATLSCRASQSVSSRSLSWYQHKPGQAPRLLIY

GPSTRATGIPARFSGSGSGTDFTLTISSLQPEDFAVYYCHQDYNLPLTFG

GGTKVEIK;
or
```

(i) an immunoglobulin heavy chain variable (VH) region comprising an amino acid sequence of

```
                                      (SEQ ID NO: 17)
QVKLVESGGGVVQPGRSLRLSCAASGFTFSKYGMHWVRQAPGKGLEWVAF

IWYDGSIKNYADSVKGRFTTSRDNSKNTLYLQMNSLRAEDTAVYYCARGS

LWFGEFYFDYWGQGTLVTVSS,
and
``` an immunoglobulin light variable (VL) region comprising an amino acid sequence of

```
                                      (SEQ ID NO: 18)
AIQLTQSPSSLSASVGDRVTITCRTSQGISSALAWYQQKPGKTPKLLIYD

ASSLESGVPSRFSGSGSGTDFTLTISSLQPEDFATYYCQQFNNYPRTFGQ

GTKVEIK.
```

In some embodiments, the method of treating cancer comprises administering to a subject in need thereof an anti-Clec12A antibody or antigen-binding fragment thereof comprising:

(a) an immunoglobulin heavy chain variable (VH) region comprising an amino acid sequence of

```
                                      (SEQ ID NO: 1)
QVQLQESGPGLVKPSETLSLTCTVSGGSISTYYWSWIRQPPGKGLEWIGY

IYYSGSTKYNPSLKSRVTISVDTSKNLFSLKLSSVTAADTAVYYCAREDY

YGSGSPFDYWGQGTLVTVSS,
and
``` an immunoglobulin light chain variable (VL) region comprising an amino acid sequence of

```
                                      (SEQ ID NO: 2)
IQMTQSPSSLSASVGDRVTITCRASQGIRYDLGWYQQKPGKAPKLLIYAA

SSLQSGVPSRFSGSGSGTDFTLTISSLQPEDFATYYCLQDYNFPRTFGQG

TKVEIK;
```

(b) an immunoglobulin heavy chain variable (VH) region comprising an amino acid sequence of

```
                                      (SEQ ID NO: 3)
QVQLVESGGGVVQPGRSLRLSCAASGFTFSSYGMHWVRQAPGKGLEWVAV

ISYDGSDKYYVDSVKGRFTISRDNSKNTLYLHMNSLRAEDTAVYYCARDK

GYYFDYWGQGTLVTVSS,
and
``` an immunoglobulin light chain variable (VL) region comprising an amino acid sequence of

```
                                      (SEQ ID NO: 4)
EIVMTQSPATLSLSPGERATLSCRASQSVGNRYLSWYQQKPGQAAPRLLIY

GASTRATGIPARFSGSGSGTDFTLTISSLQPEDFAVYYCQQDYNLPLTFGG

GTKVEIK;
```

(c) an immunoglobulin heavy chain variable (VH) region comprising an amino acid sequence of

```
                                      (SEQ ID NO: 5)
QVQLVESGGGVVQPGRSLRLSCAASGFTFSSYGMHWVRQAPGKGLEWVAV

ISYDGSDKYSADSVKGRFNISRDNSKNTLYLQMNSLRAEDTAVYYCARDG

SRYFDYWGQGTLVTVSS,
and
``` an immunoglobulin light chain variable (VL) region comprising an amino acid sequence of

```
                                      (SEQ ID NO: 6)
EIFMTQSPATLSLSPGERATLSCRASQSVHSKYLSWYQQKPGQAPSLLIY

GASTRATGIPARFSGSGSGTDFTLTISSLQPEDFAVYYCQQDYNLPITFG

QGTRLEIK;
or
```

(d) an immunoglobulin heavy chain variable (VH) region comprising an amino acid sequence of

```
                                      (SEQ ID NO: 7)
QLQLQESGPGLVKPSETLSLTCTVSGGSISSSTYYWGWIRQPPRKGLEWI

GSTHYRGSTYYNPSLKSRVTISVDTSKNQFSLKVSSVTAADTAVYYCARE

LTGEVFDYWGQGTLVTVSS,
and
``` an immunoglobulin light chain variable (VL) region comprising an amino acid sequence of

```
                                          (SEQ ID NO: 8)
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPFTFGP

GTKVDIK;
```

(e) an immunoglobulin heavy chain variable (VH) region comprising an amino acid sequence of

```
                                          (SEQ ID NO: 9)
QVQLQESGPGLVKPSETLSLTCTVSGGSISTYYWSWIRQPPGKGLEWLGY

IYFSGSTNYNPSLKSRLTISVAASKSQFSLKLSSVTAADTAVYYCAREDY

YGSGSPFDYWGQGTLVTVSS,
and
``` an immunoglobulin light variable (VL) region comprising an amino acid sequence of

```
                                         (SEQ ID NO: 10)
AIQMTQSPSSLSASVGDRVTITCRASQGIRNDLGWFQQKPGKAPKLLIYA

ASSLQSGVPSRFSGSGSGTYFTLTISSLQPEDSATYYCLQDYNYPRTFGQ

GTKVEIK;
```

(f) an immunoglobulin heavy chain variable (VH) region comprising an amino acid sequence of

```
                                         (SEQ ID NO: 11)
QVQLQESGPGLVKPSETLSLTCTVSGGSISTDYWSWIRQPPGKGLEWIGY

IYFSGSTKYNPSLKSRVTISVDTSKNQFSLKLSSVTAADTAVYYCAREDY

YGSGSPFDYWGQGTLVTVSS,
and
``` an immunoglobulin light variable (VL) region comprising an amino acid sequence of

```
                                         (SEQ ID NO: 12)
AIQMTQSPSSLSASVGDRVTITCRASQDIRNDLGWFQQKPGKAPKLLIYA

ASSLQSGVPSRFSGSGSGTDFTLTISSLQPEDFATYYCLQDYNFPRTFGQ

GTKVEIK;
```

(g) an immunoglobulin heavy chain variable (VH) region comprising an amino acid sequence of

```
                                         (SEQ ID NO: 13)
QVQLVESGGGVVQPGRSLRLSCAASGFTFSSYGMHWVRQAPGEGLEWVTV

ISYDGSDKYYADSVKGRFTISRDNSKSTLFLQMNSLRAEDTAVYYCARDG

QFYFDYWGQGTLVTVSS,
and
``` an immunoglobulin light variable (VL) region comprising an amino acid sequence of

```
                                         (SEQ ID NO: 14)
EIVMTQSPATLSLSPGESATLSCRASQSVTSRYLSWYQQKPGQAPRLLMY

GASTRPTGIPARFSGSGSGTDFTLTISSLQPEDFAVYYCQQDYNLPLTFG

GGTKVEIK;
```

(h) an immunoglobulin heavy chain variable (VH) region comprising an amino acid sequence of

```
                                         (SEQ ID NO: 15)
QVQLVESGGGVVQPGRSLRLSCAASGFTFSNYGMHWVRQAPGKGLEWVAV

ISYDGSDKSYKDSVKGRFTIARDNSKNTLYLQMNSLRAEDTAVYYCARDS

GRYFFDYWGQGTLVTVSS,
and
``` an immunoglobulin light variable (VL) region comprising an amino acid sequence of

```
                                         (SEQ ID NO: 16)
EIIMTQSPATLSLSPGERATLSCRASQSVSSRSLSWYQHKPGQAPRLLIY

GPSTRATGIPARFSGSGSGTDFTLTISSLQPEDFAVYYCHQDYNLPLTFG

GGTKVEIK;
or
```

(i) an immunoglobulin heavy chain variable (VH) region comprising an amino acid sequence of

```
                                         (SEQ ID NO: 17)
QVKLVESGGGVVQPGRSLRLSCAASGFTFSKYGMHWVRQAPGKGLEWVAF

IWYDGSIKNYADSVKGRFTTSRDNSKNTLYLQMNSLRAEDTAVYYCARGS

LWFGEFYFDYWGQGTLVTVSS,
and
``` an immunoglobulin light variable (VL) region comprising an amino acid sequence of

```
                                         (SEQ ID NO: 18)
AIQLTQSPSSLSASVGDRVTITCRTSQGISSALAWYQQKPGKTPKLLIYD

ASSLESGVPSRFSGSGSGTDFTLTISSLQPEDFATYYCQQFNNYPRTFGQ

GTKVEIK.
```

In some embodiments, the method of treating cancer comprises administering to a subject in need thereof an anti-Clec12A antibody or fragment thereof comprising:

(a) a heavy chain complementarity determining region (HCDR) 1 comprising an amino acid sequence of GGSISTYY (SEQ ID NO: 19), an HCDR2 comprising an amino acid sequence of IYYSGST (SEQ ID NO: 20), an HCDR3 comprising an amino acid sequence of AREDYYGSGSPFDY (SEQ ID NO: 21); and a light chain complementarity determining region (LCDR) 1 comprising an amino acid sequence of QGIRYD (SEQ ID NO: 22), an LCDR2 comprising an amino acid sequence of AAS (SEQ ID NO:23), and an LCDR3 comprising an amino acid sequence of LQDYNFPRT (SEQ ID NO: 24);

(b) an HCDR1 comprising an amino acid sequence of GFTFSSYG (SEQ ID NO: 73), an HCDR2 comprising an amino acid sequence of ISYDGSDK (SEQ ID NO: 25), and HCDR3 comprising an amino acid sequence of ARDKGYYFDY (SEQ ID NO: 26); and an LCDR1 comprising an amino acid sequence of QSVGNRY (SEQ ID NO: 27), an LCDR2 comprising an amino acid sequence of GAS (SEQ ID NO: 28), an LCDR3 comprising an amino acid sequence of QQDYNLPLT (SEQ ID NO:29);

(c) an HCDR1 comprising an amino acid sequence of GFTFSSYG (SEQ ID NO: 73), an HCDR2 comprising an amino acid sequence of ISYDGSDK (SEQ ID NO: 25), an HCDR3 comprising an amino acid sequence of ARDGSRYFDY (SEQ ID NO: 30); and an LCDR1 comprising an amino acid sequence of QSVHSKY (SEQ ID NO: 31), an LCDR2 comprising an amino acid sequence of GAS (SEQ ID NO: 28), an LCDR3 comprising an amino acid sequence of QQDYNLPIT (SEQ ID NO: 32); or (d) an HCDR1 comprising an amino acid sequence of GGSISSSTYY (SEQ ID NO: 33), an HCDR2 comprising an amino acid sequence of THYRGST (SEQ ID NO: 34), an HCDR3 comprising an amino acid sequence of ARELTGEVFDY (SEQ ID NO: 35); and an LCDR1 comprising an amino acid sequence of QSISSY (SEQ ID NO:36), an LCDR2 comprising an amino acid sequence of AAS (SEQ ID NO: 23), an LCDR3 comprising an amino acid sequence of QQSYSTPFT (SEQ ID NO: 37);

(e) an HCDR1 comprising an amino acid sequence of GGSISTYY (SEQ ID NO: 19), an HCDR2 comprising an amino acid sequence of IYFSGST (SEQ ID NO: 38), and HCDR3 comprising an amino acid sequence of AREDYYGSGSPFDY (SEQ ID NO:21); and an LCDR1 comprising an amino acid sequence of QGIRND (SEQ ID NO: 39), an LCDR2 comprising an amino acid sequence of AAS (SEQ ID NO: 23), an LCDR3 comprising an amino acid sequence of LQDYNYPRT (SEQ ID NO:40);

(f) an HCDR1 comprising an amino acid sequence of GGSISTDY (SEQ ID NO:41), an HCDR2 comprising an amino acid sequence of IYFSGST (SEQ ID NO:38), and HCDR3 comprising an amino acid sequence of AREDYYGSGSPFDY (SEQ ID NO:21); and an LCDR1 comprising an amino acid sequence of QDIRND (SEQ ID NO:42), an LCDR2 comprising an amino acid sequence of AAS (SEQ ID NO: 23), an LCDR3 comprising an amino acid sequence of LQDYNFPRT (SEQ ID NO: 24);

(g) an HCDR1 comprising an amino acid sequence of GFTFSSYG (SEQ ID NO: 73), an HCDR2 comprising an amino acid sequence of ISYDGSDK (SEQ ID NO:25), and HCDR3 comprising an amino acid sequence of ARDGQFYFDY (SEQ ID NO: 43); and an LCDR1 comprising an amino acid sequence of QSVTSRY (SEQ ID NO:44), an LCDR2 comprising an amino acid sequence of GAS (SEQ ID NO:28), an LCDR3 comprising an amino acid sequence of QQDYNLPLT (SEQ ID NO:29);

(h) an HCDR1 comprising an amino acid sequence of GFTFSNYG (SEQ ID NO: 45), an HCDR2 comprising an amino acid sequence of ISYDGSDK (SEQ ID NO: 25), and HCDR3 comprising an amino acid sequence of ARDSGRYFFDY (SEQ ID NO:46); and an LCDR1 comprising an amino acid sequence of QSVSSRS (SEQ ID NO:47), an LCDR2 comprising an amino acid sequence of GPS (SEQ ID NO: 48), an LCDR3 comprising an amino acid sequence of HQDYNLPLT (SEQ ID NO:49); or (i) an HCDR1 comprising an amino acid sequence of GFTFSKYG (SEQ ID NO: 50), an HCDR2 comprising an amino acid sequence of IWYDGSIK (SEQ ID NO: 51), and HCDR3 comprising an amino acid sequence of ARGSLWFGEFYFDY (SEQ ID NO: 52); and an LCDR1 comprising an amino acid sequence of QGISSA (SEQ ID NO: 53), an LCDR2 comprising an amino acid sequence of DAS (SEQ ID NO: 54), an LCDR3 comprising an amino acid sequence of QQFN-NYPRT (SEQ ID NO: 55).

In some embodiments, the anti-Clec12A antibody or antigen-binding fragment thereof is a monoclonal antibody or a single-chain variable fragment (scFv).

In some embodiments, the anti-Clec12A antibody is an antibody comprising an IgG constant region.

In some embodiments, the antigen-binding fragment thereof is a single-chain variable fragment (scFv).

In some embodiments, the scFv comprises a leader sequence, a heavy chain variable sequence, a GS-Linker, and a light chain variable sequence.

In some embodiments, the method of treating cancer comprises administering to a subject in need thereof an scFv comprising a sequence having at least about 80% identity to:

(a)
```
                                        (SEQ ID NO: 56)
QVQLQESGPGLVKPSETLSLTCTVSGGSISTYYWSWIRQPPGKGLEWIGY

IYYSGSTKYNPSLKSRVTISVDTSKNLFSLKLSSVTAADTAVYYCAREDY

YGSGSPFDYWGQGTLVTVSSASTGGGGSGGGGSGGGGSAIQMTQSPSSLS

ASVGDRVTITCRASQGIRYDLGWYQQKPGKAPKLLIYAASSLQSGVPSRF

SGSGSGTDFTLTISSLQPEDFATYYCLQDYNFPRTFGQGTKVEIK;
```

(b)
```
                                        (SEQ ID NO: 57)
QVQLVESGGGVVQPGRSLRLSCAASGFTFSSYGMHWVRQAPGKGLEWVAI

VISYDGSDKYYVDSVKGRFTISRDNSKNTLYLHMNSLRAEDTAVYYCARD

KGYYFDYWGQGTLVTVSSASTGGGGSGGGGSGGGGSEIVMTQSPATLSLS

PGERATLSCRASQSVGNRYLSWYQQKPGQAPRLLIYGASTRATGIPARES

GSGSGTDFTLTISSLQPEDFAVYYCQQDYNLPLTFGGGTKVEIK;
```

(c)
```
                                        (SEQ ID NO: 58)
QVQLVESGGGVVQPGRSLRLSCAASGFTFSSYGMHWVRQAPGKGLEWVAV

ISYDGSDKYSADSVKGRFNISRDNSKNTLYLQMNSLRAEDTAVYYCARDG

SRYFDYWGQGTLVTVSSASTGGGGSGGGGSGGGGSEIFMTQSPATLSLPG

ERATLSCRASQSVHSKYLSWYQQKPGQAPSLLIYGASTRATGIPARFSGS

GSGTDFTLTISSLQPEDFAVYYCQQDYNLPITFGQGTRLEIK;
or
```

(d)
```
                                        (SEQ ID NO: 59)
QLQLQESGPGLVKPSETLSLTCTVSGGSISSSTYYWGWIRQPPRKGLEWI

GSTHYRGSTYYNPSLKSRVTISVDTSKNQFSLKVSSVTAADTAVYYCARE

LTGEVFDYWGQGTLVTVSSASTGGGGSGGGGSGGGGSDIQMTQSPSSLSA

SVGDRVTITCRASQSISSYLNWYQQKPGKAPKLLIYAASSLQSGVPSRFS

GSGSGTDFTLTISSLQPEDFATYYCQQSYSTPFTFGPGTKVDIK.
```

In some embodiments, the method of treating cancer comprises administering to a subject in need thereof an scFv comprising a sequence of:

```
(a)
                                          (SEQ ID NO: 56)
QVQLQESGPGLVKPSETLSLTCTVSGGSISTYYWSWIRQPPGKGLEWIGY

IYYSGSTKYNPSLKSRVTISVDTSKNLFSLKLSSVTAADTAVYYCAREDY

YGSGSPFDYWGQGTLVTVSSASTGGGGSGGGGSGGGGSAIQMTQSPSSLS

ASVGDRVTITCRASQGIRYDLGWYQQKPGKAPKLLIYAASSLQSGVPSRF

SGSGSGTDFTLTISSLQPEDFATYYCLQDYNFPRTFGQGTKVEIK;

(b)
                                          (SEQ ID NO: 57)
QVQLVESGGGVVQPGRSLRLSCAASGFTFSSYGMHWVRQAPGKGLEWVAI

VISYDGSDKYYVDSVKGRFTISRDNSKNTLYLHMNSLRAEDTAVYYCARD

KGYYFDYWGQGTLVTVSSASTGGGGSGGGGSGGGGSEIVMTQSPATLSLS

PGERATLSCRASQSVGNRYLSWYQQKPGQAPRLLIYGASTRATGIPARFS

GSGSGTDFTLTISSLQPEDFAVYYCQQDYNLPLTFGGGTKVEIK;

(c)
                                          (SEQ ID NO: 58)
QVQLVESGGGVVQPGRSLRLSCAASGFTFSSYGMHWVRQAPGKGLEWVAV

ISYDGSDKYSADSVKGRFNISRDNSKNTLYLQMNSLRAEDTAVYYCARDG

SRYFDYWGQGTLVTVSSASTGGGGSGGGGSGGGGSEIFMTQSPATLSLPG

ERATLSCRASQSVHSKYLSWYQQKPGQAPSLLIYGASTRATGIPARFSGS

GSGTDFTLTISSLQPEDFAVYYCQQDYNLPITFGQGTRLEIK;
or (d)
                                          (SEQ ID NO: 59)
QLQLQESGPGLVKPSETLSLTCTVSGGSISSSTYYWGWIRQPPRKGLEWI

GSTHYRGSTYYNPSLKSRVTISVDTSKNQFSLKVSSVTAADTAVYYCARE

LTGEVFDYWGQGTLVTVSSASTGGGGSGGGGSGGGGSDIQMTQSPSSLSA

SVGDRVTITCRASQSISSYLNWYQQKPGKAPKLLIYAASSLQSGVPSRFS

GSGSGTDFTLTISSLQPEDFATYYCQQSYSTPFTFGPGTKVDIK.
```

In some embodiments, the cancer is selected from leukemia, lymphoma, and myeloma.

In some embodiments, the treatment comprises administration of one or more additional agents.

In some embodiments, the one or more additional agents is selected from an antibody, a chemotherapeutic, and radiation therapy.

Definitions

A or An: The articles "a" and "an" are used herein to refer to one or to more than one (i.e., to at least one) of the grammatical object of the article. By way of example, "an element" means one element or more than one element.

Affinity: As used herein, the term "affinity" refers to the characteristics of a binding interaction between a binding moiety (e.g., an antigen binding moiety (e.g., variable domain described herein) and/or Fc receptor binding moiety (e.g., FcRn binding moiety described herein)) and a target (e.g., an antigen (e.g., Clec12A) and/or FcR (e.g., FcRn)) and that indicates the strength of the binding interaction. In some embodiments, the measure of affinity is expressed as a dissociation constant ($K_D$). In some embodiments, a bind-ing moiety has a high affinity for a target (e.g., a $K_D$ of less than about $10^{-7}$ M, less than about $10^{-8}$ M, or less than about $10^{-9}$ M). In some embodiments, a binding moiety has a low affinity for a target (e.g., a $K_D$ of higher than about $10^{-7}$ M, higher than about $10^{-6}$ M, higher than about $10^{-5}$ M, or higher than about $10^{-4}$ M). In some embodiments, a binding moiety has high affinity for a target at a first pH, has low affinity for the target at a second pH, and has an intermediate affinity for the target at a pH level between the first pH and the second pH.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Antibody: As used herein, the term "antibody" refers to a polypeptide that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab, F(ab')2, Fd, Fv, and dAb fragments) as well as complete antibodies, e.g., intact immunoglobulins of types IgA, IgG, IgE, IgD, IgM (as well as subtypes thereof). The light chains of the immunoglobulin can be of types kappa or lambda.

Binding Moiety: As used herein, a "binding moiety" is any molecule or part of a molecule capable of specifically binding a target, e.g., a target of interest (e.g., an antigen (e.g., Clec12A) and/or FcR (e.g., FcRn)). Binding moieties include, e.g., antibodies, antigen binding fragments thereof, Fc regions or Fc fragments thereof, antibody mimetics, peptides, and aptamers.

Antibody-binding fragment or antibody fragment thereof refers to a portion of an intact antibody. An antibody-binding fragment or antibody fragment thereof refers to a portion of an intact antibody that binds to an antigen (e.g., Clec12A). An antigen-binding fragment can contain the antigenic determining variable regions of an intact antibody. Examples of antibody fragments include, but are not limited to Fab, Fab', F(ab')2, and Fv fragments, linear antibodies, antibody mimetics, scFvs, and single chain antibodies.

Complementarity Determining Region (CDR): A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1 156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of IMGT, Kabat, Chothia, extended, AbM, contact, and/or conformational definitions. In certain embodiments, the CDRs are identified or numbered according to the IMGT numbering system.

Constant region: As used herein, the term "constant region" refers to a polypeptide that corresponds to, or is derived from, one or more constant region immunoglobulin domains of an antibody. A constant region can include any or all of the following immunoglobulin domains: a CH1 domain, a hinge region, a CH2 domain, a CH3 domain (derived from an IgA, IgD, IgG, IgE, or IgM), and a CH4 domain (derived from an IgE or IgM).

Epitope: As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giege R et al, (1994) Acta Crystallogr D Biol Crystallogr 50 (Pt 4): 339-350; McPherson A (1990) Eur J Biochem 189:1-23; Chayen N E (1997) Structure 5:1269-1274; McPherson A (1976) J Biol Chem 251:6300-6303). Antibody: antigen crystals may be studied using well known X-ray diffraction techniques and may be refined using computer software known in the art, e.g., Refmac and Phenix. Mutagenesis mapping studies may be accomplished using any method known to one of skill in the art. See, e.g., Champe M et al, (1995) J Biol Chem 270:1388-1394 and Cunningham B C & Wells J A (1989) Science 244:1081-1085 for a description of mutagenesis techniques, including alanine scanning mutagenesis techniques.

Fc region: As used herein, the term "Fc region" refers to a dimer of two "Fc polypeptides", each "Fc polypeptide" comprising the constant region of an antibody excluding the first constant region immunoglobulin domain. In some embodiments, an "Fc region" includes two Fc polypeptides linked by one or more disulfide bonds, chemical linkers, or peptide linkers. "Fc polypeptide" refers to the last two constant region immunoglobulin domains of IgA, IgD, and IgG, and the last three constant region immunoglobulin domains of IgE and IgM, and may also include part or all of the flexible hinge N-terminal to these domains. For IgG, "Fc polypeptide" comprises immunoglobulin domains Cgamma2 (Cγ2) and Cgamma3 (Cγ3) and the lower part of the hinge between Cgamma1 (Cγ1) and Cγ2. Although the boundaries of the Fc polypeptide may vary, the human IgG heavy chain Fc polypeptide is usually defined to comprise residues starting at T223 or C226 or P230, to its carboxyl-terminus, wherein the numbering is according to the EU index as in Kabat et al. (1991, NIH Publication 91-3242, National Technical Information Services, Springfield, VA). For IgA, Fc polypeptide comprises immunoglobulin domains Calpha2 (Cα2) and Calpha3 (Cα3) and the lower part of the hinge between Calpha1 (Cal) and Cα2. An Fc region can be synthetic, recombinant, or generated from natural sources such as IVIG.

$K_a$: As used herein, "$K_a$" refers to an association rate of a particular binding moiety and a target to form a binding moiety/target complex.

$K_d$: As used herein, "$K_d$" refers to a dissociation rate of a particular binding moiety/target complex.

$K_D$: As used herein, "$K_D$" refers to a dissociation constant, which is obtained from the ratio of $K_d$ to $K_a$ (i.e., $K_d/K_a$) and is expressed as a molar concentration (M). $K_D$ values can be determined using methods well established in the art, e.g., by using surface plasmon resonance, or using a biosensor system such as a Biacore® system.

Reference: A "reference" entity, system, amount, set of conditions, etc., is one against which a test entity, system, amount, set of conditions, etc. is compared as described herein. For example, in some embodiments, a "reference" antibody is a control antibody that is not engineered as described herein.

Selective binding: As used herein, "selective binding", "selectively binds" "specific binding", or "specifically binds" refers, with respect to a binding moiety and a target, preferential association of a binding moiety to a target and not to an entity that is not the target. A certain degree of non-specific binding may occur between a binding moiety and a non-target. In some embodiments, a binding moiety selectively binds a target if binding between the binding moiety and the target is greater than 2-fold, greater than 5-fold, greater than 10-fold, or greater than 100-fold as compared with binding of the binding moiety and a non-target. In some embodiments, a binding moiety selectively binds a target if the binding affinity is less than about $10^{-5}$ M, less than about $10^{-6}$ M, less than about $10^{-7}$ M, less than about $10^{-8}$ M, or less than about $10^{-9}$ M. In some embodiments, a molecule that specifically binds to an antigen may bind to other peptides or polypeptides, generally with lower affinity as determined by, e.g., immunoassays, BIACORE®, KinExA 3000 instrument (Sapidyne Instruments, Boise, ID), or other assays known in the art.

Single-chain variable fragment (scFv): As used herein, the term "single-chain variable fragment" or "scFv" refers to a fusion protein of the variable regions of the heavy ($V_H$) and light chains ($V_L$) of an immunoglobulin (e.g., mouse or human) covalently linked to form a $V_H$::VL heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80 (6): 1910-1917 (2008) and WO 2014/087010, the contents of which are hereby incorporated by reference in their entireties.

Subject: The term "subject", as used herein, means any subject for whom diagnosis, prognosis, or therapy is desired. For example, a subject can be a mammal, e.g., a human or non-human primate (such as an ape, monkey, orangutan, or chimpanzee), a dog, cat, guinea pig, rabbit, rat, mouse, horse, cattle, or cow.

Target: As used herein, a "target" is any molecule specifically bound by a binding moiety of an antibody or an antigen-binding fragment thereof. In some embodiments, a target is an antigen described herein (e.g., Clec12A). In some embodiments, a target is an FcR (e.g., FcRn). The terms "first target" and "second target" are used herein to refer to molecules of two distinct molecular species, rather than two molecules of the same molecular species. For example, in some embodiments, a first target is a serum protein and a second target is FcRn.

Therapeutically effective amount: As used herein, the term "therapeutically effective amount" refers to an amount of a therapeutic molecule (e.g., an anti-Clec12A antibody described herein) which confers a therapeutic effect on a treated subject, at a reasonable benefit/risk ratio applicable to any medical treatment. Therapeutic effect may be objective (i.e., measurable by some test or marker) or subjective (i.e., subject gives an indication of or feels an effect). In particular, the "therapeutically effective amount" refers to an amount of a therapeutic molecule or composition effective to treat, ameliorate, or prevent a particular disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount can be administered in a dosing regimen that may comprise multiple unit doses. For any particular therapeutic molecule, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular subject may depend upon a variety of factors including the disorder being treated and the severity of the disorder; the activity of the specific pharmaceutical agent employed; the specific composition employed; the age, body weight, general health, sex and diet of the subject; the time of administration, route of administration, and/or rate of excretion or metabolism of the specific therapeutic molecule employed; the duration of the treatment; and like factors as is well known in the medical arts.

Treatment: As used herein, the term "treatment" (also "treat" or "treating") refers to any administration of a therapeutic molecule (e.g., an anti-Clec12A antibody described herein) that partially or completely alleviates, ameliorates, relieves, inhibits, delays onset of, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

BRIEF DESCRIPTION OF DRAWINGS

Drawings are for illustration purposes only; not for limitation.

DETAILED DESCRIPTION

Figure 1A:
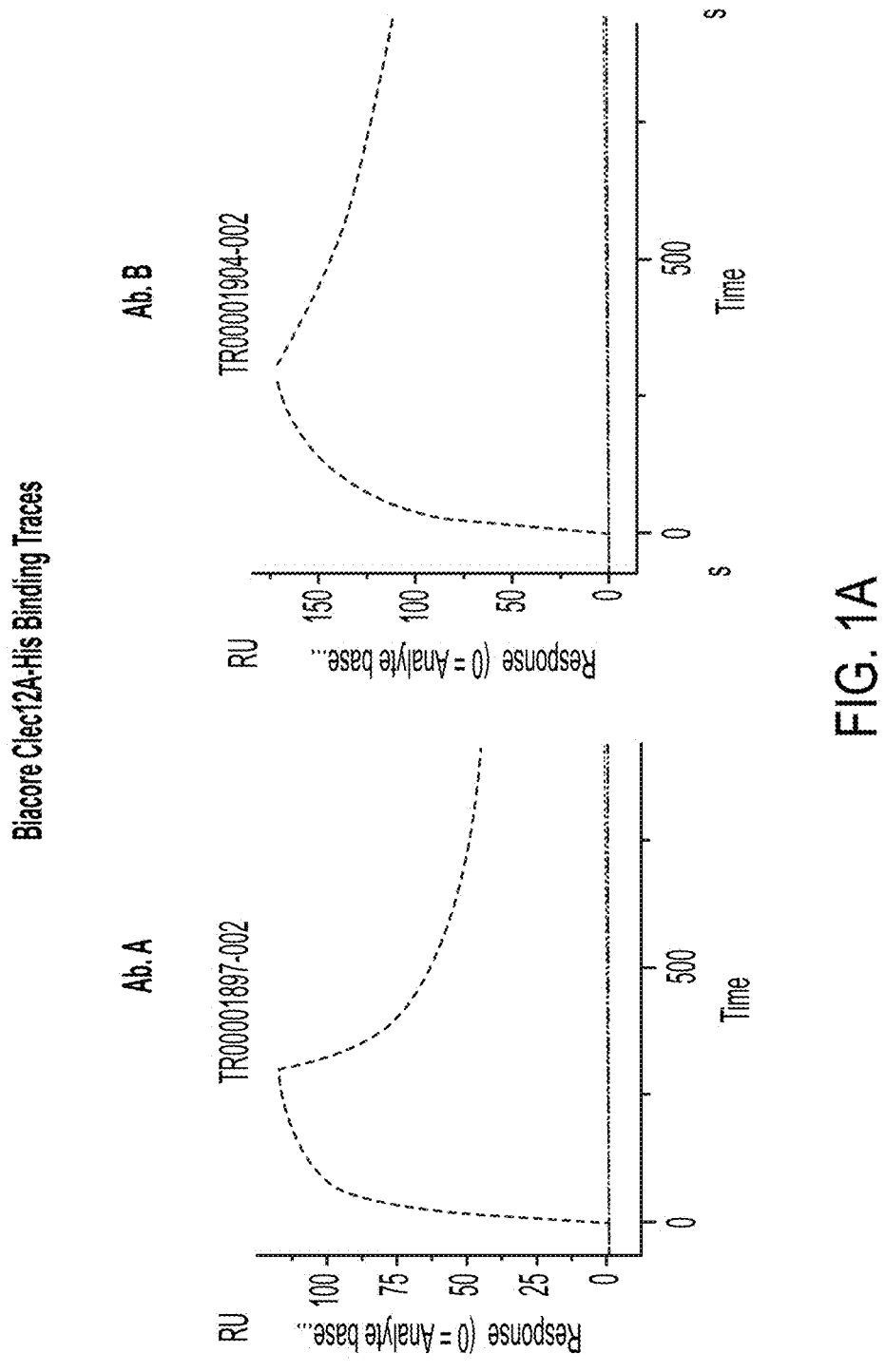
FIG. 1A and FIG. 1B show Biacore Clec12A-His binding traces from surface plasmon resonance assays.

The present disclosure is based, in part, on the discovery of engineered antibodies and antigen binding fragments thereof that bind to Clec12A (e.g., human Clec12A). Clec12A is a C-type lectin domain family 12 member A which is a cell-surface receptor that has an ITIM motif and modulates signaling cascades and mediates tyrosine phosphorylation of target MAP kinases.

Clec12A is highly expressed in cancerous cells, including acute myeloid leukemia cells, while not being expressed in normal hematopoietic stem cells. Further, CLL-1 is also expressed on the surface of leukemic stem cells (LSC), which can self-renew, producing more leukemic cells and are associated with relapses.

In some embodiments, Clec12A is used to treat cancers. Anti-Clec12A antibodies are used to target AML using either bispecific antibodies such as CD3/Clec12A to recruit unstimulated primary T cells in patients against cancer cells with Clec12A on surface, or developing CAR T cells specific for Clec12A antigen.

Antibodies

The antibodies described herein are designed to bind to Clec12A. In certain embodiments, the anti-Clec12A antibodies and antigen-binding fragments thereof bind to human Clec12A. Human Clec12A is described in the art and is described, for example, in NCBI Reference No: NP_612210.4, NCBI Reference No: NP_963917.2, NCBI Reference No: NP_001193939.1, and NCBI Reference No: NP_001287659.1.

An anti-Clec12A antibody described herein can be an immunoglobulin, heavy chain antibody, light chain antibody, LRR-based antibody, or other protein scaffold with antibody-like properties, as well as other immunological binding moiety known in the art, including, e.g., a Fab, Fab', Fab'$_2$, Fab$_2$, Fab$_3$, F(ab')$_2$, Fd, Fv, Feb, scFv, SMIP, antibody, diabody, triabody, tetrabody, minibody, maxibody, tandab, DVD, BiTe, TandAb, or the like, or any combination thereof. The subunit structures and three-dimensional configurations of different classes of antibodies are known in the art.

An antibody can be an immunoglobulin molecule of four polypeptide chains, e.g., two heavy (H) chains and two light (L) chains. A heavy chain can include a heavy chain variable domain and a heavy chain constant domain. A heavy chain constant domain can include CH1, hinge, CH2, CH3, and in some instances CH4 regions. A suitable heavy chain constant region may be derived from any immunoglobulin (e.g., IgA, IgG, or IgE). In some embodiments, a suitable heavy chain constant region may be derived from IgG1, IgG2, or IgG4. In particular embodiments, a suitable heavy chain constant region is derived from IgG1. A light chain can include a light chain variable domain and a light chain constant domain. A light chain constant domain can include either a kappa light chain or a lambda light chain. A heavy chain variable domain of a heavy chain and a light chain variable domain of a light chain can typically be further subdivided into regions of variability, termed complementarity determining regions (CDRs), interspersed with regions that are more conserved, termed framework regions (FR). Such heavy chain and light chain variable domains can each include three CDRs and four framework regions, arranged from amino-terminus to carboxyl-terminus in the following order: FR1, CDR1, FR2, CDR2, FR3, CDR3, FR4, one or more of which can be engineered as described herein. The assignment of amino acids to each domain is in accordance with the definitions of Kabat Sequences of Proteins of Immunological Interest (National Institutes of Health, Bethesda, Md. (1987 and 1991)), or Chothia & Lesk *J. Mol. Biol.* 196:901-917 (1987); Chothia et al. *Nature* 342:878-883 (1989). As used herein, CDRs are referred to for each of the heavy (HCDR1, HCDR2, HCDR3) and light (LCDR1, LCDR2, LCDR3) chains.

Embodiments of the invention include antibodies comprising the CDRs found in the VH and VL domains described herein that are identified using conventional numbering systems, such as the IMGT, Kabat and Clothia numbering systems. Such numbering systems are well-known in the art. In certain embodiments, the CDRs are identified or numbered according to the IMGT numbering system.

Exemplary Anti-Clec12A Antibodies

Exemplary anti-Clec12A antibodies are provided in the table below. Heavy chain variable (VH) and light chain variable (VL) sequences of anti-Clec12A antibodies A-I are presented below.

| Ab | Chain | Sequences |
|---|---|---|
| A | VH | QVQLQESGPGLVKPSETLSLTCTVSGGSISTYYWSWIRQPPGKGLEWIGYI YYSGSTKYNPSLKSRVTISVDTSKNLFSLKLSSVTAADTAVYYCAREDYY GSGSPFDYWGQGTLVTVSS (SEQ ID NO: 1) |
|  | VL | IQMTQSPSSLSASVGDRVTITCRASQGIRYDLGWYQQKPGKAPKLLIYAAS SLQSGVPSRFSGSGSGTDFTLTISSLQPEDFATYYCLQDYNFPRTFGQGTKV EIK(SEQ ID NO: 2) |
| B | VH | QVQLVESGGGVVQPGRSLRLSCAASGFTFSSYGMHWVRQAPGKGLEWV AVISYDGSDKYYVDSVKGRFTISRDNSKNTLYLHMNSLRAEDTAVYYCAR DKGYYFDYWGQGTLVTVSS(SEQ ID NO: 3) |
|  | VL | EIVMTQSPATLSLSPGERATLSCRASQSVGNRYLSWYQQKPGQAPRLLIYG ASTRATGIPARFSGSGSGTDFTLTISSLQPEDFAVYYCQQDYNLPLTFGGGT KVEIK(SEQ ID NO: 4) |
| C | VH | QVQLVESGGGVVQPGRSLRLSCAASGFTFSSYGMHWVRQAPGKGLEWV AVISYDGSDKYSADSVKGRFNISRDNSKNTLYLQMNSLRAEDTAVYYCAR DGSRYFDYWGQGTLVTVSS (SEQ ID NO: 5) |
|  | VL | EIFMTQSPATLSLSPGERATLSCRASQSVHSKYLSWYQQKPGQAPSLLIYG ASTRATGIPARFSGSGSGTDFTLTISSLQPEDFAVYYCQQDYNLPITFGQGT RLEIK(SEQ ID NO: 6) |
| D | VH | QLQLQESGPGLVKPSETLSLTCTVSGGSISSSTYYWGWIRQPPRKGLEWIGS THYRGSTYYNPSLKSRVTISVDTSKNQFSLKVSSVTAADTAVYYCARELT GEVFDYWGQGTLVTVSS(SEQ ID NO: 7) |
|  | VL | DIQMTQSPSSLSASVGDRVTITCRASQSISSYLNWYQQKPGKAPKLLIYAAS SLQSGVPSRFSGSGSGTDFTLTISSLQPEDFATYYCQQSYSTPFTFGPGTKV DIK (SEQ ID NO: 8) |
| E | VH | QVQLQESGPGLVKPSETLSLTCTVSGGSISTYYWSWIRQPPGKGLEWLGYI YFSGSTNYNPSLKSRLTISVAASKSQFSLKLSSVTAADTAVYYCAREDYYG SGSPFDYWGQGTLVTVSS (SEQ ID NO: 9) |
|  | VL | AIQMTQSPSSLSASVGDRVTITCRASQGIRNDLGWFQQKPGKAPKLLIYAA SSLQSGVPSRFSGSGSGTYFTLTISSLQPEDSATYYCLQDYNYPRTFGQGTK VEIK (SEQ ID NO: 10) |
| F | VH | QVQLQESGPGLVKPSETLSLTCTVSGGSISTDYWSWIRQPPGKGLEWIGYI YFSGSTKYNPSLKSRVTISVDTSKNQFSLKLSSVTAADTAVYYCAREDYYG SGSPFDYWGQGTLVTVSS (SEQ ID NO: 11) |
|  | VL | AIQMTQSPSSLSASVGDRVTITCRASQDIRNDLGWFQQKPGKAPKLLIYAA SSLQSGVPSRFSGSGSGTDFTLTISSLQPEDFATYYCLQDYNFPRTFGQGTK VEIK(SEQ ID NO: 12) |
| G | VH | QVQLVESGGGVVQPGRSLRLSCAASGFTFSSYGMHWVRQAPGEGLEWVT VISYDGSDKYADSVKGRFTISRDNSKSTLFLQMNSLRAEDTAVYYCARD GQFYFDYWGQGTLVTVSS(SEQ ID NO: 13) |
|  | VL | EIVMTQSPATLSLSPGESATLSCRASQSVTSRYLSWYQQKPGQAPRLLMYG ASTRPTGIPARFSGSGSGTDFTLTISSLQPEDFAVYYCQQDYNLPLTFGGGT KVEIK(SEQ ID NO: 14) |
| H | VH | QVQLVESGGGVVQPGRSLRLSCAASGFTFSNYGMHWVRQAPGKGLEWV AVISYDGSDKSYKDSVKGRFTIARDNSKNTLYLQMNSLRAEDTAVYYCAR DSGRYFFDYWGQGTLVTVSS(SEQ ID NO: 15) |

-continued

| Ab | Chain | Sequences |
|----|-------|-----------|
| | VL | EIIMTQSPATLSLSPGERATLSCRASQSVSSRSLSWYQHKPGQAPRLLIYGP STRATGIPARFSGSGSGTDFTLTISSLQPEDFAVYYCHQDYNLPLTFGGGTK VEIK(SEQ ID NO: 16) |
| I | VH | QVKLVESGGGVVQPGRSLRLSCAASGFTFSKYGMHWVRQAPGKGLEWV AFIWYDGSIKNYADSVKGRFTTSRDNSKNTLYLQMNSLRAEDTAVYYCA RGSLWFGEFYFDYWGQGTLVTVSS(SEQ ID NO: 17) |
| | VL | AIQLTQSPSSLSASVGDRVTITCRTSQGISSALAWYQQKPGKTPKLLIYDAS SLESGVPSRFSGSGSGTDFTLTISSLQPEDFATYYCQQFNNYPRTFGQGTKV EIK (SEQ ID NO: 18) |

VH = Heavy Chain Variable
VL = Light Chain Variable

In some embodiments, the anti-Clec12A antibody comprises a heavy chain and/or a light chain amino acid sequence having at least about 85%, about 90%, about 91%, about 92%, about 93%, about 94%, about 95%, about 96%, about 97%, about 98%, or about 99% sequence identity to any one of SEQ ID Nos: 1-18.

In some embodiments, the anti-Clec12A antibody comprises no more than 30, 29, 28, 27, 26, 25, 24, 23, 22, 21, 20, 19, 18, 17, 16, 15, 14, 13, 12, 11, 10, 9, 8, 7, 6, 5, 4, 3, or 2 amino acid substitutions relative to, SEQ ID NO: 1-18.

As will be understood by those of skill in the art, any such heavy chain CDR sequence may be readily combined, e.g., by techniques of molecular biology, with any other antibody sequences or domains provided herein or otherwise known in the art, including any framework regions, CDRs, or constant domains, or portions thereof as disclosed herein or otherwise known in the art, as may be present in an antibody or an antigen-binding fragment thereof of any format as disclosed herein or otherwise known in the art.

In various engineered antibodies described herein, a heavy chain constant domain can be of any class (or subclass). In various engineered antibodies described herein, a heavy chain constant domain can include the amino acid sequence of any of one or more of IgG, IgM, IgA, IgD, or IgE, including subclasses such as IgG1, IgG2, IgG3, IgG4, IgA1, and IgA2. In various embodiments, a constant domain of engineered antibodies described herein can include a mixture of two or more classes (or subclasses) of immunoglobulin heavy chain constant domain. For example, an anti-Clec12A antibody can include a first portion of a constant domain that has a sequence of an immunoglobulin constant domain selected from an IgG, IgM, IgA, IgD, or IgE class constant domain and a second portion of a constant domain that has a sequence of an immunoglobulin constant domain different from the first and selected from an IgG, IgM, IgA, IgD, or IgE class constant domain. In some instances, a constant domain of an anti-Clec12A antibody described herein can include a mixture of two or more subclasses of a particular class of constant domain, e.g., a first portion of a constant domain that has a sequence of an immunoglobulin constant domain selected from an IgG1, IgG2, IgG3, or IgG4 subclass constant domain and a second portion of a constant domain that has a sequence of an immunoglobulin constant domain different from the first and selected from an IgG1, IgG2, IgG3, or IgG4 subclass constant domain. In some particular embodiments, a constant domain includes all or a portion of an IgG2 constant domain and all or a portion of an IgG4 constant domain.

In some instances, the anti-Clec12A antibody includes an antibody constant region, Fc region or Fc fragment that exhibits altered binding (as compared to a reference constant region) to one or more Fc receptors (e.g., FcγRI, FcγRIIA, FcγRIIB, FcγRIIIA, FcγRIIIB, FcγRIV, or FcRn receptor). In some embodiments, a constant region, Fc region or Fc fragment is engineered to bind to a target (e.g., an FcRn receptor) in an altered manner (e.g., in a pH sensitive manner (e.g., in a more or less pH sensitive manner) and/or decreased or increased binding) relative to a reference constant region, Fc region or Fc fragment. In some embodiments, the anti-Clec12A antibody includes an antibody constant region, Fc region or Fc fragment that exhibits decreased binding (as compared to a reference constant region) to one or more Fcγ receptor (e.g., FcγRI, FcγRIIA, FcγRIIB, FcγRIIIA, FcγRIIIB, or FcγRIV). In some embodiments, the anti-Clec12A antibody includes an antibody constant region, Fc region or Fc fragment that exhibits increased binding to the FcRn receptor (as compared to a reference constant region) at serum pH and/or at intracellular pH.

For example, an anti-Clec12A antibody can include a constant region, Fc region or Fc fragment of an IgG antibody engineered to include an amino acid addition, deletion, or substitution, of one or more of amino acid residues 251-256, 285-290, 308-314, 385-389, and 428-436 (Kabat numbering (Kabat et al., (1991) Sequences of Proteins of Immunological Interest, NIH)). Without wishing to be bound by theory, it is believed that one or more of these constant region, Fc region, or Fc fragment amino acids mediate interaction with an Fc receptor, e.g., FcRn. In some embodiments, one or more of these disclosed amino acids is substituted with histidine, arginine, lysine, aspartic acid, glutamic acid, serine, threonine, asparagine, or glutamine. In some embodiments, a non-histidine residue is substituted with a histidine residue. In some embodiments, a histidine residue is substituted with a non-histidine residue.

In some embodiments, the anti-Clec12A antibody includes a constant region, Fc region or Fc fragment of an IgG antibody having amino acid modifications at one or more of positions 308, 309, 311, 312, and 314, more specifically, having substitutions at one or more of positions 308, 309, 311, 312 and 314 with threonine, proline, serine, aspartic acid and leucine respectively. In some embodiments, residues at one or more of positions 308, 309, and 311 are substituted with isoleucine, proline, and glutamic acid, respectively. In yet other embodiments, residues at one or more of positions 308, 309, 311, 312, and 314, are substituted with threonine, proline, serine, aspartic acid, and leucine, respectively.

In some embodiments, the anti-Clec12A antibody includes a constant region, Fc region or Fc fragment of an IgG antibody having amino acid modifications at one or more of positions 251, 252, 254, 255, and 256, more specifically, having substitutions at one or more of these positions. In some embodiments, residue 251 is substituted with leucine or arginine, residue 252 is substituted with leucine, tyrosine, phenylalanine, serine, tryptophan or threonine, residue 254 is substituted with threonine or serine, residue 255 is substituted with leucine, glycine, isoleucine or arginine, and/or residue 256 is substituted with serine, phenylalanine, arginine, glutamine, glutamic acid, aspartic acid, alanine, asparagine or threonine. In some embodiments, residue 251 is substituted with leucine, residue 252 is substituted with tyrosine or leucine, residue 254 is substituted with threonine or serine, and/or residue 255 is substituted with arginine. In yet other embodiments, residue 252 is substituted with phenylalanine and/or residue 256 is substituted with aspartic acid. In some embodiments, residue 251 is substituted with leucine, residue 252 is substituted with tyrosine, residue 254 is substituted with threonine or serine, and/or residue 255 is substituted with arginine.

In some embodiments, the anti-Clec12A antibody includes a constant region, Fc region or Fc fragment of an IgG antibody having amino acid modifications at one or more of positions 428, 433, 434, 435, and 436, more specifically, having substitutions at one or more of these positions. In some embodiments, residue 428 is substituted with methionine, threonine, leucine, phenylalanine, or serine, residue 433 is substituted with lysine, arginine, serine, isoleucine, proline, glutamine, or histidine, residue 434 is substituted with phenylalanine, tyrosine, or histidine, residue 435 is substituted with tyrosine, and/or residue 436 is substituted with histidine, asparagine, arginine, threonine, lysine, methionine, or threonine. In some embodiments, residues at one or more positions 433, 434, 435, and 436 are substituted with lysine, phenylalanine, tyrosine, and histidine, respectively. In some embodiments, residue 428 is substituted with methionine and/or residue 434 is substituted with tyrosine.

In some embodiments, the anti-Clec12A antibody includes a constant region, Fc region or Fc fragment of an IgG antibody having amino acid modifications at one or more of positions 385, 386, 387, and 389, more specifically, having substitutions at one or more of these positions. In some embodiments, residue 385 is substituted with arginine, aspartic acid, serine, threonine, histidine, lysine, or alanine, residue 386 is substituted with threonine, proline, aspartic acid, serine, lysine, arginine, isoleucine, or methionine, residue 387 is substituted with arginine, histidine, serine, threonine, alanine, or proline and/or residue 389 is substituted with proline or serine. In some embodiments, residues at one or more of positions 385, 386, 387, and 389 are substituted with arginine, threonine, arginine, and proline, respectively. In some embodiments, residues at one or more of positions 385, 386, and 389 are substituted with aspartic acid, proline, and serine, respectively.

In some embodiments, the anti-Clec12A antibody includes a constant region, Fc region or Fc fragment of an IgG antibody having one or more of the following substitutions: leucine at residue 251, tyrosine or leucine at residue 252, threonine or serine at residue 254, arginine at residue 255, threonine at residue 308, proline at residue 309, serine at residue 311, aspartic acid at residue 312, leucine at residue 314, arginine at residue 385, threonine at residue 386, arginine at residue 387, proline at residue 389, methionine at residue 428, lysine at residue 433, phenylalanine or tyrosine at residue 434, tyrosine at position 435, and/or tyrosine at position 436. Additional amino acid substitutions that can be included in a constant region, Fc region or Fc fragment include those described in, e.g., U.S. Pat. Nos. 6,277,375; 8,012,476; and 8,163,881.

In some embodiments, the anti-Clec12A antibody described herein includes a heavy chain constant domain that includes the Ala-Ala mutation described in, e.g., PCT Publication nos. WO 94/28027 and WO 98/47531; and Xu et al. (2000) Cell Immunol 200:16-26. Thus, in some embodiments, an anti-Clec12A antibody with one or more mutations within the heavy chain constant region including the Ala-Ala mutation has reduced or no effector function. According to these embodiments, the constant region of an anti-Clec12A antibody described herein can comprise a substitution to an alanine at position 234 and/or a mutation to an alanine at position 235 (EU numbering).

As will be understood by those of skill in the art, any such heavy chain constant domain sequence may be readily combined, e.g., by techniques of molecular biology, with any other antibody sequences or domains provided herein or otherwise known in the art, including any framework regions, CDRs, or constant domains, or portions thereof as disclosed herein or otherwise known in the art, as may be present in an antibody or an antigen-binding fragment thereof of any format as disclosed herein or otherwise known in the art.

Exemplary Antibodies

Engineered antibodies can include various heavy chains and light chains described herein. In some embodiments, the anti-Clec12A antibody can include two heavy chains and light chains. In various embodiments, the present disclosure encompasses an antibody including at least one heavy chain and/or light chain as disclosed herein, at least one heavy chain and/or light chain framework domain as disclosed herein, at least one heavy chain and/or light chain CDR domain as disclosed herein, and/or any heavy chain and/or light chain constant domain as disclosed herein.

In various embodiments, the anti-Clec12A antibody disclosed herein is a homodimeric monoclonal antibody. In various embodiments, the anti-Clec12A antibody disclosed herein is a heterodimeric antibody. In various embodiments, the anti-Clec12A antibody is, e.g., a typical antibody or a diabody, triabody, tetrabody, minibody, maxibody, tandab, DVD, BiTe, scFv, TandAb scFv, Fab, $Fab_2$, $Fab_3$, $F(ab')_2$, or the like, or any combination thereof.

In some embodiments, the disclosure provides fusion proteins comprising one or more variable domains or engineered antibodies as described herein, or portion thereof, and one or more additional polypeptides.

Exemplary Single Chain Variable Fragments

In some embodiments, the disclosure provides a single-chain variable fragment. In some embodiments, the scFv is a human scFv. A "single-chain variable fragment" or "scFv" refers to a fusion protein of the variable regions of the heavy ($V_H$) and light chains ($V_L$) of an immunoglobulin (e.g., mouse or human) covalently linked to form a $V_H::V_L$ heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80 (6): 1910-1917 (2008) and WO 2014/087010, the contents of which are hereby incorporated by reference in their entireties. In certain embodiments, the linker is a G4S linker (SEQ ID NO: 78).

Alternatively or additionally, the scFv may be derived from Fab's (instead of from an antibody, e.g., obtained from Fab libraries). In certain embodiments, the anti-Clec12A antibody or antigen-binding fragment thereof is a Fab. In certain embodiments, the Fab is crosslinked. In certain embodiments, the anti-Clec12A antibody or antigen-binding fragment thereof is a F (ab) 2. Any of the foregoing molecules may be comprised in a fusion protein with a heterologous sequence to form an anti-Clec12A antigen antibody or an antigen-binding fragment thereof.

In certain embodiments, the anti-Clec12A antibody or antigen-binding fragment thereof binds to Clec12A (e.g., human Clec12A) with a dissociation constant $(K_D)$ of at least about $1\times10^{-6}$ M, at least about $1\times10^{-7}$ M, at least about $1\times10^{-8}$ M, at least about $1\times10^{-9}$ M, or at least about $1\times10^{-10}$ M. In certain embodiments, the anti-Clec12A antibody or antigen-binding fragment thereof binds to Clec12A (e.g., human Clec12A) with a dissociation constant $(K_D)$ of at least about $2\times10^{-8}$ M. In certain embodiments, the anti-Clec12A antibody or antigen-binding fragment thereof binds to Clec12A (e.g., human Clec12A) with a dissociation constant $(K_D)$ of between about $2\times10^{-8}$ M and about $8\times10^{-9}$ M.

In some embodiments, the anti-Clec12A antibody or antigen-binding fragment thereof binds to Clec12A (e.g., human Clec12A) with a dissociation constant $(K_D)$ between about 1 nM and 50 nM, about 5 nM and 30 nM, about 5 nM and 25 nM, or about 8 nM and 20 nM. In some embodiments, the anti-Clec12A antibody or antigen-binding fragment thereof binds to Clec12A (e.g., human Clec12A) with a dissociation constant $(K_D)$ of at least about 50 nM, at least about 40 nM, at least about 35 nM, at least about 30 nM, at least about 25 nM, at least about 20 nM, at least about 19 nM, at least about 18 nM, at least about 17 nM, at least about 16 nM, at least about 15 nM, at least about 14 nM, at least about 13 nM, at least about 12 nM, at least about 11 nM, at least about 10 nM, at least about 9 nM, at least about 8 nM, at least about 7 nM, at least about 6 nM, at least about 5 nM.

In some embodiments, the anti-Clec12A scFv comprises a sequence consisting of an amino acid sequence having about 80% or more identity to SEQ ID NO: 56, SEQ ID NO: 57, SEQ ID NO: 58, or SEQ ID NO: 59. In some embodiments, the anti-Clec12A scFv comprises a sequence consisting of SEQ ID NO: 56, SEQ ID NO: 57, SEQ ID NO: 58, or SEQ ID NO: 59.

In some embodiments, the anti-Clec12A scFv comprises a linker comprises or consists of the amino acid sequence set forth in SEQ ID NO: 60, which is provided below:

(SEQ ID NO: 60)
GGGGSGGGGSGGGGS

In some embodiments, the linker comprises or consists of the amino acid sequence set forth in SEQ ID NO: 61, which is provided below:

(SEQ ID NO: 61)
GGGGSGGGGSGGGGSGGGGS

In some embodiments, the linker comprises or consists of the amino acid sequence set forth in SEQ ID NO: 62, which is provided below:

(SEQ ID NO: 63)
GGGGSGGGGSGGGGSGGGSGGGGS

In some embodiments, the linker comprises or consists of the amino acid sequence set forth in SEQ ID NO: 63, which is provided below:

(SEQ ID NO: 64)
GGGGSGGGGSGGGGSGGGGSGGGGSGGGGS

In some embodiments, the anti-Clec12A antibody or antigen-binding fragment thereof comprises a conservative sequence modification (e.g., anti-Clec12A antibody or fragment thereof described herein). In some embodiments, the conservative sequence modification is an amino acid modification that does not significantly affect or alter the binding characteristics of the presently disclosed anti-Clec12A antibody or antigen-binding fragment thereof (e.g., the antibody or antigen-binding fragment thereof) comprising the amino acid sequence. Conservative modifications can include amino acid substitutions, additions and deletions. Modifications can be introduced into the anti-Clec12A antibodies or antigen-binding fragments thereof by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; nonpolar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function. In certain embodiments, no more than one, no more than two, no more than three, no more than four, no more than five residues within a specified sequence or a CDR region are altered.

In some embodiments, the light chain and/or heavy chain of the anti-Clec12A scFv comprise a signal peptide. In some embodiments, the signal peptide comprises an amino acid sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% homology or identity to one amino acid sequence selected from METDTLLLWVLLLWVPGSTG (SEQ ID NO: 75), MYRMQLLSCIALSLALVINS (SEQ ID NO: 62), MYSMQLASCVTLTLVLLVNS (SEQ ID NO: 76), MET-PAQLLFLLLLWLPDTTG (SEQ ID NO: 77), MALPVTALLLPLALLLHAARP (SEQ ID NO: 65), MKWVTFISLLESSAYS (SEQ ID NO: 66), MDSKGSSQKGSRLLLLLVVSNLLLCQGVVS (SEQ ID NO: 67). In some embodiments, the signal sequence is METDTLLLWVLLLWVPGSTG (SEQ ID NO: 75). In some embodiments, the signal sequence is MYRMQLLS-CIALSLALVTNS (SEQ ID NO: 62). In some embodiments, the signal sequence is MYSMQLASCVTLTLVLLVNS (SEQ ID NO: 76). In some embodiments, the signal sequence is METPAQLLFLLLLWLPDTTG (SEQ ID NO: 77). In some embodiments, the signal sequence is MALPVTALLLPLALLLHAARP (SEQ ID NO: 65). In some embodiments, the signal sequence is MKWVTFISL-LESSAYS (SEQ ID NO: 66).

In some embodiments, the anti-Clec12A scFv comprises an amino acid sequence of

```
                                 (SEQ ID NO: 56)
QVQLQESGPGLVKPSETLSLTCTVSGGSISTYYWSWIRQPPGKGLEWIGY

IYYSGSTKYNPSLKSRVTISVDTSKNLFSLKLSSVTAADTAVYYCAREDY

YGSGSPFDYWGQGTLVTVSSASTGGGGSGGGGSGGGGSAIQMTQSPSSLS

ASVGDRVTITCRASQGIRYDLGWYQQKPGKAPKLLIYAASSLQSGVPSRF

SGSGSGTDFTLTISSLQPEDFATYYCLQDYNFPRTFGQGTKVEIK;

(SEQ ID NO: 57)
QVQLVESGGGVVQPGRSLRLSCAASGFTFSSYGMHWVRQAPGKGLEWVAI

VISYDGSDKYYVDSVKGRFTISRDNSKNTLYLHMNSLRAEDTAVYYCARD

KGYYFDYWGQGTLVTVSSASTGGGGSGGGGSGGGGSEIVMTQSPATLSLS

PGERATLSCRASQSVGNRYLSWYQQKPGQAPRLLIYGASTRATGIPARFS

GSGSGTDFTLTISSLQPEDFAVYYCQQDYNLPLTFGGGTKVEIK;

(SEQ ID NO: 58)
QVQLVESGGGVVQPGRSLRLSCAASGFTFSSYGMHWVRQAPGKGLEWVAV

ISYDGSDKYSADSVKGRFNISRDNSKNTLYLQMNSLRAEDTAVYYCARDG

SRYFDYWGQGTLVTVSSASTGGGGSGGGGSGGGGSEIFMTQSPATLSLPG

ERATLSCRASQSVHSKYLSWYQQKPGQAPSLLIYGASTRATGIPARFSGS

GSGTDFTLTISSLQPEDFAVYYCQQDYNLPITFGQGTRLEIK;
or (SEQ ID NO: 59)
QLQLQESGPGLVKPSETLSLTCTVSGGSISSSTYYWGWIRQPPRKGLEWI

GSTHYRGSTYYNPSLKSRVTISVDTSKNQFSLKVSSVTAADTAVYYCARE

LTGEVFDYWGQGTLVTVSSASTGGGGSGGGGSGGGGSDIQMTQSPSSLSA

SVGDRVTITCRASQSISSYLNWYQQKPGKAPKLLIYAASSLQSGVPSRFS

GSGSGTDFTLTISSLQPEDFATYYCQQSYSTPFTFGPGTKVDIK.
```

In some embodiments, anti-Clec12A scFv comprises an amino acid sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% homology or identity to any one of SEQ ID Nos: 56-59.

In some embodiments, the anti-Clec12A scFv comprises an amino acid sequence set forth in SEQ ID No: 56. In some embodiments, the anti-Clec12A scFv comprises an amino acid sequence set forth in SEQ ID No: 57. In some embodiments, the anti-Clec12A scFv comprises an amino acid sequence set forth in SEQ ID No: 58. In some embodiments, the anti-Clec12A scFv comprises an amino acid sequence set forth in SEQ ID No: 59.

Nucleotide Sequences

The present disclosure includes nucleotide sequences encoding one or more heavy chains, heavy chain variable domains, heavy chain framework regions, heavy chain CDRs, heavy chain constant domains, light chains, light chain variable domains, light chain framework regions, light chain CDRs, light chain constant domains, or other immunoglobulin-like sequences, or antibodies disclosed herein. In various embodiments, such nucleotide sequences may be present in a vector. In various embodiments such nucleotides may be present in the genome of a cell, e.g., a cell of a subject in need of treatment or a cell for production of an antibody, e.g. a mammalian cell for production of a an antibody.

Engineered Antibodies and Fusion Proteins

In some embodiments, the disclosure provides fusion proteins comprising (i) one or more antigen-binding regions described herein (e.g., antigen-binding region of immunoglobulin, heavy chain antibody, light chain antibody, LRR-based antibody, or other protein scaffold with antibody-like properties, as well as other antigen binding moiety known in the art, including, e.g., a Fab, Fab', Fab'$_2$, Fab$_2$, Fab$_3$, F(ab')$_2$, Fd, Fv, Feb, scFv, SMIP, antibody, diabody, triabody, tetrabody, minibody, maxibody, tandab, DVD, BiTe, TandAb, or the like), e.g., one or more variable domains described herein, or portion thereof (e.g., one or more CDRs described herein), and (ii) one or more additional polypeptides. For example, albumin is an abundant serum protein that is protected from degradation by pH-dependent recycling mediated by interaction with FcRn. In some embodiments, one or more variable domains or engineered antibodies as described herein, or portion thereof (e.g., one or more CDRs described herein) is fused to albumin, a portion thereof (such as a portion of albumin that binds to an FcRn), and/or an engineered variant of albumin that binds to FcRn with improved affinity. In other instances, one or more variable domains or engineered antibodies as described herein, or portion thereof (e.g., one or more CDRs described herein) is fused to a polypeptide that binds to albumin to form a fusion protein-albumin complex, which can in turn bind to an FcRn. In some embodiments, the polypeptide that binds to albumin is a single chain variable fragment (scFv). The albumin or portion thereof can include a mutation of one or more amino acids that can modify its binding to an FcRn. Such mutations are known in the art (see, e.g., Andersen et al., *Nature Communications* 3:610 doi: 10.1038/nocmms 1607 (2012)). In other instances, one or more variable domains or engineered antibodies described herein, or portion thereof (e.g., one or more CDRs described herein) is fused to transferrin. Transferrin is recycled by binding to a transferrin receptor (see, e.g., Widera et al., *Adv. Drug Deliv. Rev.* 55:1439-66 (2003)).

Engineered Antibodies and Fragments Thereof

Anti-Clec12A antibodies and antigen-binding fragments thereof according to the present disclosure are engineered to include one or more binding moieties that specifically bind one or more targets of interest. Clec12A antibodies and antigen-binding fragments thereof encompass nucleic acids (e.g., RNA and DNA), proteins (e.g., antibodies), and combination thereof. In some embodiments, pH-dependent binding moieties can be or include, for example, nucleic acids (e.g., RNA and DNA) and aptamers, polypeptides (e.g., antibodies or fragments thereof, albumin, receptors, ligands, signal peptides, avidin, and Protein A), polysaccharides, biotin, hydrophobic groups, hydrophilic groups, drugs, and any organic molecules that bind to receptors.

Antibody or Fragment Thereof as Binding Moieties

In some embodiments, an antibody or fragment thereof described herein is an anti-Clec12A antibody. In some instances, one or more binding moieties described herein are or include antibodies, antigen-binding fragments thereof, and/or Fc regions (or Fc fragments) thereof. The basic structure of an IgG antibody consists of two identical light polypeptide chains and two identical heavy polypeptide chains linked together by disulfide bonds. The first domain located at the amino terminus of each chain is variable in amino acid sequence, providing antibody binding specificities found in each individual antibody. These are known as heavy chain variable (VH) and light chain variable (VL) regions. The other domains of each chain are relatively invariant in amino acid sequence and are known as constant heavy (CH) and constant light (CL) regions. For an IgG antibody, the light chain includes one variable region (VL) and one constant region (CL). An IgG heavy chain includes a variable region (VH), a first constant region (CH1), a hinge region, a second constant region (CH2), and a third constant region (CH3). In IgE and IgM antibodies, the heavy chain includes an additional constant region (CH4).

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), minibodies, domain antibodies, synthetic antibodies (sometimes referred to as "antibody mimetics"), and antigen-binding fragments of any of the above. In certain embodiments, antibodies described herein refer to polyclonal antibody populations.

The term "Fc fragment", as used herein, refers to one or more fragments of an Fc region that retains an Fc function and/or activity described herein, such as binding to an Fc receptor. The term "antigen binding fragment" of an antibody, as used herein, refers to one or more fragments of an antibody that retain the ability to specifically bind to an antigen. Examples of binding fragments encompassed within the term "antigen binding fragment" of an antibody include a Fab fragment, a F(ab')$_2$ fragment, a Fd fragment, a Fv fragment, a scFv fragment, a dAb fragment (Ward et al., (1989) Nature 341:544-546), and an isolated complementarity determining region (CDR). These antibody fragments can be obtained using conventional techniques known to those with skill in the art, and fragments can be screened for utility in the same manner as are intact antibodies.

In some aspects, the present invention provides antibodies or antigen-binding fragments thereof that bind to human Clec12A comprising human heavy and/or light constant regions, wherein the human heavy constant region comprises an isotypic variant comprising the Fc region of human IgG1, human IgG2, human IgG3, or human IgG4.

In a further aspect, the present invention provides a humanized antibody or fragment thereof that binds to human Clec12A, wherein the antibody comprises a variant human IgG Fc region which comprises amino acid substitution S324N replacing serine at amino acid position 324 of the parent antibody with asparagine, whereas the antibody comprising the variant human IgG Fc region exhibits improved complement dependent cytotoxicity (CDC) compared to the parent antibody.

Antibodies or fragments can be produced by any method known in the art for synthesizing antibodies (see, e.g., Harlow et al., Antibodies: A Laboratory Manual, (Cold Spring Harbor Laboratory Press, 2nd ed. 1988); Brinkman et al., 1995, J. Immunol. Methods 182:41-50; WO 92/22324; WO 98/46645). Chimeric antibodies can be produced using methods described in, e.g., Morrison, 1985, Science 229: 1202, and humanized antibodies by methods described in, e.g., U.S. Pat. No. 6,180,370.

Additional compositions and methods described herein are bispecific antibodies and multivalent antibodies, as described in, e.g., Segal et al., J. Immunol. Methods 248:1-6 (2001); and Tutt et al., J. Immunol. 147:60 (1991).

Engineered Antigen Binding Regions

In some embodiments, a binding moiety is or includes an antibody (e.g., an IgG antibody, e.g., an IgG1, IgG2, or IgG3 antibody), or an antigen binding fragment, engineered to bind to a target (i.e., antigen) in an altered manner (e.g., in a pH sensitive manner, e.g., in a more or less pH sensitive manner) relative to a reference antibody or antigen binding fragment. For example, an antibody can be engineered by modifying (e.g., by adding, deleting, or substituting) an amino acid within one or more antibody CDRs and/or at a position involved in antibody CDR structure. Exemplary, non-limiting sites of an antibody that can be modified include the following (amino acid positions are indicated based on the Kabat numbering (Kabat et al., (1991) Sequences of Proteins of Immunological Interest, NIH)).

Heavy chain: H27, H31, H32, H33, H35, H50, H58, H59, H61, H62, H63, H64, H65, H99, H100b, and H102

Light chain: L24, L27, L28, L32, L53, L54, L56, L90, L92, and L94.

In some embodiments, one or more of these disclosed amino acids can be substituted with histidine, arginine, lysine, aspartic acid, glutamic acid, serine, threonine, asparagine, or glutamine. Without wishing to be bound by theory, it is believed that substituting an amino acid at one or more of these positions with a histidine can result in an antibody having pH-dependent antigen-binding properties. In some embodiments, a non-histidine residue is substituted with a histidine residue. In some embodiments, a histidine residue is substituted with a non-histidine residue. Additional engineered antigen binding regions include those described in, e.g., U.S. Publ. No. 20110229489.

Engineered Constant Regions

In some instances, a binding moiety is or includes an antibody constant region, Fc region or Fc fragment that binds one or more Fc receptors (e.g., FcγRI, FcγRIIA, FcγRIIB, FcγRIIIA, FcγRIIIB, FcγRIV, or FcRn receptor). In some embodiments, a constant region, Fc region or Fc fragment is engineered to bind to a target (e.g., an Fc receptor) in an altered manner (e.g., in a pH sensitive manner, e.g., in a more or less pH sensitive manner) relative to a reference constant region, Fc region or Fc fragment.

In some instances, a binding moiety can be or include a constant region, Fc region or Fc fragment of an IgG antibody engineered to include an amino acid addition, deletion, or substitution, of one or more amino acid residues described herein (e.g., 251-256, 285-290, 308-314, 385-389, and 428-436 (Kabat numbering (Kabat et al., (1991) Sequences of Proteins of Immunological Interest, NIH))).

Producing Clec12A Antibodies and Fragments Thereof

In some embodiments, an antibody or fragment thereof described herein is engineered to include one or more binding moieties that exhibit binding to one or more targets by mutagenesis using known techniques. For example, a sequence of a reference polypeptide (e.g., a therapeutic antibody or therapeutic fusion protein) can be obtained, and one or more amino acid residues can be added, deleted, or substituted. In some embodiments, one or more amino acid residues are substituted with histidine, arginine, lysine, aspartic acid, glutamic acid, serine, threonine, asparagine, or glutamine. In some embodiments, one or more amino acids are substituted with histidine.

In some embodiments, substitution of an amino acid residue with a histidine results in insertion of a protonation site, which can increase pH sensitivity of a binding moiety. Polypeptides can be produced using standard methods and assayed for binding to targets of interest as described herein. Additional methods of increasing pH sensitivity of a binding moiety are described in, e.g., Sarkar et al., Nature Biotechnology 20:908-913 (2002); Murtaugh et al., Protein Science 20:1619-1631 (2011); and U.S. Publ. No. 20110229489.

In some embodiments, a first target of interest is selected, and an antibody that selectively binds to the target is provided, obtained, and/or produced (e.g., using known methods as described herein). One or more amino acids of an antigen-binding region and/or an Fc region are substituted (e.g., with histidine, arginine, lysine, aspartic acid, glutamic acid, serine, threonine, asparagine, or glutamine), and pH sensitivity of binding to the target (and, additionally or alternatively, to FcRn) is determined.

In some embodiments, a polypeptide that naturally binds to a target of interest is provided, obtained, and/or produced. The polypeptide is conjugated to an Fc region or Fc fragment described herein (e.g., which binds to FcRn with a desired binding affinity) using known methods. For example, the polypeptide and Fc region or Fc fragment can be conjugated by chemical means or by recombinant expression as a fusion protein. Additionally or alternatively, one or more amino acids of the polypeptide can be substituted (e.g., with histidine, arginine, lysine, aspartic acid, glutamic acid, serine, threonine, asparagine, or glutamine), and pH sensitivity of binding of the polypeptide and the target is determined.

In some embodiments, an antibody or fragment thereof described herein is engineered to include one or more binding moieties identified and/or selected by screening. For example, an antigen-binding moiety that binds antigen can be identified using a library, e.g., a phage library, expressing antigen-binding moieties. Methods of screening recombinant antibody libraries are known (see, e.g., Hoogenboom, Nature Biotech. 23:1105-1116 (2005); U.S. Pat. Nos. 5,837,500; 5,571,698; WO 2012/044831).

PEGylation

In certain embodiments, the anti-Clec12A antibody as described herein can be PEGylated to include mono- or poly-(e.g., 2-4) PEG moieties. Such PEGylated antibodies may display increased half-life in comparison to a non-PEGylated reference antibody, e.g., an antibody having the same amino acid sequence but different, a different amount of, or no PEGylation.

PEGylation can be carried out by any suitable reaction known in the art. Methods for preparing a PEGylated protein can generally include (a) reacting a polypeptide with polyethylene glycol (such as a reactive ester or aldehyde derivative of PEG) under conditions whereby the polypeptide becomes attached to one or more PEG groups; and (b) obtaining the reaction product(s). In general, the conditions for the reactions can be determined case by case based on known parameters and the desired result.

There are a number of PEG attachment methods available to those skilled in the art. For example, the step of PEGylating an antibody or fragment thereof described herein can be carried out via an acylation reaction or an alkylation reaction with a reactive polyethylene glycol molecule.

Measuring Interactions of Binding Moieties and Targets

The binding properties of an antibody or fragment thereof described herein (e.g., an anti-Clec12A antibody described herein) to a target (e.g., Clec12A) can be measured by methods known in the art, e.g., one of the following methods: BIACORE analysis, Enzyme Linked Immunosorbent Assay (ELISA), x-ray crystallography, sequence analysis and scanning mutagenesis. The binding interaction of an antibody and Clec12A and/or FcRn can be analyzed using surface plasmon resonance (SPR). SPR or Biomolecular Interaction Analysis (BIA) detects bio-specific interactions in real time, without labeling any of the interactants. Changes in the mass at the binding surface (indicative of a binding event) of the BIA chip result in alterations of the refractive index of light near the surface. The changes in the refractivity generate a detectable signal, which are measured as an indication of real-time reactions between biological molecules. Methods for using SPR are described, for example, in U.S. Pat. No. 5,641,640; Raether (1988) Surface Plasmons Springer Verlag; Sjolander and Urbaniczky (1991) Anal. Chem. 63:2338-2345; Szabo et al. (1995) Curr. Opin. Struct. Biol. 5:699-705 and on-line resources provide by BIAcore International AB (Uppsala, Sweden). Additionally, a KinExA® (Kinetic Exclusion Assay) assay, available from Sapidyne Instruments (Boise, Id.) can also be used.

Information from SPR can be used to provide an accurate and quantitative measure of the equilibrium dissociation constant ($K_D$), and kinetic parameters, including $K_{on}$ and $K_{off}$, for the binding of a binding moiety to a target (e.g., an anti-Clec12A antibody to Clec12A and/or FcRn). Such data can be used to compare different molecules. Information from SPR can also be used to develop structure-activity relationships (SAR). For example, the kinetic and equilibrium binding parameters of particular binding moieties to targets at various pH levels can be evaluated. Variant amino acids at given positions can be identified that correlate with particular binding parameters, e.g., high affinity, low affinity, and slow $K_{off}$ at particular pH levels.

Methods of Treatment

In some embodiments, an anti-Clec12A antibody or antigen-binding fragment thereof described herein is used in a method of treating one or more Clec12A-associated conditions. In some embodiments, an anti-Clec12A antibody or antigen-binding fragment thereof as described herein is for use as a medicament. Clec12A-associated conditions can include, without limitation, conditions that are caused by, include, include symptoms resulting in whole or in part from, or are known to occur in conjunction with Clec12A expression.

In some aspects, the present invention provides a method for treating a cancer comprising administering an anti-Clec12A antibody or antigen-binding fragment thereof described herein. A cancer is a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. In some embodiments, the "cancer" or "cancer tissue" comprises a solid tumor. Examples of cancers that can be treated by the methods of the present invention include, but are not limited to, cancers of the immune system including lymphoma, leukemia, myeloma, and other leukocyte malignancies. In some embodiments, the cancer is acute myeloid leukemia. In some embodiments, the cancer is relapsed and refractory acute myeloid leukemia.

In some embodiments, the lymphoma is selected from the group consisting of Acute Lymphoblastic Leukemia (ALL), AIDS-related lymphoma, ALK-positive large B-cell lymphoma, Burkitt's lymphoma, Chronic lymphocytic leukemia (CLL), Classical Hodgkin lymphoma, Diffuse large B-cell lymphoma (DLBCL), Follicular lymphoma, Intravascular large B-cell lymphoma, Large B-cell lymphoma arising in HHV8-associated multicentric Castleman's disease, Lymphomatoid granulomatosis, Lymphoplasmacytic lymphoma, Mantle cell lymphoma (MCL), Marginal zone B-cell lymphoma (MZL), Mucosa-Associated Lymphatic Tissue lymphoma (MALT), Nodal marginal zone B cell lymphoma (NMZL), Nodular lymphocyte predominant Hodgkin's lymphoma, Non-Hodgkin's lymphoma, Plasmablastic lymphoma, Primary central nervous system lymphoma, Primary effusion lymphoma, Splenic marginal zone lymphoma (SMZL), and Waldenstrom's macroglobulinemia. In some embodiments, the lymphoma is selected from the group consisting of Acute Lymphoblastic Leukemia (ALL), Chronic lymphocytic leukemia, CLL), Diffuse large B-cell lymphoma (DLBCL), Follicular lymphoma, Mantle cell lymphoma (MCL), Marginal zone B-cell lymphoma (MZL), Mucosa-Associated Lymphatic Tissue lymphoma (MALT), and Non-Hodgkin's lymphoma. In some embodiments, the lymphoma is Non-Hodgkin's lymphoma. In some embodiments, the cancer is relapsed and refractory acute myeloid leukemia.

In certain embodiments, the tumor is a cancer. In certain embodiments, the tumor is blood cancer. In certain embodiments, the tumor is selected from the group consisting of multiple myeloma, leukemia, lymphomas, and myeloid malignancies. Non-limiting examples of blood cancer include multiple myeloma, leukemia, and lymphomas. Non-limiting examples of leukemia include acute myeloid leukemia (AML), chronic myeloid leukemia (CML), acute lymphocytic leukemia (ALL), chronic lymphocytic leukemia (CLL), acute promyelocytic leukemia (APL), mixed-phenotype acute leukemia (MLL), hairy cell leukemia, and B cell prolymphocytic leukemia. The lymphoma can be Hodgkin's lymphoma or non-Hodgkin's lymphoma. Non-limiting examples of myeloid malignancies include myelodysplastic syndromes (MDS), myeloproliferative neoplasms (MPN), myeloid/lymphoid neoplasms (e.g., myeloid/lymphoid neoplasms with eosinophilia and rearrangement of Platelet Derived Growth Factor Receptor Alpha (PDGFRA), Platelet Derived Growth Factor Receptor Beta (PDGFRB), or Fibroblast Growth Receptor I (FGFR1), or with PCM1-JAK2), acute myeloid leukemia (AML), blastic plasmacytoid dendritic cell neoplasm, B-lymphoblastic leukemia/lymphoma, and T-lymphoblastic leukemia/lymphoma. In certain embodiments, the myeloid malignancies comprises myelodysplastic syndromes.

In certain embodiments, the tumor is a B cell malignancy. Non-limiting examples of B cell malignancy include B cell lymphoma (BCL), B cell acute lymphocytic leukemia (ALL), B cell chronic lymphocytic leukemia (CLL), multiple myeloma (MM), CLL with Richter's transformation, and CNS lymphoma. B cell lymphoma includes B cell non-Hodgkin lymphoma (NHL) and B cell Hodgkin's lymphoma.

In various embodiments, administration of an anti-Clec12A antibody or antigen-binding fragment thereof described herein or fragment thereof results in a decrease in the prevalence, frequency, level, and/or amount of one or more symptoms or biomarkers of a Clec12A-associated condition as described herein or otherwise known in the art, e.g., a decrease of at least 3%, 4%, 5%, 6%, 7%, 8%, 9%, 10%, 15%, 20%, 25%, 30%, 35%, 40%, 45%, 50%, 60%, 70%, 80%, 90%, 95%, 99%, or 100% of one or more symptoms or biomarkers as compared to a prior measurement in the subject or to a reference value.

In some embodiments, administration of an anti-Clec12A antibody or antigen-binding fragment thereof described herein to a subject having cancer results in a greater decrease or improvement in one or more symptoms or biomarkers of cancer than does a reference antibody e.g., an antibody that cross-competes for Clec12A binding, under comparable conditions In some embodiments, an anti-Clec12A antibody or antigen-binding fragment thereof as described herein exhibits a decreased effective dose as compared to a reference protein (e.g., an antibody that cross-competes for Clec12A binding). For instance, an effective dose of an anti-Clec12A antibody as described herein may be, e.g., less than 1,000 mg/dose, e.g., less than 900 mg/dose, 800 mg/dose, 700 mg/dose, 600 mg/dose, 500 mg/dose, 550 mg/dose, 400 mg/dose, 350 mg/dose, 300 mg/dose, 200 mg/dose, 100 mg/dose, 50 mg/dose, 25 mg/dose, or less. In certain instances, an effective dose of an anti-Clec12A antibody as disclosed herein is lower than an effective or recommended or approved dosage of a reference antibody, which dosage of a reference antibody may be, e.g., 900 mg/dose or 600 mg/dose. Alternatively or in combination with a dosage as disclosed herein, an anti-Clec12A antibody as described herein may be effectively or usefully administered at a frequency that is less than once per week, e.g., less than once every week, 2 weeks, 3 weeks, 4 weeks, 5 weeks, 6 weeks, 7 weeks, 8 weeks, 9 weeks, 10 weeks, 11 weeks, 12 weeks, 3 months, 4 months, 5 months, 6 months, 7 months, 8 months, 9 months, 10 months, 11 months, or year. In certain instances, an effective or useful administration frequency of an anti-Clec12A antibody as disclosed herein is lower than an effective or recommended or approved administration frequency of a reference antibody, which administration frequency can be administered weekly (e.g., at a dosage of 300-600 mg, depending on weight of subject) or every two weeks (e.g., at a dosage of 300-1200 mg, depending on weight of subject).

In some embodiments, an anti-Clec12A antibody or antigen-binding fragment thereof described herein can be administered at a decreased dose amount as compared to a reference protein, e.g., an antibody that cross-competes for Clec12A binding, while achieving an equal, equally effective, comparably effective, or substantially effective outcome, where the anti-Clec12A antibody is administered in an identical, equivalent, or substantially equivalent formulation and/or by an identical, equivalent, or substantially equivalent route of administration as the reference (e.g., an antibody that cross-competes for Clec12A binding). In some embodiments, an anti-Clec12A antibody described herein can be administered at an increased interval as compared to a reference antibody (e.g., an antibody that cross-competes for Clec12A binding) while achieving an equal, equally effective, comparably effective, or substantially effective outcome, where the anti-Clec12A antibody is administered in an identical, equivalent, or substantially equivalent formulation and/or by an identical, equivalent, or substantially equivalent route of administration as the reference. In some embodiments, an anti-Clec12A antibody described herein can be administered in a decreased number of unit dosages, and/or for a decreased period of treatment, as compared to a reference antibody while achieving an equal, equally effective, comparably effective, or substantially effective outcome, where the anti-Clec12A antibody is administered in an identical, equivalent, or substantially equivalent formulation and/or by an identical, equivalent, or substantially equivalent route of administration as the reference (e.g., an antibody that cross-competes for Clec12A binding).

In accordance with some such embodiments, an administered dose of an anti-Clec 12A antibody described herein may be less likely to elicit an adverse response when administered to a subject, e.g., an adverse immune response, than would an effective dose of a reference antibody, e.g., e.g., an antibody that cross-competes for Clec12A binding. Accordingly, in various embodiments, an anti-Clec12A antibody as disclosed herein may be less likely than a reference antibody, per unit of activity administered to induce an adverse reaction or side effect. In various embodiments, an anti-Clec12A antibody as disclosed herein may less likely than a reference antibody, per unit of activity administered, to induce an adverse reaction or side effect having a particular degree of severity. In various embodiments, an anti-Clec12A antibody as disclosed herein may induce one or more adverse reactions or side effects to a lesser degree or in fewer patients than a reference antibody, per unit of activity administered. Examples of adverse reactions or side effects that may be associated with the administration of an antibody capable of binding Clec12A, may include headache, nasopharyngitis, back pain, nausea, diarrhea, hypertension, upper respiratory infection, abdominal pain, vomiting, anemia, cough, peripheral edema, and/or urinary tract infection.

In some embodiments, upon administration to a subject (e.g., at a single dose), an anti-Clec12A antibody or antigen-binding fragment thereof described herein is measured at an increased level in plasma at a defined time following administration (e.g., 1, 2, 3, 4, 5, 6, 7, 8, 9, 10, 11, 12, 13, 14, or more days), relative to level of a control at the same defined time (e.g., an antibody that cross-competes for Clec12A binding). For example, at a defined time following administration of a single dose, a level of an anti-Clec12A antibody described herein is at least 10%, 20%, 30%, 40%, 50%, 60%, 70%, 80%, 90%, 100%, 150%, 200%, 300%, 400%, or 500% higher than a corresponding level of a reference antibody.

In some embodiments, an anti-Clec12A antibody or antigen-binding fragment thereof described herein is measured at an increased level in plasma at a defined time (e.g., 1, 2, 3, 4, 5, 6, 7, 8, 9, 10, 11, 12, 13, 14, or more days) following administration (e.g., of a single dose), relative to level of a control at the same defined time. For example, at a defined time following administration, a level of an anti-Clec12A antibody described herein is at least 10%, 20%, 30%, 40%, 50%, 60%, 70%, 80%, 90%, 100%, 150%, 200%, 300%, 400%, or 500% higher than a corresponding level of a reference antibody.

In some embodiments, an anti-Clec12A antibody described herein has increased half-life (e.g., relative to a control, e.g., a reference antibody, e.g., an antibody that cross-competes for Clec12A binding), and thus the anti-Clec12A antibody can be administered to a subject at increased inter-dose intervals. For example, an anti-Clec12A antibody can be administered once every week, every two weeks, every three weeks, every four weeks, every 6 weeks, every 8 weeks, or longer duration.

In some embodiments, a therapeutically effective amount of an anti-Clec12A antibody or antigen-binding fragment thereof described herein is about 90%, 80%, 70%, 60%, 50%, 40%, 30%, 20%, 10%, or 5% of an effective amount of a reference therapeutic protein, e.g., an antibody that cross-competes for Clec12A binding). In some embodiments, a single dose of an anti-Clec12A antibody or antigen-binding fragment thereof described herein achieves a comparable therapeutic effect as two or more doses of a reference antibody.

In some embodiments, an anti-Clec12A antibody or antigen-binding fragment thereof described herein is administered at a dose that is about 90%, 80%, 70%, 60%, 50%, 40%, 30%, 20%, 10%, or 5% of the concentration of a target antigen (e.g., Clec12A) in the subject.

In some embodiments, an anti-Clec12A antibody or antigen-binding fragment thereof described herein can be physical introduced to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, including a topical, epidermal or mucosal route of administration, for example, intranasally, vaginally, rectally, sublingually or topically. Administering can also be performed, for example, once, a plurality of times, and/or over one or more extended periods.

In some embodiments, an anti-Clec12A antibody or antigen-binding fragment thereof described herein can be used in a number of diagnostic and therapeutic applications. For example, detectably-labeled versions of engineered antibodies as described herein can be used in assays to detect the presence or amount of the Clec12A in a sample (e.g., a biological sample). Engineered antibodies described herein can be used in in vitro assays for studying binding to Clec12A. In some embodiments, an anti-Clec12A antibody described herein can be used as a positive control in an assay designed to identify additional novel compounds that are otherwise are useful for treating a Clec12A-associated disorder. For example, an anti-Clec 12A antibody described herein can be used as a positive control in an assay to identify additional compounds (e.g., small molecules, aptamers, or antibodies) that bind to Clec12A.

The anti-Clec12A antibodies or antigen-binding fragments thereof described herein may be used in monitoring a subject, e.g., a subject having, suspected of having, at risk of developing, or under treatment for one or more Clec12A-associated conditions. Monitoring may include determining the amount or activity of Clec12A in a subject, e.g., in the serum of a subject. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration of an anti-Clec12A antibody as described herein. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a Clec12A-associated disorder described herein.

Formulations and Administration

In various embodiments, antibodies or antigen-binding fragments thereof described herein (e.g., an anti-Clec12A antibody described herein) can be incorporated into a pharmaceutical composition. Such a pharmaceutical composition can be useful, e.g., for the prevention and/or treatment of diseases, e.g., a Clec12A-associated disorder. Pharmaceutical compositions can be formulated by methods known to those skilled in the art (such as described in Remington's Pharmaceutical Sciences, 17th edition, ed. Alfonso R. Gennaro, Mack Publishing Company, Easton, Pa. (1985)).

A suitable means of administration can be selected based on the age and condition of a subject. A single dose of the pharmaceutical composition containing an antibody or fragment thereof described herein (e.g., an anti-Clec12A antibody described herein) can be selected from a range of 0.001 to 1000 mg/kg of body weight. On the other hand, a dose can be selected in the range of 0.001 to 100000 mg/body weight, but the present disclosure is not limited to such ranges. The dose and method of administration varies depending on the weight, age, condition, and the like of the patient, and can be suitably selected as needed by those skilled in the art.

In various embodiments, a pharmaceutical composition can be formulated to include a pharmaceutically acceptable carrier or excipient. Examples of pharmaceutically acceptable carriers include, without limitation, any and all solvents, dispersion media, coatings, antibacterial and antifungal agents, isotonic and absorption delaying agents, and the like that are physiologically compatible. Compositions of the present invention can include a pharmaceutically acceptable salt, e.g., an acid addition salt or a base addition salt.

In various embodiments, a composition including an antibody as described herein, e.g., a sterile formulation for injection, can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50 and the like.

As disclosed herein, a pharmaceutical composition may be in any form known in the art. Such forms include, e.g., liquid, semi-solid and solid dosage forms, such as liquid solutions (e.g., injectable and infusible solutions), dispersions or suspensions, tablets, pills, powders, liposomes and suppositories.

Selection or use of any particular form may depend, in part, on the intended mode of administration and therapeutic application. For example, compositions containing a composition intended for systemic or local delivery can be in the form of injectable or infusible solutions. Accordingly, the compositions can be formulated for administration by a parenteral mode (e.g., intravenous, subcutaneous, intraperitoneal, or intramuscular injection). As used herein, parenteral administration refers to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

Route of administration can be parenteral, for example, administration by injection, transnasal administration, transpulmonary administration, or transcutaneous administration. Administration can be systemic or local by intravenous injection, intramuscular injection, intraperitoneal injection, subcutaneous injection.

In various embodiments, a pharmaceutical composition of the present invention can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

A pharmaceutical composition can be administered parenterally in the form of an injectable formulation comprising a sterile solution or suspension in water or another pharmaceutically acceptable liquid. For example, the pharmaceutical composition can be formulated by suitably combining therapeutic molecule with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in the pharmaceutical preparations is such that a suitable dose within the designated range is provided. Nonlimiting examples of oily liquid include sesame oil and soybean oil, and it may be combined with benzyl benzoate or benzyl alcohol as a solubilizing agent. Other items that may be included are a buffer such as a phosphate buffer, or sodium acetate buffer, a soothing agent such as procaine hydrochloride, a stabilizer such as benzyl alcohol or phenol, and an antioxidant. The formulated injection can be packaged in a suitable ampule.

In some embodiments, a composition can be formulated for storage at a temperature below 0° C. (e.g., −20° C. or −80° C.). In some embodiments, the composition can be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.'). Thus, in some embodiments, the compositions described herein are stable in storage for at least 1 year at 2-8° C. (e.g., 4° C.).

In particular instances, a pharmaceutical composition can be formulated as a solution. In some embodiments, a composition can be formulated, for example, as a buffered solution at a suitable concentration and suitable for storage at 2-8° C. (e.g., 4° C.).

Compositions including one or more engineered antibodies as described herein can be formulated in immunoliposome compositions. Such formulations can be prepared by methods known in the art. Liposomes with enhanced circulation time are disclosed in, e.g., U.S. Pat. No. 5,013,556.

In certain embodiments, compositions can be formulated with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

In some embodiments, compositions can be formulated in a composition suitable for intrapulmonary administration (e.g., for administration via an inhaler or nebulizer) to a mammal such as a human. Methods for formulating such compositions are well known in the art. Dry powder inhaler formulations and suitable systems for administration of the formulations are also known in the art. Pulmonary administration may be oral and/or nasal. Examples of pharmaceutical devices for pulmonary delivery include metered dose inhalers, dry powder inhalers (DPIs), and nebulizers. For example, a composition described herein can be administered to the lungs of a subject by way of a dry powder inhaler. These inhalers are propellant-free devices that deliver dispersible and stable dry powder formulations to the lungs. Dry powder inhalers are well known in the art of medicine and include, without limitation: the TURBO-HALER® (AstraZeneca; London, England) the AIR® inhaler (ALKERMES®; Cambridge, Mass.); ROTAHALER® (GlaxoSmithKline; London, England); and ECLIPSE™ (Sanofi-Aventis; Paris, France). See also, e.g., PCT Publication Nos. WO 04/026380, WO 04/024156, and WO 01/78693. DPI devices have been used for pulmonary administration of polypeptides such as insulin and growth hormone. In some embodiments, a composition described herein can be intrapulmonarily administered by way of a metered dose inhaler. These inhalers rely on a propellant to deliver a discrete dose of a compound to the lungs. Additional devices and intrapulmonary administration methods are set forth in, e.g., U.S. Patent Application Publication Nos. 20050271660 and 20090110679, the disclosures of each of which are incorporated herein by reference in their entirety.

In some embodiments, compositions can be formulated for delivery to the eye, e.g., in the form of a pharmaceutically acceptable solution, suspension or ointment. A preparation for use in treating an eye can be in the form of a sterile aqueous solution containing, e.g., additional ingredients such as, but not limited to, preservatives, buffers, tonicity agents, antioxidants and stabilizers, nonionic wetting or clarifying agents, and viscosity-increasing agents. A preparation as described herein can be administered topically to the eye of the subject in need of treatment (e.g., a subject afflicted with AMD) by conventional methods, e.g., in the form of drops, or by bathing the eye in a therapeutic solution, containing one or more compositions.

A variety of devices for introducing drugs into the vitreous cavity of the eye may be appropriate, in certain embodiments, for administration of a composition as described herein. For example, U.S. Publication No. 2002/0026176 describes a pharmaceutical-containing plug that can be inserted through the sclera such that it projects into the vitreous cavity to deliver the pharmaceutical agent into the vitreous cavity. In another example, U.S. Pat. No. 5,443,505 describes an implantable device for introduction into a suprachoroidal space or an avascular region for sustained release of drug into the interior of the eye. U.S. Pat. Nos. 5,773,019 and 6,001,386 each disclose an implantable drug delivery device attachable to the scleral surface of an eye. Additional methods and devices (e.g., a transscleral patch and delivery via contact lenses) for delivery of a therapeutic agent to the eye are described in, e.g., Ambati and Adamis (2002) *Prog Retin Eye Res* 21 (2): 145-151; Ranta and Urtti (2006) *Adv Drug Delivery Rev* 58 (11): 1164-1181; Barocas and Balachandran (2008) *Expert Opin Drug Delivery* 5 (1): 1-10 (10); Gulsen and Chauhan (2004) *Invest Opthalmol Vis Sci* 45:2342-2347; Kim et al. (2007) *Ophthalmic Res* 39:244-254; and PCT publication no. WO 04/073551, the disclosures of which are incorporated herein by reference in their entirety.

In certain embodiments, administration of an anti-Clec12A antibody as described herein is achieved by administering to a subject a nucleic acid encoding the antibody. Nucleic acids encoding a therapeutic antibody described herein can be incorporated into a gene construct to be used as a part of a gene therapy protocol to deliver nucleic acids that can be used to express and produce antibody within cells. Expression constructs of such components may be administered in any therapeutically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin) or derivatized, polylysine conjugates, gramicidin S, artificial viral envelopes or other such intracellular carriers, as well as direct injection of the gene construct or $CaPO_4$ precipitation (see, e.g., WO04/060407). Examples of suitable retroviruses include pIJ, pZIP, pWE and pEM which are known to those skilled in the art (see, e.g., Eglitis et al. (1985) *Science* 230:1395-1398; Danos and Mulligan (1988) *Proc Natl Acad Sci USA* 85:6460-6464; Wilson et al. (1988) *Proc Natl Acad Sci USA* 85:3014-3018; Armentano et al. (1990) *Proc Natl Acad Sci USA* 87:6141-6145; Huber et al. (1991) *Proc Natl Acad Sci USA* 88:8039-8043; Ferry et al. (1991) *Proc Natl Acad Sci USA* 88:8377-8381; Chowdhury et al. (1991) *Science* 254:1802-1805; van Beusechem et al. (1992) *Proc Natl Acad Sci USA* 89:7640-7644; Kay et al. (1992) *Human Gene Therapy* 3:641-647; Dai et al. (1992) *Proc Natl Acad Sci USA* 89:10892-10895; Hwu et al. (1993) *J Immunol* 150:4104-4115; U.S. Pat. Nos. 4,868,116 and 4,980,286; and PCT Publication Nos. WO89/07136, WO89/02468, WO89/05345, and WO92/07573). Another viral gene delivery system utilizes adenovirus-derived vectors (see, e.g., Berkner et al. (1988) *BioTechniques* 6:616; Rosenfeld et al. (1991) *Science* 252:431-434; and Rosenfeld et al. (1992)

*Cell* 68:143-155). Suitable adenoviral vectors derived from the adenovirus strain Ad type 5 dl324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al. (1992) *Am J Respir Cell Mol Biol* 7:349-356; Samulski et al. (1989) *J Virol* 63:3822-3828; and Mclaughlin et al. (1989) *J Virol* 62:1963-1973.

In various embodiments, subcutaneous administration can be accomplished by means of a device, such as a syringe, a prefilled syringe, an auto-injector (e.g., disposable or reusable), a pen injector, a patch injector, a wearable injector, an ambulatory syringe infusion pump with subcutaneous infusion sets, or other device for combining with antibody drug for subcutaneous injection.

An injection system of the present disclosure may employ a delivery pen as described in U.S. Pat. No. 5,308,341. Pen devices, most commonly used for self-delivery of insulin to patients with diabetes, are well known in the art. Such devices can comprise at least one injection needle (e.g., a 31 gauge needle of about 5 to 8 mm in length), are typically pre-filled with one or more therapeutic unit doses of a therapeutic solution, and are useful for rapidly delivering solution to a subject with as little pain as possible. One medication delivery pen includes a vial holder into which a vial of a therapeutic or other medication may be received. The pen may be an entirely mechanical device or it may be combined with electronic circuitry to accurately set and/or indicate the dosage of medication that is injected into the user. See, e.g., U.S. Pat. No. 6,192,891. In some embodiments, the needle of the pen device is disposable and the kits include one or more disposable replacement needles. Pen devices suitable for delivery of any one of the presently featured compositions are also described in, e.g., U.S. Pat. Nos. 6,277,099; 6,200,296; and 6,146,361, the disclosures of each of which are incorporated herein by reference in their entirety. A microneedle-based pen device is described in, e.g., U.S. Pat. No. 7,556,615, the disclosure of which is incorporated herein by reference in its entirety. See also the Precision Pen Injector (PPI) device, MOLLY™, manufactured by Scandinavian Health Ltd.

In some embodiments, a composition described herein can be therapeutically delivered to a subject by way of local administration. As used herein, "local administration" or "local delivery," can refer to delivery that does not rely upon transport of the composition or agent to its intended target tissue or site via the vascular system. For example, the composition may be delivered by injection or implantation of the composition or agent or by injection or implantation of a device containing the composition or agent. In certain embodiments, following local administration in the vicinity of a target tissue or site, the composition or agent, or one or more components thereof, may diffuse to an intended target tissue or site that is not the site of administration.

In some embodiments, the compositions provided herein are present in unit dosage form, which unit dosage form can be suitable for self-administration. Such a unit dosage form may be provided within a container, typically, for example, a vial, cartridge, prefilled syringe or disposable pen. A doser such as the doser device described in U.S. Pat. No. 6,302, 855, may also be used, for example, with an injection system as described herein.

A suitable dose of a composition described herein, which dose is capable of treating or preventing a disorder in a subject, can depend on a variety of factors including, e.g., the age, sex, and weight of a subject to be treated and the particular inhibitor compound used. For example, a different dose of one composition including an antibody as described herein may be required to treat a subject with a Clec12A-associated disorder as compared to the dose of a different formulation of that antibody. Other factors affecting the dose administered to the subject include, e.g., the type or severity of the disorder. For example, a subject having one Clec12A-associated disorder may require administration of a different dosage than a subject with another Clec12A-associated disorder. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject may also be adjusted based upon the judgment of the treating medical practitioner.

A composition described herein can be administered as a fixed dose, or in a milligram per kilogram (mg/kg) dose. In some embodiments, the dose can also be chosen to reduce or avoid production of antibodies or other host immune responses against one or more of the antibody or an antigen-binding fragment thereof in the composition. While in no way intended to be limiting, exemplary dosages of an antibody, such as a composition described herein include, e.g., 1-1000 mg/kg, 1-100 mg/kg, 0.5-50 mg/kg, 0.1-100 mg/kg, 0.5-25 mg/kg, 1-20 mg/kg, and 1-10 mg/kg. Exemplary dosages of a composition described herein include, without limitation, 0.1 mg/kg, 0.5 mg/kg, 1.0 mg/kg, 2.0 mg/kg, 4 mg/kg, 8 mg/kg, or 20 mg/kg.

A pharmaceutical solution can include a therapeutically effective amount of a composition described herein. Such effective amounts can be readily determined by one of ordinary skill in the art based, in part, on the effect of the administered composition, or the combinatorial effect of the composition and one or more additional active agents, if more than one agent is used. A therapeutically effective amount of a composition described herein can also vary according to factors such as the disease state, age, sex, and weight of the individual, and the ability of the composition (and one or more additional active agents) to elicit a desired response in the individual, e.g., amelioration of at least one condition parameter, e.g., amelioration of at least one symptom of the a Clec12A-associated disorder. For example, a therapeutically effective amount of a composition described herein can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by therapeutically beneficial effects.

Suitable human doses of any of the compositions described herein can further be evaluated in, e.g., Phase I dose escalation studies. See, e.g., van Gurp et al. (2008) *Am J Transplantation* 8 (8): 1711-1718; Hanouska et al. (2007) *Clin Cancer Res* 13 (2, part 1): 523-531; and Hetherington et al. (2006) *Antimicrobial Agents and Chemotherapy* 50 (10): 3499-3500.

Toxicity and therapeutic efficacy of compositions can be determined by known pharmaceutical procedures in cell cultures or experimental animals (e.g., animal models of any of the Clec12A-associated disorders). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is therapeutic index and it can be expressed as the ratio $LD_{50}/ED_{50}$. A composition described herein that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

Those of skill in the art will appreciate that data obtained from cell culture assays and animal studies can be used in formulating a range of dosage for use in humans. Appropriate dosages of compositions described herein lie generally within a range of circulating concentrations of the compositions that include the $ED_{50}$ with little or no toxicity. The dosage may vary within this range depending upon the dosage form employed and the route of administration utilized. For a composition described herein, therapeutically effective dose can be estimated initially from cell culture assays. A dose can be formulated in animal models to achieve a circulating plasma concentration range that includes the $I_0$ (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

Combination Therapies

In various embodiments, an anti-Clec12A antibody as described herein may be included in a course of treatment that further includes administration of at least one additional agent to a subject. In various embodiments, an additional agent administered in combination with an anti-Clec12A antibody as described herein may be an agent chemotherapy agent. In various embodiments, an additional agent administered in combination with an antibody as described herein may be an agent that inhibits inflammation.

In some embodiments, the anti-Clec12A antigen-binding fragment thereof is a single chain variable fragment (scFv) with specificity for human Clec12A. In some embodiments, the anti-Clec12A scFv can be conjugated (e.g., linked to) to a therapeutic agent (e.g., a chemotherapeutic agent and a radioactive atom) for binding to a cancer cell, delivering therapeutic agent to the cancer cell, and killing the cancer cell which expresses human Clec12A. In some embodiments, an anti-Clec12A antibody is linked to a therapeutic agent. In some embodiments, therapeutic agent is a chemotherapeutic agent, a cytokine, a radioactive atom, an siRNA, or a toxin. In some embodiments, the therapeutic agent is a chemotherapeutic agent. In some embodiments, the therapeutic agent is a radioactive atom.

In some embodiments, the methods can be performed in conjunction with other therapies for Clec12A-associated disorders. For example, the composition can be administered to a subject at the same time, prior to, or after, chemotherapy. In some embodiments, the composition can be administered to a subject at the same time, prior to, or after, an adoptive therapy method.

In various embodiments, an additional agent administered in combination with an anti-Clec12A antibody as described herein may be administered at the same time as an anti-Clec12A antibody, on the same day as an anti-Clec12A antibody, or in the same week as an anti-Clec12A antibody. In various embodiments, an additional agent administered in combination with an anti-Clec12A antibody as described herein may be administered in a single formulation with an anti-Clec12A antibody. In certain embodiments, an additional agent administered in a manner temporally separated from administration of an anti-Clec12A antibody as described herein, e.g., one or more hours before or after, one or more days before or after, one or more weeks before or after, or one or more months before or after administration of an anti-Clec12A antibody. In various embodiments, the administration frequency of the one or more additional agents may be the same as, similar to, or different from the administration frequency of an anti-Clec12A antibody as described herein.

Encompassed within combination therapy is the a treatment regimen that includes administration of two distinct antibodies as described herein and/or a treatment regimen that includes administration of an antibody as described herein by a plurality of formulations and/or routes of administration.

In some embodiments, compositions can be formulated with one or more additional therapeutic agents, e.g., additional therapies for treating or preventing a Clec12A-associated disorder (e.g., a cancer or autoimmune disorder) in a subject. Additional agents for treating a Clec12A-associated disorder in a subject may vary depending on the particular disorder being treated, but can include, without limitation, rituximab, cyclophosphamide, doxorubicin, vincristine, prednisone, osfamide, carboplatin, etoposide, dexamethasone, cytarabine, cisplatin, cyclophosphamide, or fludarabine.

A composition described herein can replace or augment a previously or currently administered therapy. For example, upon treating with a composition described herein, administration of the one or more additional active agents can cease or diminish, e.g., be administered at lower levels, e.g., lower levels of a reference antibody that cross-competes for Clec12A binding) following administration of an anti-Clec12A antibody described herein. In some embodiments, administration of the previous therapy can be maintained. In some embodiments, a previous therapy will be maintained until the level of the composition reaches a level sufficient to provide a therapeutic effect. The two therapies can be administered in combination.

Recombinant Gene Technology

In accordance with the present disclosure, there may be employed conventional molecular biology, microbiology, and recombinant DNA techniques within the skill of the art. Such techniques are described in the literature (see, e.g., Sambrook, Fritsch & Maniatis, Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells and Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

Recombinant expression of a gene, such as a nucleic acid encoding a polypeptide, such as an anti-Clec12A antibody described herein, can include construction of an expression vector containing a nucleic acid that encodes the polypeptide. Once a polynucleotide has been obtained, a vector for the production of the polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a host cell by conventional techniques, and the transfected cells can then be cultured by conventional techniques to produce polypeptides.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

EXAMPLES

The following examples describe some of the preferred modes of making and practicing the present invention. However, it should be understood that these examples are for illustrative purposes only and are not meant to limit the scope of the invention.

Example 1. Identification and Characterization of Anti-Clec12A Antibodies

The present example demonstrates derivation and characterization of binding affinities of anti-Clec12A antibodies.

In order to select and screen for Clec12A antibodies, hybridoma technology was used. Selections were carried out on Clec12A overexpressing CHO-S cells. Antibodies were selected for a diversity of sequences. 16 antibodies were selected out of 74 antibodies for a range of soluble and on-cell Clec12A binding affinities.

The binding affinities of Clec12A antibodies were determined by Biacore analysis.

Figure 1B:
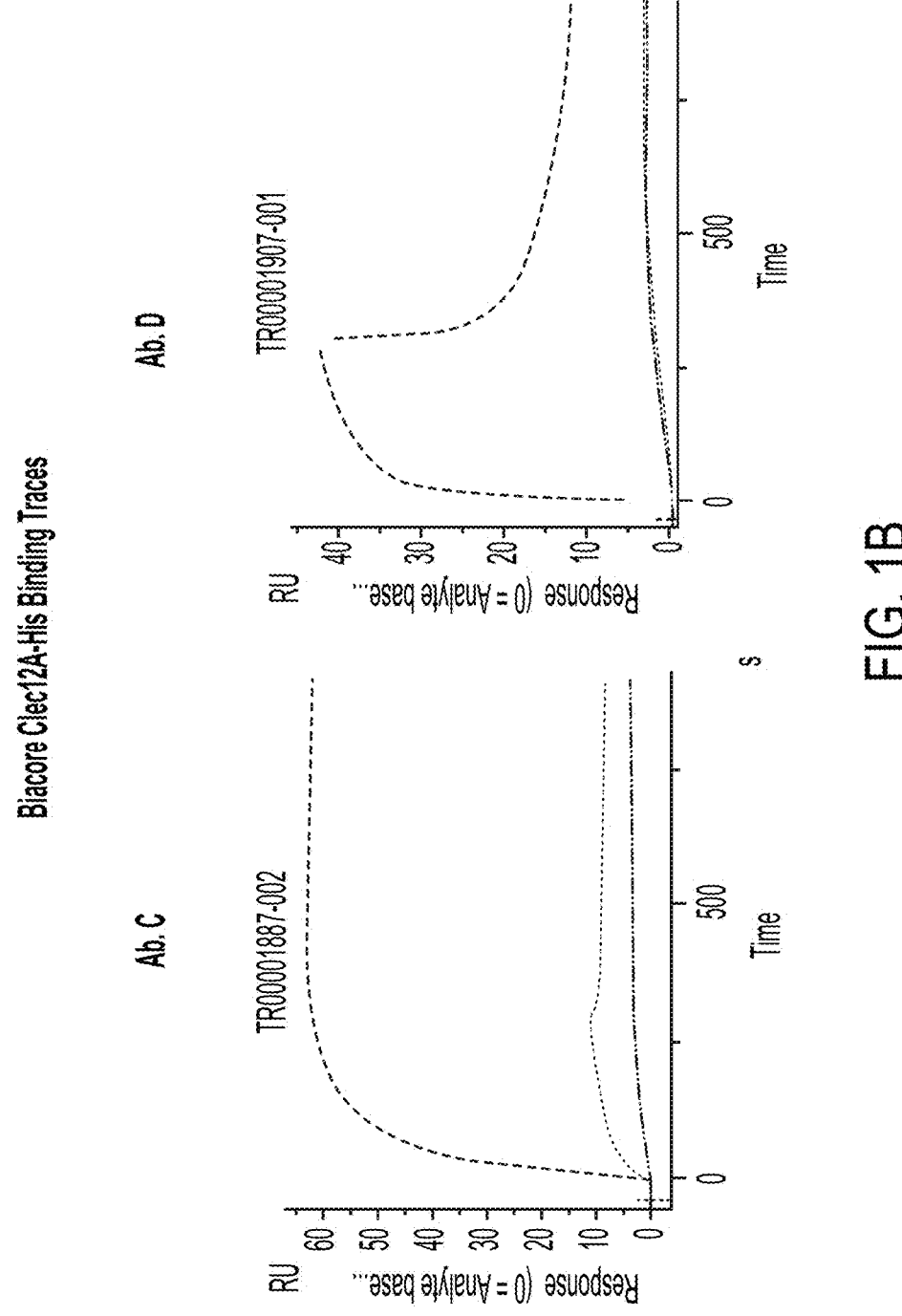

Briefly, human anti-Clec12A antibodies derived from and produced in hybridoma were tested for their binding affinity on soluble Clec12A in a Biacore SPR system. Briefly, the antibodies were immobilized on anti-mouse IgG sensor chips and bound to soluble Clec12A-His protein (Clec12A extracellular domains fused to 6× His tag (SEQ ID NO: 79)) at 100 nM in the solution phase. The resulting Biacore traces are as shown in FIGS. 1A and 1B and a summary of the binding kinetics is shown in Table 1.

TABLE 1

Summary of Biacore Clec12A-His Binding Kinetics

| Clone # | IgG $K_D$ (M) monovalent | kon (1/Ms) | koff (1/s) |
|---------|--------------------------|------------|------------|
| A | 2.87E−09 | 4.62E+06 | 1.32E−02 |
| B | 3.78E−09 | 1.76E+05 | 6.66E−04 |
| C | 4.99E−13 | 1.82E+05 | 9.08E−08 |
| D | 1.99E−09 | 2.73E+10 | 5.44E+01 |

Overall, the affinities of the anti-Clec12A antibodies ranged from the 0.1 pM at the high end (Clone C) and 3.8 nM (Clone B) on the low end.

Example 2. On-Cell Binding of Anti-Clec12A Antibodies

This example illustrates the on-cell binding for the anti-Clec12A antibodies as measured by flow cytometry.

The on-cell binding for the anti-Clec12A antibodies was assessed by flow cytometry on the Clec12A over-expressing CHO-S cell lines labelled with 100 nM Calcein-AM and the parental CHO-S cell line. Each antibody was tested on both cell lines to confirm on-cell target specific binding.

Figure 2:
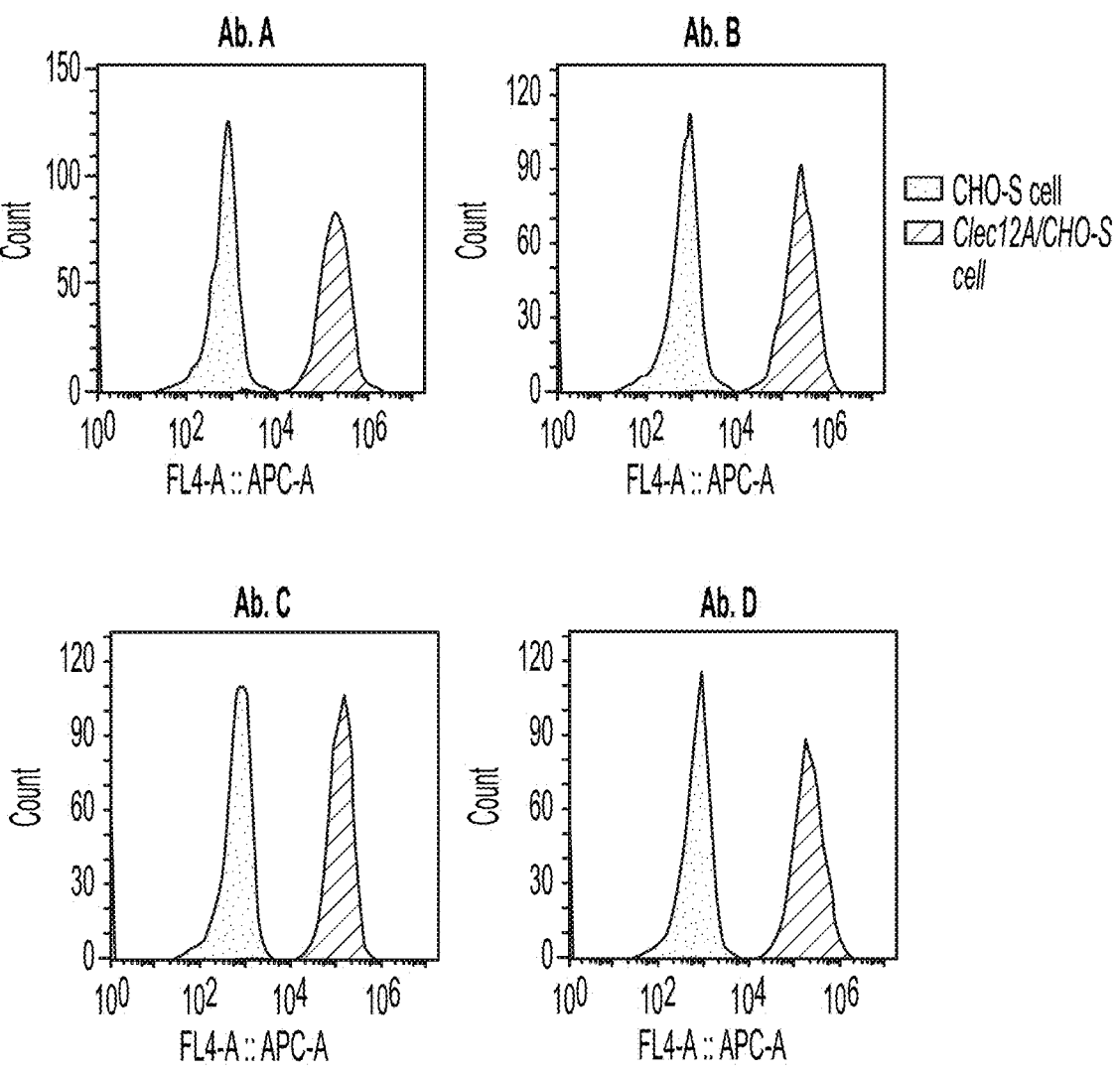
FIG. 2 shows exemplary flow cytometry histograms on wild-type and Clec12A overexpression cell lines.
Figure 3:
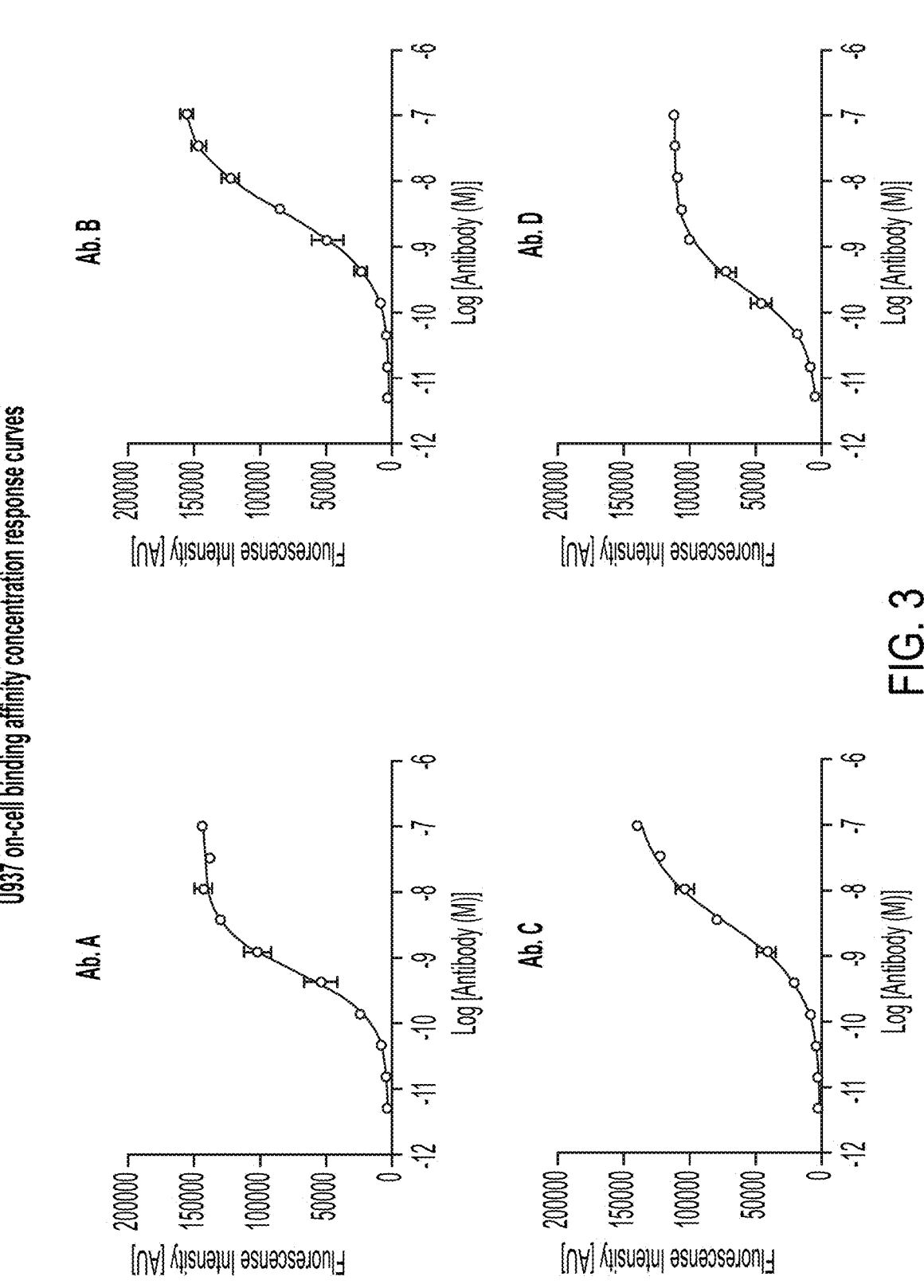
FIG. 3 shows exemplary on-cell binding affinity concentration response curves in U937 cells.

The flow cytometry chromatograms are shown in FIG. 2. The results showed 2-3 log shifts on the Clec12A positive lines over the background binding on the corresponding parental cell line.

Overall, the serial dilution flow cytometry results demonstrated saturation binding on U937 cells endogenously expressing Clec12A.

TABLE 2

Summary of EC50 of anti-Clec12A antibodies on U937 Cells

| ADI Name | U937 on-cell binding affinity $EC_{50}$ (M) |
|----------|---------------------------------------------|
| A | 6.21E−10 |
| B | 3.36E−09 |
| C | 3.35E−09 |
| D | 2.18E−10 |

As shown in Table 2, the EC50 values calculated from the curves show that each of the four antibodies binds U937 cells at high affinities from 0.2 nM (antibody D) to 3.3 nM (antibody B). The higher affinities observed on Clec12A positive cells versus the soluble protein suggests that these antibody A and antibody D antibodies bind an epitope that may be more natively presented on cells than in the Clec12A-His fusion.

Example 3. Epitope Binning by Cross Competition

A cross competition epitope binning assay was performed to determine if any of the anti-Clec12A antibodies bound a unique, non-competing epitope from two reference anti-Clec12A antibodies, Reference 1 and Reference 2.

Epitope binning/ligand blocking was performed using a sandwich format cross-blocking assay. Control anti-target IgG was loaded onto AHQ sensors and unoccupied Fc-binding sites on the sensor were blocked with an irrelevant human IgG1 antibody. The sensors were then exposed to 100 nM target antigen followed by a second anti-target antibody or ligand.

Additional binding by the second antibody or ligand after antigen association indicates an unoccupied epitope (non-competitor), while no binding indicates epitope blocking (competitor or ligand blocking).

TABLE 3

Summary of Epitope Binning

| Tested mAb Clone name | Capture mAb | |
|-----------------------|----------------------|----------------------|
| | Reference Antibody 1 | Reference Antibody 2 |
| A | 143% | 103% |
| B | 83% | 17% |
| C | 139% | 32% |
| D | 31% | 68% |
| Reference | 17% | 47% |

TABLE 3-continued

| Summary of Epitope Binning | | |
|---|---|---|
| | Capture mAb | |
| Tested mAb Clone name | Reference Antibody 1 | Reference Antibody 2 |
| Antibody 1 Reference Antibody 2 | 1% | 1% |

Figure 4:
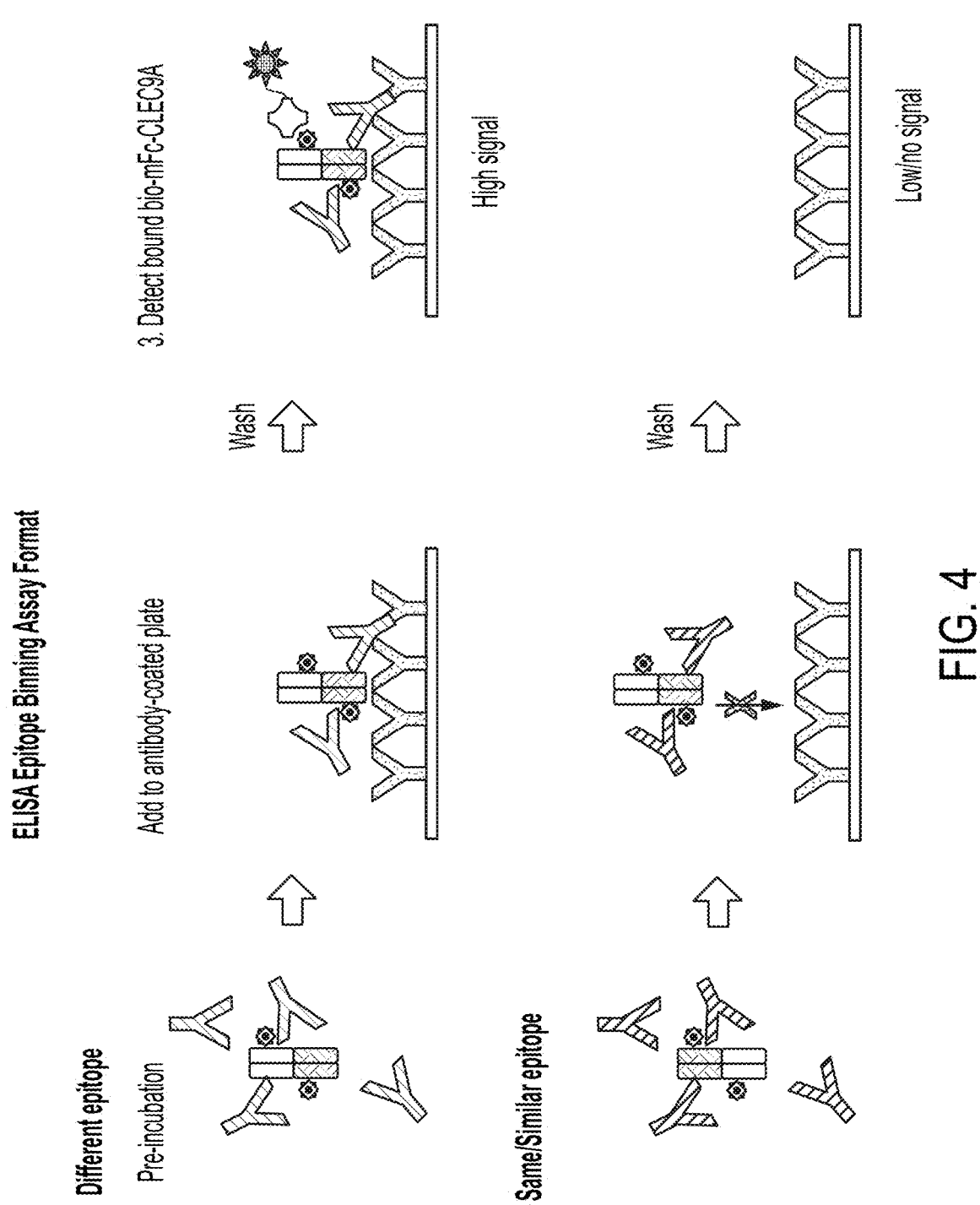
FIG. 4 shows exemplary ELISA epitope binning assay format.

The ELISA assay method used for studies included those shown in the schematic shown FIG. 4. Briefly, the anti-Clec12A reference control antibody was immobilized on ELISA plates and the plates were blocked with BSA. Each of the test antibodies was pre-incubated with soluble biotinylated Clec12A-His protein, then the mixture was added to the plates. Bound soluble Clec12A was detected with HRP-conjugated streptavidin. Those antibodies which bind a non-competing epitope from the reference antibodies would reflect a binding signal of the soluble protein to the reference antibody while antibodies with the same epitope are blocked by the reference antibodies reflected by a no or low binding signal.

The results demonstrated that anti-Clec12A antibodies B, C and D bind epitopes that compete with Reference Antibody 1 and Reference Antibody 2 respectively and antibody A binds a unique epitope.

Example 4. Characterization of Clec12A Binding of Anti-Clec12A scFv

Figure 5A:
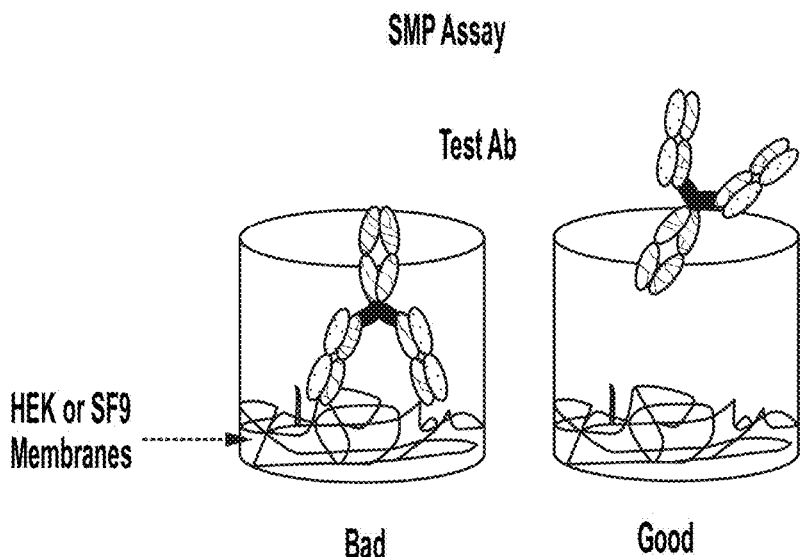
FIG. 5A shows solubilized membrane protein (SMP) assay.

This example evaluates non-specific binding of the anti-Clec12A antibodies. To assess the potential for the anti-Clec12A antibodies to bind non-specific membrane proteins, scFvs derived from the 4 lead antibodies were evaluated in a surface membrane protein (SMP) assay (FIG. 5A).

The SMP assay used was an ELISA based assay with human HEK-293 or insect SF9 cell membranes coated on the plate to test for non-specific binding to these membranes by the test antibodies. Internal control high and low non-specific binding antibodies were included.

Figure 5B:
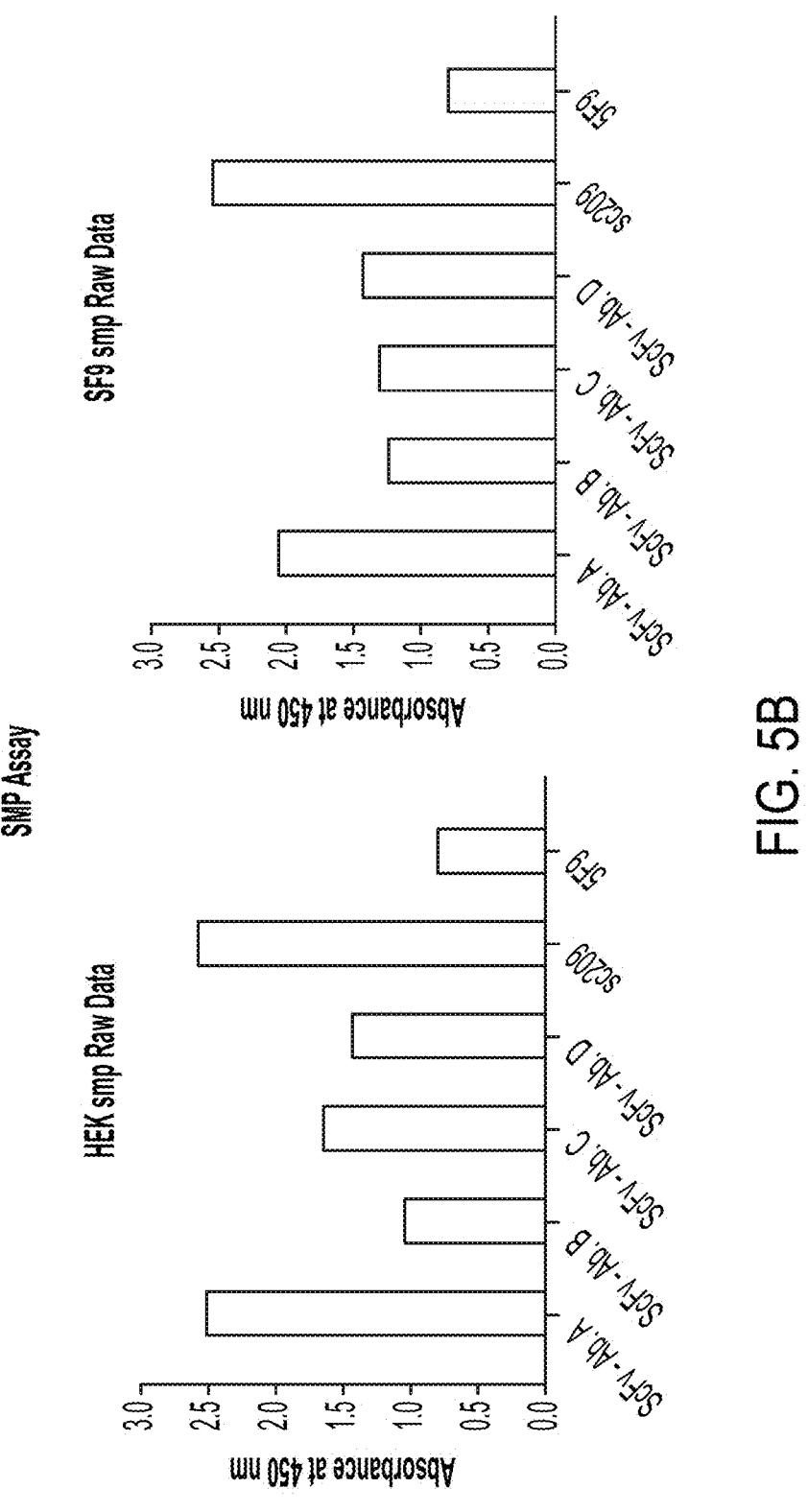
FIG. 5B shows characterization of Clec12A binding of anti-Clec12A scFv.

The high non-specific binding control, sc209, used was an antibody that has off target tox in clinic while the low non-specific binding control, 519, has not demonstrated off target tox in clinic (FIG. 5B).

Overall, the results showed low non-specific binding by anti-Clec12A antibodies B, C and D (FIG. 5B).

Example 5. Off-Target Screening Panel Assay

This example illustrates the specificity of anti-Clec12A scFvs in an off-target binding assay.

Briefly, to test anti-Clec12A scFvs for specificity to Clec12A as well as other membrane proteins, an off-target binding assay was conducted. Two selected Clec12A scFv clones were run in a "cut-down assay" to screen for binding of over 3000 human receptors.

In the cut-down assay, the higher the binding, the higher the likelihood of the interaction being real. Generally, hits labelled "V. weak" are unlikely to be real interactions. Anti-Clec12A antibody D did not show any non-specific interactions to any receptor other than Clec12A or the receptors which come up as artifacts in this assay.

The cut-down assay was used to screen clones for off-target assays. Selected scFv-Fc clones are being tested more comprehensively in additional screening and confirmation assays.

Example 6. Sequencing Anti-Clec12A Antibody Clones

The anti-Clec12A antibodies were sequenced and the variable region amino acid sequences are shown in Table 5 (heavy chain CDR sequences), Table 6 (heavy chain variable region sequences), and Table 7 (light chain CDR sequences), and Table 8 (light chain variable region sequences).

All 4 heavy chain sequences have unique CDR3s, though the anti-Clec12A antibodies B and C are all derived from the same germline framework while the anti-Clec12A antibodies A and D antibodies are unique frameworks. All 4 light chain sequences have unique CDR3s, though the B and C antibodies are all derived from the same germline framework while the A and D antibodies are unique frameworks.

TABLE 5

| Anti-Clec12A Antibody Heavy chain variable region CDR sequences | | | | | | |
|---|---|---|---|---|---|---|
| Clone # | CDR1 | SEQ ID NO: | CDR2 | SEQ ID NO: | CDR3 | SEQ ID NO: |
| A | GGSISTYY | 19 | IYYSGST | 20 | AREDYYGSGSPFDY | 21 |
| B | GFTFSSYG | 73 | ISYDGSDK | 25 | ARDKGYYFDY | 26 |
| C | GFTFSSYG | 73 | ISYDGSDK | 25 | ARDGSRYFDY | 30 |
| D | GGSISSSTYY | 33 | THYRGST | 34 | ARELTGEVFDY | 35 |
| E | GGSISTYY | 19 | IYFSGST | 38 | AREDYYGSGSPFDY | 21 |
| F | GGSISTDY | 41 | IYFSGST | 38 | AREDYYGSGSPFDY | 21 |
| G | GFTFSSYG | 73 | ISYDGSDK | 25 | ARDGQFYFDY | 43 |
| H | GFTFSNYG | 45 | ISYDGSDK | 25 | ARDSGRYFFDY | 46 |
| I | GFTFSKYG | 50 | IWYDGSIK | 51 | ARGSLWFGEFYFDY | 52 |

TABLE 6

Anti-Clec12A Antibody Heavy chain sequences

| Clone # | Germline | Heavy chain sequences | SEQ ID NO: |
|---------|----------|----------------------|------------|
| A | IGHV4-59 | QVQLQESGPGLVKPSETLSLTCTVS*GGSISTYYW* SWIRQPPGKGLEWIGYIYYSGSTKYNPSLKSRV TISVDTSKNLFSLKLSSVTAADTAVYYC*AREDY YGSGSPFDY*WGQGYLVTVSS | 1 |
| B | IGHV3-30 | QVQLVESGGGVVQPGRSLRLSCAAS*GFTFSSYG* MHWVRQAPGKGLEWVAVISYDGSDKYYVDS VKGRFTISRDNSKNTLYLHMNSLRAEDTAVYY CAR*DKGYYFDY*WGQGTLVTVSS | 3 |
| C | IGHV3-30 | QVQLVESGGGVVQPGRSLRLSCAAS*GFTFSSYG* MHWVRQAPGKGLEWVAVISYDGSDKYSADSV KGRFNISRDNSKNTLYLQMNSLRAEDTAVYC *ARDGSRYFDY*WGQGTLVTVSS | 5 |
| D | IGHV4-39 | QLQLQESGPGLVKPSETLSLTCTVS*GGSISSSTYY* WGWIRQPPRKGLEWIGSTHYRGSTYYNPSLKS RVTISVDTSKNQFSLKVSSVTAADTAVYYC*ARE LTGEVFDY*WGQGTLVTVSS | 7 |
| E | | QVQLQESGPGLVKPSETLSLTCTVSGGSISTYY WSWIRQPPGKGLEWLGYIYFSGSTNYNPSLKSR LTISVAASKSQFSLKLSSVTAADTAVYYCARED YYGSGSPFDYWGQGTLVTVSS | 9 |
| F | | QVQLQESGPGLVKPSETLSLTCTVSGGSISTDY WSWIRQPPGKGLEWIGYIYFSGSTKYNPSLKSR VTISVDTSKNQFSLKLSSVTAADTAVYYCARED YYGSGSPFDYWGQGTLVTVSS | 11 |
| G | | QVQLVESGGGVVQPGRSLRLSCAASGFTFSSYG MHWVRQAPGEGLEWVTVISYDGSDKYYADSV KGRFTISRDNSKSTLFLQMNSLRAEDTAVYYCA RDGQFYFDYWGQGTLVTVSS | 13 |
| H | | QVQLVESGGGVVQPGRSLRLSCAASGFTFSNY GMHWVRQAPGKGLEWVAVISYDGSDKSYKDS VKGRFTIARDNSKNTLYLQMNSLRAEDTAVYY CARDSGRYFFDYWGQGTLVTVSS | 15 |
| I | | QVKLVESGGGVVQPGRSLRLSCAASGFTFSKY GMHWVRQAPGKGLEWVAFIWYDGSIKNYADS VKGRFTTSRDNSKNTLYLQMNSLRAEDTAVYY CARGSLWFGEFYFDYWGQGTLVTVSS | 17 |

TABLE 7

Anti-Clec12A Antibody Light chain CDR sequences

| Clone # | CDR1 | CDR2 | CDR3 |
|---------|------|------|------|
| A | QGIRYD (SEQ ID NO: 68) | AAS (SEQ ID NO: 69) | LQDYNFPRT (SEQ ID NO: 70) |
| B | QSVGNRY (SEQ ID NO: 27) | GAS (SEQ ID NO: 28) | QQDYNLPLT (SEQ ID NO: 29) |
| C | QSVHSKY (SEQ ID NO: 71) | GAS (SEQ ID NO: 28) | QQDYNLPIT (SEQ ID NO: 32) |
| D | QSISSY (SEQ ID NO: 72) | AAS (SEQ ID NO: 23) | QQSYSTPFT (SEQ ID NO: 37) |
| E | QGIRND (SEQ ID NO: 39) | AAS (SEQ ID NO: 23) | LQDYNYPRT (SEQ ID NO: 40) |
| F | QDIRND (SEQ ID NO: 42) | AAS (SEQ ID NO: 23) | LQDYNFPRT (SEQ ID NO: 24) |
| G | QSVTSRY (SEQ ID NO: 44) | GAS (SEQ ID NO: 28) | QQDYNLPLT (SEQ ID NO: 29) |

TABLE 7-continued

| Anti-Clec12A Antibody Light chain CDR sequences | | |
| Clone # CDR1 | CDR2 | CDR3 |
| --- | --- | --- |
| H QSVSSRS (SEQ ID NO: 47) | GPS (SEQ ID NO: 48) | HQDYNLPLT (SEQ ID NO: 49) |
| I QGISSA (SEQ ID NO: 53) | DAS (SEQ ID NO: 54) | QQFNNYPRT (SEQ ID NO: 55) |

TABLE 8

Anti-Clec12A Antibody Light chain sequences

| Clone # | Light chain sequences |
| --- | --- |
| A | IQMTQSPSSLSASVGDRVTITCRASQGIRYDLGWYQQKPG KAPKLLIYAASSLQSGVPSRFSGSGSGTDFTLTISSLQPEDF ATYYCLQDYNFPRTFGQGTKVEIK (SEQ ID NO: 2) |
| B | EIVMTQSPATLSLSPGERATLSCRASQSVGNRYLSWYQQK PGQAPRLLIYGASTRATGIPARFSGSGSGTDFTLTISSLQPE DFAVYYCQQDYNLPLTFGGGTKVEIK (SEQ ID NO: 4) |
| C | EIFMTQSPATLSLSPGERATLSCRASQSVHSKYLSWYQQKP GQAPSLLIYGASTRATGIPARFSGSGSGTDFTLTISSLQPED FAVYYCQQDYNLPITFGQGTRLEIK (SEQ ID NO: 6) |
| D | DIQMTQSPSSLSASVGDRVTITCRASQSISSYLNWYQQKPG KAPKLLIYAASSLQSGVPSRFSGSGSGTDFTLTISSLQPEDF ATYYCQQSYSTPFTFGPGTKVDIK (SEQ ID NO: 8) |
| E | AIQMTQSPSSLSASVGDRVTITCRASQGIRNDLGWFQQKP GKAPKLLIYAASSLQSGVPSRFSGSGSGTYFTLTISSLQPED SATYYCLQDYNYPRTFGQGTKVEIK (SEQ ID NO: 10) |
| F | AIQMTQSPSSLSASVGDRVTITCRASQDIRNDLGWFQQKP GKAPKLLIYAASSLQSGVPSRFSGSGSGTDFTLTISSLQPED FATYYCLQDYNFPRTFGQGTKVEIK (SEQ ID NO: 12) |
| G | EIVMTQSPATLSLSPGESATLSCRASQSVTSRYLSWYQQKP GQAPRLLMYGASTRPTGIPARFSGSGSGTDFTLTISSLQPE DFAVYYCQQDYNLPLTFGGGTKVEIK (SEQ ID NO: 14) |
| H | EIIMTQSPATLSLSPGERATLSCRASQSVSSRSLSWYQHKP GQAPRLLIYGPSTRATGIPARFSGSGSGTDFTLTISSLQPED FAVYYCHQDYNLPLTFGGGTKVEIK (SEQ ID NO: 16) |
| I | AIQLTQSPSSLSASVGDRVTITCRTSQGISSALAWYQQKPG KTPKLLIYDASSLESGVPSRFSGSGSGTDFTLTISSLQPEDF ATYYCQQFNNYPRTFGQGTKVEIK (SEQ ID NO: 18) |

Example 7. Expression of Clec12A Protein

This example demonstrates the expression of Clec12A protein.

A DNA fragment encoding human Clec12A ECD (H65-A265) was fused with an N-terminal 6× histidine tag (SEQ ID NO: 79) then cloned into a pcDNA3.4 vector. The expression plasmid was transiently transfected to Expi293F cells using 293fection and the expressed protein was purified from the culture using a Ni column followed by SEC.

TABLE 9

Clec12A-His protein
Clec12A (H65-A265-WT-EOm-NIgKss-6His)

METDTLLLWVLLLWVPGSTGHHHHHHHVTLKIEMKKMNKLQNISEELQRN

ISLQLMSNMNISNKIRNLSTTLQTIATKLCRELYSKEQEHKCKPCPRRWI

WHKDSCYFLSDDVQTWQESKMACAAQNASLLKINNKNALEFIKSQSRSYD

YWLGLSPEEDSTRGMRVDNIINSSAWVIRNAPDLNNMYCGYINRLYVQYY

HCTYKKRMICEKMANPVQLGSTYFREA (SEQ ID NO: 74)

The results of the SMP assay and off-target binding assessment showed that the anti-Clec12A Clone D antibody, is a high affinity, highly specific antibody. The antibody demonstrates high affinity on Clec12A positive cells and while the soluble Clec12A affinities are somewhat lower, likely due to non-native Clec12A conformations in the soluble fusion protein. In addition, epitope binning data indicated that the Clone D antibody competes with an epitope targeted by reference 1 as well as reference 2 antibodies.

Other Embodiments

While a number of embodiments of this invention are described herein, the present disclosure and examples may be altered to provide other methods and compositions of this invention. Therefore, it will be appreciated that the scope of this invention is to be defined by the appended claims in addition to the specific embodiments that have been represented by way of example. All references cited herein are hereby incorporated by reference.

The invention claimed is:

1. An anti-Clec12A antibody or antigen-binding fragment thereof comprising:

(a) a heavy chain complementarity determining region (HCDR) 1 comprising an amino acid sequence of GGSISTYY (SEQ ID NO: 19), an HCDR2 comprising an amino acid sequence of IYYSGST (SEQ ID NO: 20), an HCDR3 comprising an amino acid sequence of AREDYYGSGSPFDY (SEQ ID NO: 21); and a light chain complementarity determining region (LCDR) 1 comprising an amino acid sequence of QGIRYD (SEQ ID NO: 22), an LCDR2 comprising an amino acid sequence of AAS (SEQ ID NO:23), and an LCDR3 comprising an amino acid sequence of LQDYNFPRT (SEQ ID NO: 24); or (b) an HCDR1 comprising an amino acid sequence of GFTFSSYG (SEQ ID NO: 73), an HCDR2 comprising an amino acid sequence of ISYDGSDK (SEQ ID NO: 25), and HCDR3 comprising an amino acid sequence of ARDKGYYFDY (SEQ ID NO: 26); and an LCDR1 comprising an amino acid sequence of QSVGNRY (SEQ ID NO: 27), an LCDR2 comprising an amino acid sequence of GAS (SEQ ID NO: 28), an LCDR3 comprising an amino acid sequence of QQDYNLPLT (SEQ ID NO:29); or (c) an HCDR1 comprising an amino acid sequence of GFTFSSYG (SEQ ID NO: 73), an HCDR2 comprising an amino acid sequence of ISYDGSDK (SEQ ID NO: 25), an HCDR3 comprising an amino acid sequence of ARDGSRYFDY (SEQ ID NO: 30); and an LCDR1 comprising an amino acid sequence of QSVHSKY (SEQ ID NO: 31), an LCDR2 comprising an amino acid sequence of GAS (SEQ ID NO: 28), an LCDR3 comprising an amino acid sequence of QQDYNLPIT (SEQ ID NO: 32); or (d) an HCDR1 comprising an amino acid sequence of GGSISSSTYY (SEQ ID NO: 33), an HCDR2 comprising an amino acid sequence of THYRGST (SEQ ID NO: 34), an HCDR3 comprising an amino acid sequence of ARELTGEVFDY (SEQ ID NO: 35); and an LCDR1 comprising an amino acid sequence of QSISSY (SEQ ID NO:36), an LCDR2 comprising an amino acid sequence of AAS (SEQ ID NO: 23), an LCDR3 comprising an amino acid sequence of QQSYSTPFT (SEQ ID NO: 37); or (e) an HCDR1 comprising an amino acid sequence of GGSISTYY (SEQ ID NO: 19), an HCDR2 comprising an amino acid sequence of IYFSGST (SEQ ID NO: 38), and HCDR3 comprising an amino acid sequence of AREDYYGSGSPFDY (SEQ ID NO:21); and an LCDR1 comprising an amino acid sequence of QGIRND (SEQ ID NO: 39), an LCDR2 comprising an amino acid sequence of AAS (SEQ ID NO: 23), an LCDR3 comprising an amino acid sequence of LQDYNYPRT (SEQ ID NO:40); or (f) an HCDR1 comprising an amino acid sequence of GGSISTDY (SEQ ID NO:41), an HCDR2 comprising an amino acid sequence of IYFSGST (SEQ ID NO:38), and HCDR3 comprising an amino acid sequence of AREDYYGSGSPFDY (SEQ ID NO:21); and an LCDR1 comprising an amino acid sequence of QDIRND (SEQ ID NO:42), an LCDR2 comprising an amino acid sequence of AAS (SEQ ID NO: 23), an LCDR3 comprising an amino acid sequence of LQDYNFPRT (SEQ ID NO: 24); or (g) an HCDR1 comprising an amino acid sequence of GFTFSSYG (SEQ ID NO: 73), an HCDR2 comprising an amino acid sequence of ISYDGSDK (SEQ ID NO:25), and HCDR3 comprising an amino acid sequence of ARDGQFYFDY (SEQ ID NO: 43); and an LCDR1 comprising an amino acid sequence of QSVTSRY (SEQ ID NO:44), an LCDR2 comprising an amino acid sequence of GAS (SEQ ID NO:28), an LCDR3 comprising an amino acid sequence of QQDYNLPLT (SEQ ID NO:29); or (h) an HCDR1 comprising an amino acid sequence of GFTFSNYG (SEQ ID NO: 45), an HCDR2 comprising an amino acid sequence of ISYDGSDK (SEQ ID NO: 25), and HCDR3 comprising an amino acid sequence of ARDSGRYFFDY (SEQ ID NO:46); and an LCDR1 comprising an amino acid sequence of QSVSSRS (SEQ ID NO:47), an LCDR2 comprising an amino acid sequence of GPS (SEQ ID NO: 48), an LCDR3 comprising an amino acid sequence of HQDYNLPLT (SEQ ID NO:49); or (i) an HCDR1 comprising an amino acid sequence of GFTFSKYG (SEQ ID NO: 50), an HCDR2 comprising an amino acid sequence of IWYDGSIK (SEQ ID NO: 51), and HCDR3 comprising an amino acid sequence of ARGSLWFGEFYFDY (SEQ ID NO: 52); and an LCDR1 comprising an amino acid sequence of QGISSA (SEQ ID NO: 53), an LCDR2 comprising an amino acid sequence of DAS (SEQ ID NO: 54), an LCDR3 comprising an amino acid sequence of QQFNNYPRT (SEQ ID NO: 55).

2. The anti-Clec12A antibody or antigen-binding fragment thereof of claim 1, wherein the anti-Clec12A antibody or fragment thereof is a monoclonal antibody or a single-chain variable fragment (scFv).

3. The anti-Clec12A antibody or antibody-binding fragment thereof of claim 2, wherein the scFv comprises a heavy chain variable sequence, a GS-Linker, and a light chain variable sequence.

4. The anti-Clec12A antibody or antigen-binding fragment thereof of claim 3, wherein the scFv comprises a sequence having at least 80% identity to:

(d) SEQ ID NO: 56;
(e) SEQ ID NO: 57;
(f) SEQ ID NO: 58; or
(g) SEQ ID NO: 59.

5. The anti-Clec 12A antibody or antigen-binding fragment thereof of claim 4, wherein the scFv comprises a sequence selected from:

(a) SEQ ID NO: 56;
(b) SEQ ID NO: 57;
(c) SEQ ID NO: 58; and
(d) SEQ ID NO: 59.

6. The anti-Clec12A antibody or antigen-binding fragment thereof of claim 1, wherein the anti-Clec12A antibody is an antibody comprising an IgG constant region.

7. A nucleic acid sequence encoding the amino acid sequence of the anti-Clec12A antibody or antigen-binding fragment thereof of claim 1.

8. A vector comprising the nucleic acid sequence of claim 7.

9. A cell comprising the vector of claim 8.

10. The anti-Clec12A antibody or antigen-binding fragment thereof according to claim 1, comprising:

(a) an immunoglobulin heavy chain variable (VH) region comprising an amino acid sequence that is at least 80% identical to SEQ ID NO: 1, and an immunoglobulin light chain variable (VL) region comprising an amino acid sequence that is at least 80% identical to SEQ ID NO: 2; or (b) an immunoglobulin heavy chain variable (VH) region comprising an amino acid sequence that is at least 80% identical to SEQ ID NO: 3, and an immunoglobulin light chain variable (VL) region comprising an amino acid sequence that is at least 80% identical to SEQ ID NO: 4; or (c) an immunoglobulin heavy chain variable (VH) region comprising an amino acid sequence that is at least 80% identical to SEQ ID NO: 5, and an immunoglobulin light chain variable (VL) region comprising an amino acid sequence that is at least 80% identical to SEQ ID NO: 6; or (d) an immunoglobulin heavy chain variable (VH) region comprising an amino acid sequence that is at least 80% identical to SEQ ID NO: 7, and an immunoglobulin light chain variable (VL) region comprising an amino acid sequence that is at least 80% identical to SEQ ID NO: 8; or (e) an immunoglobulin heavy chain variable (VH) region comprising an amino acid sequence that is at least 80% identical to SEQ ID NO: 9, and an immunoglobulin light variable (VL) region comprising an amino acid sequence that is at least 80% identical to SEQ ID NO: 10; or (f) an immunoglobulin heavy chain variable (VH) region comprising an amino acid sequence that is at least 80% identical to SEQ ID NO: 11, and an immunoglobulin light variable (VL) region comprising an amino acid sequence that is at least 80% identical to SEQ ID NO: 12; or (g) an immunoglobulin heavy chain variable (VH) region comprising an amino acid sequence that is at least 80% identical to SEQ ID NO: 13, and an immunoglobulin light variable (VL) region comprising an amino acid sequence that is at least 80% identical to SEQ ID NO: 14; or (h) an immunoglobulin heavy chain variable (VH) region comprising an amino acid sequence that is at least 80% identical to SEQ ID NO: 15, and an immunoglobulin light variable (VL) region comprising an amino acid sequence that is at least 80% identical to SEQ ID NO: 16; or (i) an immunoglobulin heavy chain variable (VH) region comprising an amino acid sequence that is at least 80% identical to SEQ ID NO: 17, and an immunoglobulin light variable (VL) region comprising an amino acid sequence that is at least 80% identical to SEQ ID NO: 18.

11. The anti-Clec12A antibody or antigen-binding fragment thereof according to claim 10, comprising:

(a) an immunoglobulin heavy chain variable (VH) region comprising an amino acid sequence of SEQ ID NO: 1, and an immunoglobulin light chain variable (VL) region comprising an amino acid sequence of SEQ ID NO: 2; or (b) an immunoglobulin heavy chain variable (VH) region comprising an amino acid sequence of SEQ ID NO: 3, and an immunoglobulin light chain variable (VL) region comprising an amino acid sequence of SEQ ID NO: 4; or (c) an immunoglobulin heavy chain variable (VH) region comprising an amino acid sequence of SEQ ID NO: 5, and an immunoglobulin light chain variable (VL) region comprising an amino acid sequence of SEQ ID NO: 6; or (d) an immunoglobulin heavy chain variable (VH) region comprising an amino acid sequence of SEQ ID NO: 7, and an immunoglobulin light chain variable (VL) region comprising an amino acid sequence of SEQ ID NO: 8; or (e) an immunoglobulin heavy chain variable (VH) region comprising an amino acid sequence of SEQ ID NO: 9, and an immunoglobulin light variable (VL) region comprising an amino acid sequence of SEQ ID NO: 10; or (f) an immunoglobulin heavy chain variable (VH) region comprising an amino acid sequence of SEQ ID NO: 11, and an immunoglobulin light variable (VL) region comprising an amino acid sequence of SEQ ID NO: 12; or (g) an immunoglobulin heavy chain variable (VH) region comprising an amino acid sequence of SEQ ID NO: 13, and an immunoglobulin light variable (VL) region comprising an amino acid sequence of SEQ ID NO: 14; or (h) an immunoglobulin heavy chain variable (VH) region comprising an amino acid sequence of SEQ ID NO: 15, and an immunoglobulin light variable (VL) region comprising an amino acid sequence of SEQ ID NO: 16; or (i) an immunoglobulin heavy chain variable (VH) region comprising an amino acid sequence of SEQ ID NO: 17, and an immunoglobulin light variable (VL) region comprising an amino acid sequence of SEQ ID NO: 18.

* * * * *

SEQUENCE LISTING

<160> NUMBER OF SEQ ID NOS: 79

<210> SEQ ID NO 1
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Lys Tyr Asn Pro Ser Leu Lys
    50                  55                  60

Ser Arg Val Thr Ile Ser Val Asp Thr Ser Lys Asn Leu Phe Ser Leu
65                  70                  75                  80

Lys Leu Ser Ser Val Thr Ala Ala Asp Thr Ala Val Tyr Tyr Cys Ala
            85                  90                  95

Arg Glu Asp Tyr Tyr Gly Ser Gly Ser Pro Phe Asp Tyr Trp Gly Gln
            100                 105                 110

Gly Thr Leu Val Thr Val Ser Ser
        115                 120

<210> SEQ ID NO 2
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ile Gln Met Thr Gln Ser Pro Ser Ser Leu Ser Ala Ser Val Gly Asp
1               5                   10                  15

Arg Val Thr Ile Thr Cys Arg Ala Ser Gln Gly Ile Arg Tyr Asp Leu
            20                  25                  30

Gly Trp Tyr Gln Gln Lys Pro Gly Lys Ala Pro Lys Leu Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Leu Gln Asp Tyr Asn Phe Pro Arg Thr
            85                  90                  95

Phe Gly Gln Gly Thr Lys Val Glu Ile Lys
            100                 105

<210> SEQ ID NO 3
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

```
Ala Val Ile Ser Tyr Asp Gly Ser Asp Lys Tyr Tyr Val Asp Ser Val
    50              55              60

Lys Gly Arg Phe Thr Ile Ser Arg Asp Asn Ser Lys Asn Thr Leu Tyr
65              70              75              80

Leu His Met Asn Ser Leu Arg Ala Glu Asp Thr Ala Val Tyr Tyr Cys
                85              90              95

Ala Arg Asp Lys Gly Tyr Tyr Phe Asp Tyr Trp Gly Gln Gly Thr Leu
            100             105             110

Val Thr Val Ser Ser
        115
```

<210> SEQ ID NO 4
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Glu Ile Val Met Thr Gln Ser Pro Ala Thr Leu Ser Leu Ser Pro Gly
1               5               10              15

Glu Arg Ala Thr Leu Ser Cys Arg Ala Ser Gln Ser Val Gly Asn Arg
            20              25              30

Tyr Leu Ser Trp Tyr Gln Gln Lys Pro Gly Gln Ala Pro Arg Leu Leu
        35              40              45

Ile Tyr Gly Ala Ser Thr Arg Ala Thr Gly Ile Pro Ala Arg Phe Ser
    50              55              60

Gly Ser Gly Ser Gly Thr Asp Phe Thr Leu Thr Ile Ser Ser Leu Gln
65              70              75              80

Pro Glu Asp Phe Ala Val Tyr Tyr Cys Gln Gln Asp Tyr Asn Leu Pro
                85              90              95

Leu Thr Phe Gly Gly Gly Thr Lys Val Glu Ile Lys
            100             105
```

<210> SEQ ID NO 5
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Gln Val Gln Leu Val Glu Ser Gly Gly Gly Val Val Gln Pro Gly Arg
1               5               10              15

Ser Leu Arg Leu Ser Cys Ala Ala Ser Gly Phe Thr Phe Ser Ser Tyr
            20              25              30

Gly Met His Trp Val Arg Gln Ala Pro Gly Lys Gly Leu Glu Trp Val
        35              40              45

Ala Val Ile Ser Tyr Asp Gly Ser Asp Lys Tyr Ser Ala Asp Ser Val
    50              55              60

Lys Gly Arg Phe Asn Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Asp Gly Ser Arg Tyr Phe Asp Tyr Trp Gly Gln Gly Thr Leu
            100             105             110
```

```
Val Thr Val Ser Ser
        115

<210> SEQ ID NO 6
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Ile Phe Met Thr Gln Ser Pro Ala Thr Leu Ser Leu Ser Pro Gly
1               5                   10                  15

Glu Arg Ala Thr Leu Ser Cys Arg Ala Ser Gln Ser Val His Ser Lys
            20                  25                  30

Tyr Leu Ser Trp Tyr Gln Gln Lys Pro Gly Gln Ala Pro Ser Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Ile Thr Phe Gly Gln Gly Thr Arg Leu Glu Ile Lys
            100                 105

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Thr Tyr Tyr Trp Gly Trp Ile Arg Gln Pro Pro Arg Lys Gly Leu Glu
        35                  40                  45

Trp Ile Gly Ser Thr His Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Val Ser Ser Val Thr Ala Ala Asp Thr Ala Val Tyr Tyr
                85                  90                  95

Cys Ala Arg Glu Leu Thr Gly Glu Val Phe Asp Tyr Trp Gly Gln Gly
            100                 105                 110

Thr Leu Val Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 9
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30

Tyr Trp Ser Trp Ile Arg Gln Pro Pro Gly Lys Gly Leu Glu Trp Leu
        35                  40                  45

Gly Tyr Ile Tyr Phe Ser Gly Ser Thr Asn Tyr Asn Pro Ser Leu Lys
    50                  55                  60

Ser Arg Leu Thr Ile Ser Val Ala Ala Ser Lys Ser Gln Phe Ser Leu
65                  70                  75                  80

Lys Leu Ser Ser Val Thr Ala Ala Asp Thr Ala Val Tyr Tyr Cys Ala
                85                  90                  95

Arg Glu Asp Tyr Tyr Gly Ser Gly Ser Pro Phe Asp Tyr Trp Gly Gln
            100                 105                 110

Gly Thr Leu Val Thr Val Ser Ser
        115                 120

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly

-continued

```
            50                  55                  60

Ser Gly Ser Gly Thr Tyr Phe Thr Leu Thr Ile Ser Ser Leu Gln Pro
65                  70                  75                  80

Glu Asp Ser Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105

<210> SEQ ID NO 11
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Asp
                20                  25                  30

Tyr Trp Ser Trp Ile Arg Gln Pro Pro Gly Lys Gly Leu Glu Trp Ile
            35                  40                  45

Gly Tyr Ile Tyr Phe Ser Gly Ser Thr Lys Tyr Asn Pro Ser Leu Lys
            50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Asp Tyr Tyr Gly Ser Gly Ser Pro Phe Asp Tyr Trp Gly Gln
            100                 105                 110

Gly Thr Leu Val Thr Val Ser Ser
            115                 120

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
                20                  25                  30

Leu Gly Trp Phe Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Phe Pro Arg
                85                  90                  95

Thr Phe Gly Gln Gly Thr Lys Val Glu Ile Lys
            100                 105
```

-continued

```
<210> SEQ ID NO 13
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Glu Gly Leu Glu Trp Val
            35                  40                  45

Thr Val Ile Ser Tyr Asp Gly Ser Asp Lys Tyr Tyr Ala Asp Ser Val
        50                  55                  60

Lys Gly Arg Phe Thr Ile Ser Arg Asp Asn Ser Lys Ser Thr Leu Phe
65                  70                  75                  80

Leu Gln Met Asn Ser Leu Arg Ala Glu Asp Thr Ala Val Tyr Tyr Cys
                85                  90                  95

Ala Arg Asp Gly Gln Phe Tyr Phe Asp Tyr Trp Gly Gln Gly Thr Leu
            100                 105                 110

Val Thr Val Ser Ser
        115

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Ile Val Met Thr Gln Ser Pro Ala Thr Leu Ser Leu Ser Pro Gly
1               5                   10                  15

Glu Ser Ala Thr Leu Ser Cys Arg Ala Ser Gln Ser Val Thr Ser Arg
                20                  25                  30

Tyr Leu Ser Trp Tyr Gln Gln Lys Pro Gly Gln Ala Pro Arg Leu Leu
            35                  40                  45

Met Tyr Gly Ala Ser Thr Arg Pro Thr Gly Ile Pro Ala Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Leu Thr Phe Gly Gly Gly Thr Lys Val Glu Ile Lys
            100                 105

<210> SEQ ID NO 15
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Glu Ser Gly Gly Gly Val Val Gln Pro Gly Arg
1               5                   10                  15
```

-continued

```
Ser Leu Arg Leu Ser Cys Ala Ala Ser Gly Phe Thr Phe Ser Asn Tyr
        20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Ser Tyr Lys Asp Ser Val
    50                  55                  60

Lys Gly Arg Phe Thr Ile Ala Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Gly Arg Tyr Phe Phe Asp Tyr Trp Gly Gln Gly Thr
            100                 105                 110

Leu Val Thr Val Ser Ser
        115
```

```
<210> SEQ ID NO 16
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Ile Ile Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Ser Leu Ser Trp Tyr Gln His Lys Pro Gly Gln Ala Pro Arg Leu Leu
        35                  40                  45

Ile Tyr Gly Pro Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys His Gln Asp Tyr Asn Leu Pro
                85                  90                  95

Leu Thr Phe Gly Gly Gly Thr Lys Val Glu Ile Lys
            100                 105
```

```
<210> SEQ ID NO 17
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Lys Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Lys Tyr
            20                  25                  30

Gly Met His Trp Val Arg Gln Ala Pro Gly Lys Gly Leu Glu Trp Val
        35                  40                  45

Ala Phe Ile Trp Tyr Asp Gly Ser Ile Lys Asn Tyr Ala Asp Ser Val
    50                  55                  60

Lys Gly Arg Phe Thr Thr Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Gly Ser Leu Trp Phe Gly Glu Phe Tyr Phe Asp Tyr Trp Gly
            100                 105                 110

Gln Gly Thr Leu Val Thr Val Ser Ser
        115                 120

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Ile Gln Leu Thr Gln Ser Pro Ser Ser Leu Ser Ala Ser Val Gly
1               5                   10                  15

Asp Arg Val Thr Ile Thr Cys Arg Thr Ser Gln Gly Ile Ser Ser Ala
            20                  25                  30

Leu Ala Trp Tyr Gln Gln Lys Pro Gly Lys Thr Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Asn Tyr Pro Arg
                85                  90                  95

Thr Phe Gly Gln Gly Thr Lys Val Glu Ile Lys
            100                 105

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Ser Ile Ser Thr Tyr Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Tyr Tyr Ser Gly Ser Thr
1               5

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 21

Ala Arg Glu Asp Tyr Tyr Gly Ser Gly Ser Pro Phe Asp Tyr
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gly Ile Arg Tyr Asp
1               5

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ala Ser
1

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Gln Asp Tyr Asn Phe Pro Arg Thr
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Ser Tyr Asp Gly Ser Asp Lys
1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Arg Asp Lys Gly Tyr Tyr Phe Asp Tyr
1               5                   10

<210> SEQ ID NO 27
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 27

Gln Ser Val Gly Asn Arg Tyr
1               5

<210> SEQ ID NO 28
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Ala Ser
1

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Gln Asp Tyr Asn Leu Pro Leu Thr
1               5

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Arg Asp Gly Ser Arg Tyr Phe Asp Tyr
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Ser Val His Ser Lys Tyr
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln Asp Tyr Asn Leu Pro Ile Thr
1               5
```

-continued

```
<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Ser Ile Ser Ser Ser Thr Tyr Tyr
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr His Tyr Arg Gly Ser Thr
1               5

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Arg Glu Leu Thr Gly Glu Val Phe Asp Tyr
1               5                   10

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ser Ile Ser Ser Tyr
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Gln Ser Tyr Ser Thr Pro Phe Thr
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 38

Ile Tyr Phe Ser Gly Ser Thr
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Gly Ile Arg Asn Asp
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Leu Gln Asp Tyr Asn Tyr Pro Arg Thr
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Gly Ser Ile Ser Thr Asp Tyr
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Asp Ile Arg Asn Asp
1               5

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Arg Asp Gly Gln Phe Tyr Phe Asp Tyr
1               5                   10

<210> SEQ ID NO 44
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Ser Val Thr Ser Arg Tyr
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Phe Thr Phe Ser Asn Tyr Gly
1               5

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Arg Asp Ser Gly Arg Tyr Phe Phe Asp Tyr
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ser Val Ser Ser Arg Ser
1               5

<210> SEQ ID NO 48
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Pro Ser
1

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

His Gln Asp Tyr Asn Leu Pro Leu Thr
```

```
1               5
```

```
<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Phe Thr Phe Ser Lys Tyr Gly
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ile Trp Tyr Asp Gly Ser Ile Lys
1               5

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Arg Gly Ser Leu Trp Phe Gly Glu Phe Tyr Phe Asp Tyr
1               5                   10

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Gly Ile Ser Ser Ala
1               5

<210> SEQ ID NO 54
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Ala Ser
1

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 55

Gln Gln Phe Asn Asn Tyr Pro Arg Thr
1               5

<210> SEQ ID NO 56
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Lys Tyr Asn Pro Ser Leu Lys
        50                  55                  60

Ser Arg Val Thr Ile Ser Val Asp Thr Ser Lys Asn Leu Phe Ser Leu
65                  70                  75                  80

Lys Leu Ser Ser Val Thr Ala Ala Asp Thr Ala Val Tyr Tyr Cys Ala
                85                  90                  95

Arg Glu Asp Tyr Tyr Gly Ser Gly Ser Pro Phe Asp Tyr Trp Gly Gln
                100                 105                 110

Gly Thr Leu Val Thr Val Ser Ser Ala Ser Thr Gly Gly Gly Gly Ser
            115                 120                 125

Gly Gly Gly Gly Ser Gly Gly Gly Ser Ala Ile Gln Met Thr Gln
        130                 135                 140

Ser Pro Ser Ser Leu Ser Ala Ser Val Gly Asp Arg Val Thr Ile Thr
145                 150                 155                 160

Cys Arg Ala Ser Gln Gly Ile Arg Tyr Asp Leu Gly Trp Tyr Gln Gln
                165                 170                 175

Lys Pro Gly Lys Ala Pro Lys Leu Leu Ile Tyr Ala Ala Ser Ser Leu
                180                 185                 190

Gln Ser Gly Val Pro Ser Arg Phe Ser Gly Ser Gly Ser Gly Thr Asp
            195                 200                 205

Phe Thr Leu Thr Ile Ser Ser Leu Gln Pro Glu Asp Phe Ala Thr Tyr
        210                 215                 220

Tyr Cys Leu Gln Asp Tyr Asn Phe Pro Arg Thr Phe Gly Gln Gly Thr
225                 230                 235                 240

Lys Val Glu Ile Lys
                245

<210> SEQ ID NO 57
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Val Glu Ser Gly Gly Gly Val Val Gln Pro Gly Arg
1               5                   10                  15

-continued

```
Ser Leu Arg Leu Ser Cys Ala Ala Ser Gly Phe Thr Phe Ser Ser Tyr
        20                  25                  30

Gly Met His Trp Val Arg Gln Ala Pro Gly Lys Gly Leu Glu Trp Val
        35                  40                  45

Ala Ile Val Ile Ser Tyr Asp Gly Ser Asp Lys Tyr Tyr Val Asp Ser
    50                  55                  60

Val Lys Gly Arg Phe Thr Ile Ser Arg Asp Asn Ser Lys Asn Thr Leu
65                  70                  75                  80

Tyr Leu His Met Asn Ser Leu Arg Ala Glu Asp Thr Ala Val Tyr Tyr
                85                  90                  95

Cys Ala Arg Asp Lys Gly Tyr Tyr Phe Asp Tyr Trp Gly Gln Gly Thr
            100                 105                 110

Leu Val Thr Val Ser Ser Ala Ser Thr Gly Gly Gly Gly Ser Gly Gly
            115                 120                 125

Gly Gly Ser Gly Gly Gly Gly Ser Glu Ile Val Met Thr Gln Ser Pro
    130                 135                 140

Ala Thr Leu Ser Leu Ser Pro Gly Glu Arg Ala Thr Leu Ser Cys Arg
145                 150                 155                 160

Ala Ser Gln Ser Val Gly Asn Arg Tyr Leu Ser Trp Tyr Gln Gln Lys
                165                 170                 175

Pro Gly Gln Ala Pro Arg Leu Leu Ile Tyr Gly Ala Ser Thr Arg Ala
            180                 185                 190

Thr Gly Ile Pro Ala Arg Phe Ser Gly Ser Gly Ser Gly Thr Asp Phe
            195                 200                 205

Thr Leu Thr Ile Ser Ser Leu Gln Pro Glu Asp Phe Ala Val Tyr Tyr
    210                 215                 220

Cys Gln Gln Asp Tyr Asn Leu Pro Leu Thr Phe Gly Gly Gly Thr Lys
225                 230                 235                 240

Val Glu Ile Lys
```

<210> SEQ ID NO 58
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
        20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Ser Ala Asp Ser Val
    50                  55                  60

Lys Gly Arg Phe Asn Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ser Arg Tyr Phe Asp Tyr Trp Gly Gln Gly Thr Leu
            100                 105                 110

Val Thr Val Ser Ser Ala Ser Thr Gly Gly Gly Gly Ser Gly Gly Gly
            115                 120                 125
```

```
Gly Ser Gly Gly Gly Gly Ser Glu Ile Phe Met Thr Gln Ser Pro Ala
    130                 135                 140

Thr Leu Ser Leu Pro Gly Glu Arg Ala Thr Leu Ser Cys Arg Ala Ser
145                 150                 155                 160

Gln Ser Val His Ser Lys Tyr Leu Ser Trp Tyr Gln Gln Lys Pro Gly
                165                 170                 175

Gln Ala Pro Ser Leu Leu Ile Tyr Gly Ala Ser Thr Arg Ala Thr Gly
                180                 185                 190

Ile Pro Ala Arg Phe Ser Gly Ser Gly Ser Gly Thr Asp Phe Thr Leu
            195                 200                 205

Thr Ile Ser Ser Leu Gln Pro Glu Asp Phe Ala Val Tyr Tyr Cys Gln
    210                 215                 220

Gln Asp Tyr Asn Leu Pro Ile Thr Phe Gly Gln Gly Thr Arg Leu Glu
225                 230                 235                 240

Ile Lys
```

```
<210> SEQ ID NO 59
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59
```

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Thr Tyr Tyr Trp Gly Trp Ile Arg Gln Pro Pro Arg Lys Gly Leu Glu
            35                  40                  45

Trp Ile Gly Ser Thr His Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Val Ser Ser Val Thr Ala Ala Asp Thr Ala Val Tyr Tyr
                85                  90                  95

Cys Ala Arg Glu Leu Thr Gly Glu Val Phe Asp Tyr Trp Gly Gln Gly
            100                 105                 110

Thr Leu Val Thr Val Ser Ser Ala Ser Thr Gly Gly Gly Gly Ser Gly
            115                 120                 125

Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
                165                 170                 175

Pro Gly Lys Ala Pro Lys Leu Leu Ile Tyr Ala Ala Ser Ser Leu Gln
                180                 185                 190

Ser Gly Val Pro Ser Arg Phe Ser Gly Ser Gly Ser Gly Thr Asp Phe
            195                 200                 205

Thr Leu Thr Ile Ser Ser Leu Gln Pro Glu Asp Phe Ala Thr Tyr Tyr
    210                 215                 220

Cys Gln Gln Ser Tyr Ser Thr Pro Phe Thr Phe Gly Pro Gly Thr Lys
225                 230                 235                 240
```

Val Asp Ile Lys

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Gly Gly Gly Ser Gly Gly Gly Gly Ser Gly Gly Gly Gly Ser
1               5                   10                  15

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Gly Gly Gly Ser Gly Gly Gly Gly Ser Gly Gly Gly Ser Gly Gly
1               5                   10                  15

Gly Gly Ser

<210> SEQ ID NO 62
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Met Tyr Arg Met Gln Leu Leu Ser Cys Ile Ala Leu Ser Leu Ala Leu
1               5                   10                  15

Val Thr Asn Ser
            20

<210> SEQ ID NO 63
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Gly Gly Gly Ser Gly Gly Gly Gly Ser Gly Gly Gly Gly Ser Gly
1               5                   10                  15

Gly Gly Ser Gly Gly Gly Gly Ser
            20

<210> SEQ ID NO 64
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gly Gly Gly Ser Gly Gly Gly Gly Ser Gly Gly Gly Gly Ser Gly

-continued

```
1               5                   10                  15

Gly Gly Gly Ser Gly Gly Gly Ser Gly Gly Gly Ser
            20                  25

<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Met Ala Leu Pro Val Thr Ala Leu Leu Leu Pro Leu Ala Leu Leu Leu
1               5                   10                  15

His Ala Ala Arg Pro
            20

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Met Lys Trp Val Thr Phe Ile Ser Leu Leu Phe Ser Ser Ala Tyr Ser
1               5                   10                  15

<210> SEQ ID NO 67
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Met Asp Ser Lys Gly Ser Ser Gln Lys Gly Ser Arg Leu Leu Leu Leu
1               5                   10                  15

Leu Val Val Ser Asn Leu Leu Leu Cys Gln Gly Val Val Ser
            20                  25                  30

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gly Ile Arg Tyr Asp
1               5

<210> SEQ ID NO 69
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Ala Ser
```

-continued

1

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 70

Leu Gln Asp Tyr Asn Phe Pro Arg Thr
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 71

Gln Ser Val His Ser Lys Tyr
1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 72

Gln Ser Ile Ser Ser Tyr
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 73

Gly Phe Thr Phe Ser Ser Tyr Gly
1               5

<210> SEQ ID NO 74
<211> LENGTH: 227
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 74

Met Glu Thr Asp Thr Leu Leu Leu Trp Val Leu Leu Leu Trp Val Pro
1               5                   10                  15

Gly Ser Thr Gly His His His His His His Val Thr Leu Lys Ile
            20                  25                  30

Glu Met Lys Lys Met Asn Lys Leu Gln Asn Ile Ser Glu Glu Leu Gln
        35                  40                  45

Arg Asn Ile Ser Leu Gln Leu Met Ser Asn Met Asn Ile Ser Asn Lys

```
            50                  55                  60

Ile Arg Asn Leu Ser Thr Thr Leu Gln Thr Ile Ala Thr Lys Leu Cys
65                  70                  75                  80

Arg Glu Leu Tyr Ser Lys Glu Gln Glu His Lys Cys Lys Pro Cys Pro
                    85                  90                  95

Arg Arg Trp Ile Trp His Lys Asp Ser Cys Tyr Phe Leu Ser Asp Asp
                100                 105                 110

Val Gln Thr Trp Gln Glu Ser Lys Met Ala Cys Ala Ala Gln Asn Ala
            115                 120                 125

Ser Leu Leu Lys Ile Asn Asn Lys Asn Ala Leu Glu Phe Ile Lys Ser
            130                 135                 140

Gln Ser Arg Ser Tyr Asp Tyr Trp Leu Gly Leu Ser Pro Glu Glu Asp
145                 150                 155                 160

Ser Thr Arg Gly Met Arg Val Asp Asn Ile Ile Asn Ser Ser Ala Trp
                165                 170                 175

Val Ile Arg Asn Ala Pro Asp Leu Asn Asn Met Tyr Cys Gly Tyr Ile
                180                 185                 190

Asn Arg Leu Tyr Val Gln Tyr Tyr His Cys Thr Tyr Lys Lys Arg Met
            195                 200                 205

Ile Cys Glu Lys Met Ala Asn Pro Val Gln Leu Gly Ser Thr Tyr Phe
            210                 215                 220

Arg Glu Ala
225
```

```
<210> SEQ ID NO 75
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Met Glu Thr Asp Thr Leu Leu Leu Trp Val Leu Leu Leu Trp Val Pro
1               5                   10                  15

Gly Ser Thr Gly
            20
```

```
<210> SEQ ID NO 76
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Met Tyr Ser Met Gln Leu Ala Ser Cys Val Thr Leu Thr Leu Val Leu
1               5                   10                  15

Leu Val Asn Ser
            20
```

```
<210> SEQ ID NO 77
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77
```

-continued

```
Met Glu Thr Pro Ala Gln Leu Leu Phe Leu Leu Leu Leu Trp Leu Pro
1                5                  10                  15

Asp Thr Thr Gly
            20

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Gly Gly Gly Ser
1               5

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 79

His His His His His His
1               5
```